(12) United States Patent
Sette et al.

(10) Patent No.: US 7,252,829 B1
(45) Date of Patent: *Aug. 7, 2007

(54) HLA BINDING PEPTIDES AND THEIR USES

(75) Inventors: Alessandro Sette, La Jolla, CA (US); John Sidney, San Diego, CA (US); Scott Southwood, Santee, CA (US); Esteban Celis, Rochester, MN (US)

(73) Assignee: IDM Pharma, Inc., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/189,702

(22) Filed: Nov. 10, 1998

Related U.S. Application Data

(63) Continuation-in-part of application No. 09/098,584, filed on Jun. 17, 1998, now abandoned.

(51) Int. Cl.
*A61K 38/08* (2006.01)
*A61K 38/10* (2006.01)
*A61K 39/00* (2006.01)
*C07K 4/12* (2006.01)

(52) U.S. Cl. .............. 424/277.1; 424/185.1; 424/450; 514/2; 514/12; 514/13; 514/14; 514/15; 514/16; 530/324; 530/325; 530/326; 530/327; 530/328

(58) Field of Classification Search .......... 424/185.1, 424/277.1, 450; 514/2, 15, 14, 13, 12, 16; 530/324, 325, 326, 327, 328
See application file for complete search history.

(56) References Cited

U.S. PATENT DOCUMENTS

| | | | |
|---|---|---|---|
| 4,599,230 A | 7/1986 | Milich et al. | 424/189.1 |
| 5,028,425 A | 7/1991 | Good et al. | 424/191.1 |
| 5,200,320 A | 4/1993 | Sette et al. | 435/7.24 |
| 5,342,774 A | 8/1994 | Boon et al. | 435/371 |
| 5,405,940 A | 4/1995 | Boon et al. | 530/328 |
| 5,462,871 A | 10/1995 | Boon-Falleur et al. | 435/354 |
| 5,503,829 A | 4/1996 | Ladant et al. | 424/192.1 |
| 5,662,907 A | 9/1997 | Kubo et al. | 424/185.1 |
| 5,686,068 A | 11/1997 | Melief et al. | |
| 5,736,142 A | 4/1998 | Sette et al. | 424/185.1 |
| 5,750,395 A | 5/1998 | Fikes et al. | 435/325 |
| 5,783,567 A | 7/1998 | Hedley et al. | |
| 5,840,303 A | 11/1998 | Chisari et al. | 424/152.1 |
| 6,037,135 A | 3/2000 | Kubo et al. | 435/7.24 |
| 6,063,900 A | 5/2000 | Melief et al. | 530/327 |
| 6,075,122 A | 6/2000 | Cheever et al. | 530/350 |
| 6,514,942 B1 * | 2/2003 | Ioannides et al. | 514/15 |

FOREIGN PATENT DOCUMENTS

| | | |
|---|---|---|
| EP | 44710 | 1/1982 |
| EP | 0226513 | 6/1987 |
| EP | 0346022 | 6/1989 |
| EP | 0534615 | 8/1996 |
| EP | 0728764 | 8/1996 |
| WO | WO 92/02543 | 2/1992 |
| WO | WO92/12996 | 8/1992 |
| WO | WO 92/21033 | 11/1992 |
| WO | WO 93/03753 | 3/1993 |
| WO | WO 93/03764 | 3/1993 |
| WO | WO 93/17095 | 9/1993 |
| WO | WO 93/20103 | 10/1993 |
| WO | WO 93/22338 | 11/1993 |
| WO | WO 94/03205 | 2/1994 |
| WO | WO94/05304 | 3/1994 |
| WO | WO 94/11738 | 5/1994 |
| WO | 94/20127 * | 9/1994 |
| WO | WO 94/20127 | 9/1994 |
| WO | WO 95/11255 | 4/1995 |
| WO | WO 95/23234 | 8/1995 |
| WO | 96/18409 * | 6/1996 |
| WO | WO96/18409 | 6/1996 |
| WO | 96/22067 * | 7/1996 |
| WO | WO 97/04802 | 2/1997 |
| WO | WO 97/29195 | 8/1997 |
| WO | WO 97/41440 | 11/1997 |
| WO | WO 98/33888 A1 | 8/1998 |
| WO | WO 01/41788 A1 | 6/2001 |

OTHER PUBLICATIONS

Tsang et al., J. Nat Cancer Inst., 87:892-990, 1995.*
J. Blok and G.M. Air, *Virology* (1982) 121: 211-229.
Houbiers et al., *Eur. J. Immunol.* (1993) 23: 2072-2077.
Gnjatic et al., *Eur. J. Immunol.* (1995) 25: 1638-1642.
Konda et al., "Prominent Roles in Secondary Anchor Residues in Peptide Binding to HLA-A24 Human Class I Molecules," *Journal of Immunology* (1995) 155: 4307-4312.
Nijman, H.W. et al. (1993) *Journal of Immunotherapy* 14(2):121-126.
Ras, E. et al. (1997) *Human Immunology* 53:81-89.
Zaremba, S. et a. (1997) *Cancer Research* 57:4570-4577.

(Continued)

*Primary Examiner*—Ronald B. Schwadron
(74) *Attorney, Agent, or Firm*—Sterne, Kessler, Goldstein & Fox PLLC

(57) ABSTRACT

The present invention provides the means and methods for selecting immunogenic peptides and the immunogenic peptide compositions capable of specifically binding glycoproteins encoded by HLA alleles and inducing T cell activation in T cells restricted by the allele. The peptides are useful to elicit an immune response against a desired antigen. The immunogenic peptide compositions of the present invention comprise immunogenic peptides having an HLA binding motif, where the peptide is from a target antigen. Target antigens of the present invention include prostate specific antigen (PSA), hepatitis B core and surface antigens (HBVc, HBVs) hepatitis C antigens, Epstein-Barr virus antigens, melanoma antigens (e.g., MAGE-1), human immunodeficiency virus (HIV) antigens, human papilloma virus (HPV) antigens, Lassa virus, *mycobacterium tuberculosis* (MT), p53, CEA, trypanosome surface antigen (TSA) and Her2/neu. An example of an immunogenic peptide of the present invention corresponds to a peptide less than about 15 amino acids in length that comprises an HLA-A2.1 binding motif, where the peptide comprises the p53 sequence SMPPPGTRV.

3 Claims, No Drawings

OTHER PUBLICATIONS

Gnjatic, S., et al., "Mapping and ranking of potential cytotoxic T epitopes in the p53 protein: effect of mutations and polymorphism on peptide binding to purified and refolded HLA molecules," *Eur. J. Immunol.* 25:1638-1642, VCH Verlagsgesellschaft mbH (1995).

Harlow, E. et al., "Molecular Cloning and In Vitro Expression of a cDNA Clone for Human Cellular Tumor Antigen p53," *Mol. Cell. Biol.* 5: 1601-1610, American Society for Microbiology (1985).

Harris, N., et al., "Molecular Basis for Heterogeneity of the Human p53 Protein," *Mol. Cell. Biol.* 6:4650-4656, American Society for Microbiology (1986).

Lamb, P., and Crawford, L., "Characterization of the Human p53 Gene," *Mol. Cell. Biol.* 6:1379-1385, American Society for Microbiology (1986).

Röpke, M., et al., "T Cell-Mediated Cytotoxicity Against p53-Protein Derived Peptides in Bulk and Limiting Dilution Cultures of Healthy Donors," *Scand. J. Immunol.* 42:98-103, Blackwell Science Limited (1995).

Toes, R.E.M., et al., "Enhancement of Tumor Outgrowth Through CTL Tolerization After Peptide Vaccination Is Avoided by Peptide Presentation on Dendritic Cells," *J. Immunol.* 160:4449-4456, The American Association of Immunologists (1998).

Vojtesek, B., et al., "Conformational changes in p53 analysed using new antibodies to the core DNA binding domain of the protein," *Oncogene* 10:389-393, Stockton Press (1995).

Zakut-Houri, R., et al., "Human p53 cellular tumor antigen: cDNA sequence and expression in COS cells," *EMBO J* 4:1251-1255, IRL Press Limited (1985).

Alexander et al. "Generation of Tumor-specific Cytolytic T Lymphocytes from Peripheral Blood of Cervical Cancer Patients by In Vitro Stimulation with a Synthetic Human Papillomavirus Type 16 E7 Epitope" Am. J. Obstet. Gynecol. 175:1586-1593 (1996).

Alexander et al., J. Immunol. (1997) 159:4753-4761.

Altfeld et al., J. Virol. (2001) 75:1301-1311.

Benjamin et al., Nature (1991) 351:74-77.

Bergmann et al., J. Virol. (1994) 68:5306-5310.

Bertoni et al., J. Clin. Invest. (1997) 100:503-513.

Bjorkman et al. "Structure of the Human Class I Histocompatibility Antigen HLA-A2" Nature 329:506 (1987).

Boel et al., Immunity (1995) 2:167.

Boon. Tumor Antigens Recognized by Cytoloytic T Lymohocytes: Present Perspectives for Specific Immunotherapy Int. J. Cancer 54:177-180 (1993).

Bosisio et al., Gazz. Chim. Ital. (1967) 97(12):1848-1857.

Bruss. "A Short Linear Sequence in the Pre-S Domain of the Large Hepatitis B Virus Envelope Protein Required from Virion Formation" J. Virology 71(12):9350-9357 (1997).

Buus et al. "Autologous Peptides Constitutively Occupy the Antigen Binding Site on Ia" Science 242:1045-1047 (1988).

Carreno et al. "HLA-B37 and HLA-A2.1 Molecules Bind Largely Nonoverlapping Sets of Peptides" Proc. Natl. Acad. Sci. USA 87:3420-3424 (1990).

Castellanos et al., Gynecologic Oncology (2001) 82:77-83.

Castellanos et al., Oncology/Hematology (2001) 39:133-138.

Celis et al. "Identification of Potential CTL Epitopes of Tumor Associated Antigen MAGE-1 for Five Common HLA-A Alleles" Molec. Immunol. 3:1423-1430 (1994).

Celis et al. "Epitope Selection and Develeopment of Peptide Based Vaccines to Treat Cancer" Cancer Biology 6:329-336 (1995).

Chang et al., J. Immunol. (1999) 162:1156-1164.

Chen and Parham, Nature (1989) 337:743-745.

Cotran et al. (ed.) *Robbins Pathologic Basis of Disease*, 4th ed., W.B. Saunders Co., Philadelphia pp. 296-299 (1989).

Culmann et al., (1991) 146(5):1560-1565.

De Bruijn et al. "Peptide Loading of Empty Major Histocompatibility Complex Molecules on RMA-S Cells Allows the Induction of Primary Cytotoxic T Lymphocyte Responses" Eur. J. Immunol. 21:2963-2970 (1990).

Del Val et al., Cell (1991) 66:1145-1153.

DiBrino et al. "Endogenous Peptides Bound to HLA-A3 Possess a Specific Combination of Anchor Residues That Permit Identification of Potential Antigenic Peptides" Proc. Nat'l. Acad. Sci. USA 90:1508-1512 (1993).

Dibrino et al., J. Immunol. (1993) 151:5930-5935.

Diepolder et al., J. Virol. (1997) 71(8):6011-6019.

Ding et al. "Cloning and Analysis of MAGE-1-Related Genes" Biochem. Biophys. Res. Commun. 202(1):549-555 (1994).

Ding et al., Immunity (1998) 8:403-411.

Doolan et al., Immunity (1997) 7:97-112.

Doolan et al., J. Immunol. (2000) 165:1123-1137.

Edgington. "How Sweet It Is: Selection-Mediating Drugs" Biotechnology 10:383-389 (1992).

Eisenlohr et al., J. Exp. Med. (1992) 175:481-487.

Engelhard et al. "Structure of Peptides Associated with MHC Class I Molecules" Curr. Opin. Immunol. 6:13-23 (1994).

Falk et al., J. Exp. Med. (1991) 174:425-434.

Falk et al., "Allele-specific Motifs Revealed by Sequencing of Self-peptide Eluted from MHC Molecules" Nature 351:290-296 (1991).

Feltkamp et al. "Vaccination with Cytotoxic T Lymphocyte Epitope-containing Peptide Protects Against a Tumor Induced by Human Papillomavirus Type 16-transformed Cells" Eur. J. Immunol. 23:2242-2249 (1993).

Foon. "Biological Response Modifiers: the New Immunotherapy" Cancer Res. 49:1621-1639 (1989).

Fynan et al. "DNA Vaccines: Protective Immunizations by Parental, Mucosal, and Gene-gun Inoculations" Proc. Nat'l. Acad. Sci. USA 90:11478-11482 (1993).

Gambacorti-Passerini et al., Clin. Cancer Res. (1997) 3:675-683.

Gaugler et al. "Human Gene MAGE-3 Codes for an Antigen Recognized on a Melanoma by Autologous Cytolytic T Lymphocytes" J. Exp. Med. 179(3):921-930 (1994).

Gavioli et al., Proc. Natl. Acad. Sci. USA (1992) 89:5862-5866.

Gonzalez et al., Parasite Immunology (2000) 22:501-514.

Guo et al., Nature (1992) 360:364-366.

Hayashi et al. "Molecular Cloning and Characterization of the Gene Encoding Mouse Melanoma Antigen by cDNA Library Transfection" J. Immunol. 149:1223-1229 (1992).

Henderson et al. "HLA-A2.1-Associated Peptides form a Mutant Cell Line: A Second Pathway of Antigen Presentation" Science 255:1264-1266 (1992).

Hill et al., Nature (1992) 360:434-439.

Huczko et al., J. Immunol. (1993) 151:2572-2587.

Hunt et al. "Characterization of Peptides Bound to the Class I MHC Molecule HLA-A2.1 by Mass Spectrometry" Science 255:1261-1263 (1992).

Hurtenback et al. "Prevention of Autoimmune Diabetes in Non-Obese Diabetic Mice by Treatment with a Class II Major Histocompatibility Complex-blocking Peptide" J. Exp. Med. 177:1494-1504 (1993).

Ishioka et al. ,J. Immunol. (1999) 162:3915-3925.

Jameson and Bevan, Eur. J. Immunol. (1992) 22:2663-2667.

Jardetzky et al. "Identification of Self Peptides Bound to Purified HLA-B27" Nature 353:326-329 (1991).

Jiang et al. "Role of CD8* T Cells in Murine Experimental Allergic Encephalomyelitis" Science 256:1213-1215 (1992).

Kannagi et al. "Target Epitope in the Tax Protein of Human T-Cell Leukemia Virus Type I Recognized by Class I Major Histocompatibility Complex-Restricted Cytotoxic T Cells" J. of Virol. 66(5):2928-2933 (1992).

Karin et al J. Exp. Med. 180:2227-2237 (1994).

Kast et al., J. Immunol. (1994) 152:3904-3912.

AKst et al., Eur. J. Immunol. (1993) 23:1189-1192.

Kawakami et al., J. Immunol. (1995) 154:3961-3968.

Kawashima et al., "The Multi-Epitope Approach for Immunotherapy for Cancer: Identification of Several CTL Epitopes from Various Tumor-Associated Antigens Expressed on Solid Epithelial Tumors" Human Immunol. (1998) 59:1-14.

Knuth et al. "Cellular and Humoral Immune Responses Against Cancer: Implication for Cancer Vaccines" Curr. Opinion Immunol. 3:659-664 (1991).

Koh et al. "Less Mortality but More Relapses in Experimental Allergic Encephalomyelitis in CDB $^{-/-}$ Mice" Science 256:1210-1213 (1992).

Kozlowski et al., J. Exp. Med. (1992) 175:1417-1422.

Kieger et al. "Single Amino Acid Changes in DR and Antigen Define Residues Critical for Peptide-MHC Binding and T Cell Recognition" J. Immunol. 146:2331-2340 (1991).

Lamonica et al., Hepatology (1999) 30:1088-1098.

Lehniger. "Principles of Biochemistry" Worth Publishers, Inc. NY; pp. 100-101 (1982).

Lipford et al., J. Immunol. (1993) 150:1212-1222.

Lustgarten et al., "Identification of Her-2/Neu CTL Epitopes Using Double Transgenic Mice Expressing HLA-A2.1 and Human CD.8" Human Immunology (1997) 52:109-118.

Maier et al., (1994) 40:306-308.

Maryanski et al. "Competitor Analogs for Defined T Cell Antigens: Peptides Incorporating a Putative Binding Motif and Polyproline or Polyglycine Spacers" Cell 60:63-72 (1990).

Melief et al. "T-Cell Immunotherapy of Cancer" Res. Immunol. 142:425-429 (1991).

Melief et al., Cancer Surveys (1992) 13:81-99.

Miller et al. "Suppressor T Cells Generated by Oral Tolerization to Myelin Basic Protein to Supress Both In Vitro and In Vivo Immune Responses by the Release of Transforming Growth Factor β After Antigen-specific Triggering" Proc. Nat'l. Acad. Sci. USA 89:421-425 (1992).

Morrison et al. "Identification of the Nonamer Peptide from Influenza A Matrix Protein and the Role of Poscketts of HLA-A2 in Its Recognition by Cytotoxic T Lymphocytes" Eur. J. Immunol. 22:903-907 (1992).

Niedermann et al., Immunol. Rev. (1999) 172:29-48.

Niedermann et al., Proc. Natl. Acad. Sci. USA (1996) 93:8572-8577.

Oaks et al. "Molecular Cytogenic Mapping of the Human Melanoma Antigen (MAGE) Gene Family to Chromosome Region Xq27-qtr: Implications for MAGE Immunotherapy" Cancer Res. 54:1627-1629 (1994).

Ochoa-Garay et al. Molecular Immunology 34:273-281 (1997).

Pamer et al. "Precise Prediction of a Dominant Class I MHC-restricted Epitope of Listeria Monocytogenes" Nature 353:852-855 (1991).

Parker et al. "Peptide Binding to HLA-A2 and HLA-B27 Isolated from *Escherichia coli*" J. Biol. Chem. 267(8):5451-5459 (1992).

Parker et al. "Sequence Motifs Important for Peptide Binding to the Human MHC Class I Molecule, HLA-A2" J. Immunol. 149:3580-3587 (1992).

Parker et al. "Scheme for Ranking Potential HLA-A2 Binding Peptides Based on Independent Binding of Individual Peptide Side-Chains" Journal of Immunology 152(1):163-175 (1994).

Paul (ed.), *Fundamental Immunology*, 2$^{nd}$ ed., Raven Press, NY, pp. 473-487 (1989).

Paul (ed.), *Fundamental Immunology*, 3$^{rd}$ ed., Raven Press, NY, pp. 976-978 (1993).

Preisler-Adams et al. "Complete Nucleotide Sequence of a Hepatitis B Virus, Subtype adw2, and Identification of Three Types of C Open Reading Frames" Nucleic Acids Res. 21:2258 (1993).

Prezzi et al., Eur. J. Immunol. (2001) 31:894-906

Rammensee et al. "Peptides Naturally Presented by MHC Class I Molecules" Annu. Rev. Immunol. 11:213-244 (1993).

Rammensee et al. "MHC Ligands and Peptide Motifs: First Listing" Immunogenetics 41(4):178-228 (1995).

Rammensee et al. "SYFPEITHI: Database for MHC Ligands and Peptide Motifs" Immunogenetics 50(3-4):213-219 (1999).

Rehermann et al., J. Clin. Invest. (1996) 97:1655-1665.

Ressing et al. Human CTL Epitopes Encoded by Human Papillomavirus Type 16 E6 and E7 Identified Through In Vivo and In Vitro Immunogenicity Studies of HLA-A*0201-Binding Peptides J. Immunol. 154:5934 (1995).

Rickinson. "Immune Intervention Against Virus-associated Human Cancers" Annals of Oncology 6(Supp. 1): 69-71 (1995).

Rivoltini et al., J. Immunol. (1995) 154:2257-2265.

Romero et al. "H-2Kd-restricted Antigenic Peptides Share a Simple Binding Motif" J. Exp. Med. 174:603-612 (1991).

Rothbard, Current Opinion in Immunology (1989) 2:99-105.

Rotzschke et al. "Characterization of Naturally Occuring Minor Histocompatibitlity Peptides Including H-4 and H-Y" 249:283-287 (1990).

Rotzschke et al. "Isolation and Analysis of Naturally Processed Viral Peptides As Recognized by Cytotoxic T Cells" Nature 348:252-254 (1990).

Rotzschke et al. "Naturally Occuring Peptide Antigens Derived from the MHC Class-I-restricted Processing Pathway" Immunology Today 12(12):447-455(1991).

Rotzschke et al. "Peptide Motifs of Closely Related HLA Class I Molecules Encompass Substantial Differences" Eur. J. Immunol. 22:2453-2456 (1992).

Rudinger. "Characteristics of the Amino Acids As Components of Peptide Hormone Sequence" in *Peptide Hormones*, Parsons (ed.), University Park Press, pp. 1-7 (1976).

Ruppert et al. "Prominent Role of Secondary Anchor Residues in Peptide Binding to HLA-A2.1 Molucules" Cell 74(5):929-937 (1993).

Sarobe et al. "Induction of Antibodies Against a Peptide Hapten Does Not Require Covalent Linkage Between the Hapten and Class II Presentable T Helper Peptide" Eur. J. Immunol. 21:1555-1558 (1991).

Schaeffer et al. Proc. Natl. Acad. Sci. USA 86:4649 (1989).

Scognamiglio et al., J. Immumol. (1999) 162:6681-6689.

Sette et al. "Prediction of Major Histocompatibility Complex Binding Regions by Sequence Pattern Analysis" Proc. Nat'l. Acad. Sci. USA 86:3296-3300 (1989).

Sette et al. "Random Association between the Peptide Repertoire of A2.1 Class I and Several Different DR Class II Molecules" J. Immunol. 147:3893-3900 (1991).

Sette et al., J. Immunol. (1994) 153:5586-5592.

Sette and Sidney, Curr. Opin. Immunol. (1998) 10:478-482.

Sette et al., in Persistent Viral Infections, Ahmed and Chen (Eds.), John Wiley & Sons (1999).

Sette et al. Immunodominance and Breadth of Cellular Responses (2001) In Press.

Shanker et al. "Three Regions of HIV-1 gp160 Contain Clusters of Immunodominant CTL Epitopes" (Abstracr) Immunology Letters 52(1):23-30 (1996).

Shastri et al., J. Immunol. (1995) 155:4339-4346.

Sherman et al., J. Exp. Med. (1992) 175:1221-1226.

Shimojo et al. "Specificity of Peptide Binding by the HLA-A2.1 Molecule" J. Immunol. 143(9):2939-2947 (1989).

Slingluff et al. "Recognition of Human Melanoma Cells by the HLA-A2.1-restricted Cytotoxic T Lymphocytes Is Mediated by At Least Six Shared Peptide Epitopes" J. Immunol. 150:2955-2960 (1993).

Snoke et al., J. Immunol. (1993) 151:6815-6821.

Storkus et al. "Identification of Human Melanoma Peptides Recognized by Class I Restricted Tumor Infiltrating T Lymphocytes" J. Immunol. 151:3719-3727 (1993).

Tangri et al., Journal of Experimental Medicine (2001) In Press.

Threlkeld et al., . Immunol. (1997) 159:1648-1657.

Traversari et al. "A Nonapeptide Encoded by Human Gene MAGE-1 Is Recognized on HLA-A1 by Cytolytic T Lymphocytes Directed Against Tumor Antigen MZ2-E" J. Exp. Med. 176:1453-1457 (1992).

Tsai et al., J. Immunol. (1997) 1796-1802.

Urban et al. "Autoimmune T Cells: Immune Recognition of Normal and Variant Peptide Epitopes and Peptide-Based Therapy" Cell 59:257-271 (1989).

Van der Bruggen et al. "A Gene Encoding an Antigen Recognized by Cytolytic T Lymphocytes on a Human Melanoma" Science 254:1643-1647 (1991).

Van Der Most et al., J. Immunol. (1996) 157:5543-5554.

Van Der Most et al., Virology (1997) 71:5110-5114.

Van Der Most et al., Virology (1998) 240:158-167.

Virect et al. "Recognition of Shared Melanoma Antigen By HLA-A2 Restricted Cytolytic T Cell Clones Derived from Human Tumor-infiltrating Lymphocytes" Eur. J. Immunol. (1993).

Vitiello et al. "Development of a Lipopetide Based Therapeutic Vaccine to Treat Chronic HBV Infection" J. Clin Invest. 95:341-349 (1995).

Vitiello et al., J. Immunol (1996) 157:5555-5562.

Wei et al. "HLA-A2 Molecules in an Antigen-Processing Mutant Cell Contain Signal Sequencederived Peptides" Nature 356:443-446 (1992).

Wentworth et al., Eur. J. Immunol. (1996) 26:97-101.

Weynants et al. "Expression of MAGE Genes by Non-Small-Cell Lung Carcinomas" Int. J. Cancer 56:826-829 (1994).

Wilson et al., J. Virol. (2001) 75:4195-4207.

Wizel et al., J. Clin. Invest. (1998) 102:1062-1071.

Wraith et al. "Antigen Recognition in Autoimmune Encephalomyelitis and the Potential for Peptide-Mediated Immunotherapy" Cell 59:247-255 (1989).

Wysocka et al. "Class I H-2d-Restricted Cytotoxic T Lymphocytes Recongnize the Neuraminidase Glycoprotein of Influenza Virus Subtype N1" Journal of Virology 64(3):1028-1032 (1990).

Yewdell and Bennick, Annu. Rev. Immunol. (1999) 17:51-88.

Yoon et al., Virus Research (1998) 54:23-29.

York and Rock, Annu. Rev. Immunol. (1996) 14:369-396.

Zakut et al, "Differential Expression of MAGE-1, -2, and -3 Messenger RNA in Transformed and Normal Human Cell Lines" Cancer Res. 53:5-8 (1993).

Zhang et al., Proc. Natl. Acad. Sci. USA (1993) 90(6):2217-2221.

\* cited by examiner

HLA BINDING PEPTIDES AND THEIR USES

REFERENCE TO RELATED APPLICATIONS

This application is a continuation-in-part of U.S. application Ser. No. 09/098,584, filed Jun. 17, 1998, now abandoned.

REFERENCE TO A SEQUENCE LISTING AND TABLES SUBMITTED ON A COMPACT DISC

The Substitute Sequence Listing written in file Sequence Listing.txt, 92,000 bytes, created on Jun. 22, 2005 on compact disc for application Ser. No. 09/189,702, Sette et al., HLA Binding Peptides and Their Uses, is herein incorporated-by-reference.

BACKGROUND OF THE INVENTION

The present invention relates to compositions and methods for preventing, treating or diagnosing a number of pathological states such as viral diseases and cancers. In particular, it provides novel peptides capable of binding selected major histocompatibility complex (MHC) molecules and inducing an immune response.

MHC molecules are classified as either Class I or Class II molecules. Class II MHC molecules are expressed primarily on cells involved in initiating and sustaining immune responses, such as T lymphocytes, B lymphocytes, macrophages, etc. Class II MHC molecules are recognized by helper T lymphocytes and induce proliferation of helper T lymphocytes and amplification of the immune response to the particular immunogenic peptide that is displayed. Class I MHC molecules are expressed on almost all nucleated cells and are recognized by cytotoxic T lymphocytes (CTLs), which then destroy the antigen-bearing cells. CTLs are particularly important in tumor rejection and in fighting viral infections.

The CTL recognizes the antigen in the form of a peptide fragment bound to the MHC class I molecules rather than the intact foreign antigen itself. The antigen must normally be endogenously synthesized by the cell, and a portion of the protein antigen is degraded into small peptide fragments in the cytoplasm. Some of these small peptides translocate into a pre-Golgi compartment and interact with class I heavy chains to facilitate proper folding and association with the subunit β2 microglobulin. The peptide-MHC class I complex is then routed to the cell surface for expression and potential recognition by specific CTLs.

Investigations of the crystal structure of the human MHC class I molecule, HLA-A2.1, indicate that a peptide binding groove is created by the folding of the α1 and α2 domains of the class I heavy chain (Bjorkman et al., Nature 329:506 (1987). In these investigations, however, the identity of peptides bound to the groove was not determined.

Buus et al., Science 242:1065 (1988) first described a method for acid elution of bound peptides from MHC. Subsequently, Rammensee and his coworkers (Falk et al., Nature 351:290 (1991) have developed an approach to characterize naturally processed peptides bound to class I molecules. Other investigators have successfully achieved direct amino acid sequencing of the more abundant peptides in various HPLC fractions by conventional automated sequencing of peptides eluted from class I molecules of the B type (Jardetzky, et al., Nature 353:326 (1991) and of the A2.1 type by mass spectrometry (Hunt, et al., Science 225:1261 (1992). A review of the characterization of naturally processed peptides in MHC Class I has been presented by Rötzschke and Falk (Rötzschke and Falk, Immunol. Today 12:447 (1991).

Sette et al., Proc. Natl. Acad. Sci. USA 86:3296 (1989) showed that MHC allele specific motifs could be used to predict MHC binding capacity. Schaeffer et al., Proc. Natl. Acad. Sci. USA 86:4649 (1989) showed that MHC binding was related to immunogenicity. Several authors (De Bruijn et al., Eur. J. Immunol., 21:2963-2970 (1991); Pamer et al., 991 Nature 353:852-955 (1991)) have provided preliminary evidence that class I binding motifs can be applied to the identification of potential immunogenic peptides in animal models. Class I motifs specific for a number of human alleles of a given class I isotype have yet to be described. It is desirable that the combined frequencies of these different alleles should be high enough to cover a large fraction or perhaps the majority of the human outbred population.

Despite the developments in the art, the prior art has yet to provide a useful human peptide-based vaccine or therapeutic agent based on this work. The present invention provides these and other advantages.

SUMMARY OF THE INVENTION

The present invention provides compositions comprising immunogenic peptides having binding motifs for HLA-A2.1 molecules. The immunogenic peptides, which bind to the appropriate MHC allele, are preferably 9 to 10 residues in length and comprise conserved residues at certain positions such as positions 2 and 9. Moreover, the peptides do not comprise negative binding residues as defined herein at other positions such as positions 1, 3, 6 and/or 7 in the case of peptides 9 amino acids in length and positions 1, 3, 4, 5, 7, 8 and/or 9 in the case of peptides 10 amino acids in length. The present invention defines positions within a motif enabling the selection of peptides which will bind efficiently to HLA A2.1.

The motifs of the inventions include peptide of 9 amino acids which have a first conserved residue at the second position from the N-terminus selected from the group consisting of I, V, A and T and a second conserved residue at the C-terminal position selected from the group consisting of V, L, I, A and M. Alternatively, the peptide may have a first conserved residue at the second position from the N-terminus selected from the group consisting of L, M, I, V, A and T; and a second conserved residue at the C-terminal position selected from the group consisting of A and M. If the peptide has 10 residues it will contain a first conserved residue at the second position from the N-terminus selected from the group consisting of L, M, I, V, A, and T; and a second conserved residue at the C-terminal position selected from the group consisting of V, I, L, A and M; wherein the first and second conserved residues are separated by 7 residues.

Epitopes on a number of immunogenic target proteins can be identified using the peptides of the invention. Examples of suitable antigens include prostate cancer specific antigen (PSA), prostate specific membrane antigen (PSM), hepatitis B core and surface antigens (HBVc, HBVs) hepatitis C antigens, Epstein-Barr virus antigens, human immunodeficiency type-1 virus (HIV1), Kaposi's sarcoma herpes virus (KSHV), human papilloma virus (HPV) antigens, Lassa virus, mycobacterium tuberculosis (MT), p53 and murine p53 (mp53), CEA, trypanosome surface antigen (TSA), members of the tyrosinas related protein (TRP) families, and Her2/neu. The peptides are thus useful in pharmaceutical compositions for both in vivo and ex vivo therapeutic and diagnostic applications.

The present invention also provides compositions comprising immunogenic peptides having binding motifs for MHC Class I molecules. The immunogenic peptides are typically between about 8 and about 11 residues and comprise conserved residues involved in binding proteins encoded by the appropriate MHC allele. A number of allele specific motifs have been identified.

For instance, the motif for HLA-A3.2 comprises from the N-terminus to C-terminus a first conserved residue of L, M, I, V, S, A, T and F at position 2 and a second conserved residue of K, R or Y at the C-terminal end. Other first conserved residues are C, G or D and alternatively E. Other second conserved residues are H or F. The first and second conserved residues are preferably separated by 6 to 7 residues.

The motif for HLA-A1 comprises from the N-terminus to the C-terminus a first conserved residue of T, S or M, a second conserved residue of D or E, and a third conserved residue of Y. Other second conserved residues are A, S or T. The first and second conserved residues are adjacent and are preferably separated from the third conserved residue by 6 to 7 residues. A second motif consists of a first conserved residue of E or D and a second conserved residue of Y where the first and second conserved residues are separated by 5 to 6 residues.

The motif for HLA-A11 comprises from the N-terminus to the C-terminus a first conserved residue of T, V, M, L, I, S, A, G, N, C D, or F at position 2 and a C-terminal conserved residue of K, R, Y or H. The first and second conserved residues are preferably separated by 6 or 7 residues.

The motif for HLA-A24.1 comprises from the N-terminus to the C-terminus a first conserved residue of Y, F or W at position 2 and a C terminal conserved residue of F, I, W, M or L. The first and second conserved residues are preferably separated by 6 to 7 residues.

Epitopes on a number of potential target proteins can be identified in this manner. Examples of suitable antigens include prostate specific antigen (PSA), prostate specific membrane antigen (PSM), hepatitis B core and surface antigens (HBVc, HBVs) hepatitis C antigens, malignant melanoma antigen (MAGE-1) Epstein-Barr virus antigens, human immunodeficiency type-1 virus (HIV1), papilloma virus antigens, Lassa virus, *mycobacterium tuberculosis* (MT), p53 and murine p53 (mp53), CEA, and Her2/neu, and members of the tyrosinase related protein (TRP) families. The peptides are thus useful in pharmaceutical compositions for both in vivo and ex vivo therapeutic and diagnostic applications.

The present invention also provides compositions comprising immunogenic peptides having binding motifs for non-A HLA alleles. The immunogenic peptides are preferably about 9 to 10 residues in length and comprise conserved residues at certain positions such as proline at position 2 and an aromatic residue (e.g., Y, W, F) or hydrophobic residue (e.g., L, I, V, M, or A) at the carboxy terminus. In particular, an advantage of the peptides of the invention is their ability to bind to two or more different HLA alleles.

Epitopes on a number of potential target proteins can be identified in this manner. Examples of suitable antigens include prostate specific antigen (PSA), hepatitis B core and surface antigens (HBVc, HBVs) hepatitis C antigens, malignant melanoma antigen (MAGE-1) Epstein-Barr virus antigens, human immunodeficiency type-1 virus (HIV1), papilloma virus antigens, Lassa virus, *mycobacterium tuberculosis* (MT), p53, CEA, and Her2/neu. The peptides are thus useful in pharmaceutical compositions for both in vivo and ex vivo therapeutic and diagnostic applications.

DEFINITIONS

The term "peptide" is used interchangeably with "oligopeptide" in the present specification to designate a series of residues, typically L-amino acids, connected one to the other typically by peptide bonds between the alpha-amino and carbonyl groups of adjacent amino acids. The oligopeptides of the invention are less than about 15 residues in length and usually consist of between about 8 and about 11 residues, preferably 9 or 10 residues.

An "immunogenic peptide" is a peptide which comprises an allele-specific motif such that the peptide will bind an MHC molecule and induce a CTL response. Immunogenic peptides of the invention are capable of binding to an appropriate HLA-A2.1 molecule and inducing a cytotoxic T cell response against the antigen from which the immunogenic peptide is derived.

Immunogenic peptides are conveniently identified using the algorithms of the invention. The algorithms are mathematical procedures that produce a score which enables the selection of immunogenic peptides. Typically one uses the algorithmic score with a "binding threshold" to enable selection of peptides that have a high probability of binding at a certain affinity and will in turn be immunogenic. The algorithm is based upon either the effects on MHC binding of a particular amino acid at a particular position of a peptide or the effects on binding of a particular substitution in a motif containing peptide.

A "conserved residue" is an amino acid which occurs in a significantly higher frequency than would be expected by random distribution at a particular position in a peptide. Typically a conserved residue is one where the MHC structure may provide a contact point with the immunogenic peptide. At least one to three or more, preferably two, conserved residues within a peptide of defined length defines a motif for an immunogenic peptide. These residues are typically in close contact with the peptide binding groove, with their side chains buried in specific pockets of the groove itself. Typically, an immunogenic peptide will comprise up to three conserved residues, more usually two conserved residues.

As used herein, "negative binding residues" are amino acids which if present at certain positions (for example, positions 1, 3 and/or 7 of a 9-mer) will result in a peptide being a nonbinder or poor binder and in turn fail to be immunogenic i.e. induce a CTL response.

The term "motif" refers to the pattern of residues in a peptide of defined length, usually about 8 to about 11 amino acids, which is recognized by a particular MHC allele. The peptide motifs are typically different for each human MHC allele and differ in the pattern of the highly conserved residues and negative residues.

The binding motif for an allele can be defined with increasing degrees of precision. In one case, all of the conserved residues are present in the correct positions in a peptide and there are no negative residues in positions 1, 3 and/or 7.

The phrases "isolated" or "biologically pure" refer to material which is substantially or essentially free from components which normally accompany it as found in its native state. Thus, the peptides of this invention do not contain materials normally associated with their in situ environment, e.g., MHC I molecules on antigen presenting cells. Even where a protein has been isolated to a homogenous or dominant band, there are trace contaminants in the range of 5-10% of native protein which co-purify with the desired protein. Isolated peptides of this invention do not contain such endogenous co-purified protein.

The term "residue" refers to an amino acid or amino acid mimetic incorporated in an oligopeptide by an amide bond or amide bond mimetic.

DESCRIPTION OF THE PREFERRED EMBODIMENTS

I. HLA-A2.1 Motif

The present invention relates to the determination of allele-specific peptide motifs for human Class I MHC (sometimes referred to as HLA) allele subtypes, in particular, peptide motifs recognized by HLA-A2.1 alleles. These motifs are then used to define T cell epitopes from any desired antigen, particularly those associated with human viral diseases, cancers or autoimmune diseases, for which the amino acid sequence of the potential antigen or autoantigen targets is known.

Epitopes on a number of potential target proteins can be identified in this manner. Examples of suitable antigens include prostate specific antigen (PSA), hepatitis B core and surface antigens (HBVc, HBVs) hepatitis C antigens, Epstein-Barr virus antigens, melanoma antigens (e.g., MAGE-1), human immunodeficiency virus (HIV) antigens, human papilloma virus (HPV) antigens, Lassa virus, *mycobacterium tuberculosis* (MT), p53, CEA, trypanosome surface antigen (TSA) and Her2/neu.

Peptides comprising the epitopes from these antigens are synthesized and then tested for their ability to bind to the appropriate MHC molecules in assays using, for example, purified class I molecules and radioiodonated peptides and/or cells expressing empty class I molecules by, for instance, immunofluorescent staining and flow microfluorometry, peptide-dependent class I assembly assays, and inhibition of CTL recognition by peptide competition. Those peptides that bind to the class I molecule are further evaluated for their ability to serve as targets for CTLs derived from infected or immunized individuals, as well as for their capacity to induce primary in vitro or in vivo CTL responses that can give rise to CTL populations capable of reacting with virally infected target cells or tumor cells as potential therapeutic agents.

The MHC class I antigens are encoded by the HLA-A, B, and C loci. HLA-A and B antigens are expressed at the cell surface at approximately equal densities, whereas the expression of HLA-C is significantly lower (perhaps as much as 10-fold lower). Each of these loci have a number of alleles. The peptide binding motifs of the invention are relatively specific for each allelic subtype.

For peptide-based vaccines, the peptides of the present invention preferably comprise a motif recognized by an MHC I molecule having a wide distribution in the human population. Since the MHC alleles occur at different frequencies within different ethnic groups and races, the choice of target MHC allele may depend upon the target population. Table 1 shows the frequency of various alleles at the HLA-A locus products among different races. For instance, the majority of the Caucasoid population can be covered by peptides which bind to four HLA-A allele subtypes, specifically HLA-A2.1, A1, A3.2, and A24.1. Similarly, the majority of the Asian population is encompassed with the addition of peptides binding to a fifth allele HLA-A11.2.

TABLE 1

| A Allele/Subtype | N(69)* | A(54) | C(502) |
|---|---|---|---|
| A1 | 10.1(7) | 1.8(1) | 27.4(138) |
| A2.1 | 11.5(8) | 37.0(20) | 39.8(199) |
| A2.2 | 10.1(7) | 0 | 3.3(17) |
| A2.3 | 1.4(1) | 5.5(3) | 0.8(4) |
| A2.4 | — | — | — |
| A2.5 | — | — | — |
| A3.1 | 1.4(1) | 0 | 0.2(0) |
| A3.2 | 5.7(4) | 5.5(3) | 21.5(108) |
| A11.1 | 0 | 5.5(3) | 0 |
| A11.2 | 5.7(4) | 31.4(17) | 8.7(44) |
| A11.3 | 0 | 3.7(2) | 0 |
| A23 | 4.3(3) | — | 3.9(20) |
| A24 | 2.9(2) | 27.7(15) | 15.3(77) |
| A24.2 | — | — | — |
| A24.3 | — | — | — |
| A25 | 1.4(1) | — | 6.9(35) |
| A26.1 | 4.3(3) | 9.2(5) | 5.9(30) |
| A26.2 | 7.2(5) | — | 1.0(5) |
| A26V | — | 3.7(2) | — |
| A28.1 | 10.1(7) | — | 1.6(8) |
| A28.2 | 1.4(1) | — | 7.5(38) |
| A29.1 | 1.4(1) | — | 1.4(7) |
| A29.2 | 10.1(7) | 1.8(1) | 5.3(27) |
| A30.1 | 8.6(6) | — | 4.9(25) |
| A30.2 | 1.4(1) | — | 0.2(1) |
| A30.3 | 7.2(5) | — | 3.9(20) |
| A31 | 4.3(3) | 7.4(4) | 6.9(35) |
| A32 | 2.8(2) | — | 7.1(36) |
| Aw33.1 | 8.6(6) | — | 2.5(13) |
| Aw33.2 | 2.8(2) | 16.6(9) | 1.2(6) |
| Aw34.1 | 1.4(1) | — | — |
| Aw34.2 | 14.5(10) | — | 0.8(4) |
| Aw36 | 5.9(4) | — | |

Table compiled from B. DuPont, Immunobiology of HLA, Vol. I, Histocompatibility Testing 1987, Springer-Verlag, New York 1989.
*N - negroid; A = Asian; C = Caucasoid. Numbers in parenthesis represent the number of individuals included in the analysis.

The nomenclature used to describe peptide compounds follows the conventional practice wherein the amino group is presented to the left (the N-terminus) and the carboxyl group to the right (the C-terminus) of each amino acid residue. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G.

The procedures used to identify peptides of the present invention generally follow the methods disclosed in Falk et al., Nature 351:290 (1991), which is incorporated herein by reference. Briefly, the methods involve large-scale isolation of MHC class I molecules, typically by immunoprecipitation or affinity chromatography, from the appropriate cell or cell line. Examples of other methods for isolation of the desired MHC molecule equally well known to the artisan include ion exchange chromatography, lectin chromatography, size exclusion, high performance ligand chromatography, and a combination of all of the above techniques.

In the typical case, immunoprecipitation is used to isolate the desired allele. A number of protocols can be used, depending upon the specificity of the antibodies used. For example, allele-specific mAb reagents can be used for the affinity purification of the HLA-A, HLA-B1, and HLA-C molecules. Several mAb reagents for the isolation of HLA-A molecules are available. The monoclonal BB7.2 is suitable for isolating HLA-A2 molecules. Affinity columns prepared with these mAbs using standard techniques are successfully used to purify the respective HLA-A allele products.

In addition to allele-specific mAbs, broadly reactive anti-HLA-A, B, C mAbs, such as W6/32 and B9.12.1, and one anti-HLA-B, C mAb, B1.23.2, could be used in alternative affinity purification protocols as described in previous applications.

The peptides bound to the peptide binding groove of the isolated MHC molecules are eluted typically using acid treatment. Peptides can also be dissociated from class I molecules by a variety of standard denaturing means, such as heat, pH, detergents, salts, chaotropic agents, or a combination thereof.

Peptide fractions are further separated from the MHC molecules by reversed-phase high performance liquid chromatography (HPLC) and sequenced. Peptides can be separated by a variety of other standard means well known to the artisan, including filtration, ultrafiltration, electrophoresis, size chromatography, precipitation with specific antibodies, ion exchange chromatography, isoelectrofocusing, and the like.

Sequencing of the isolated peptides can be performed according to standard techniques such as Edman degradation (Hunkapiller, M. W., et al., *Methods Enzymol.* 91, 399 [1983]). Other methods suitable for sequencing include mass spectrometry sequencing of individual peptides as previously described (Hunt, et al., *Science* 225:1261 (1992), which is incorporated herein by reference). Amino acid sequencing of bulk heterogenous peptides (e.g., pooled HPLC fractions) from different class I molecules typically reveals a characteristic sequence motif for each class I allele.

Definition of motifs specific for different class I alleles allows the identification of potential peptide epitopes from an antigenic protein whose amino acid sequence is known. Typically, identification of potential peptide epitopes is initially carried out using a computer to scan the amino acid sequence of a desired antigen for the presence of motifs. The epitopic sequences are then synthesized. The capacity to bind MHC Class molecules is measured in a variety of different ways. One means is a Class I molecule binding assay as described in the related applications, noted above. Other alternatives described in the literature include inhibition of antigen presentation (Sette, et al., *J. Immunol.* 141:3893 (1991), in vitro assembly assays (Townsend, et al., *Cell* 62:285 (1990), and FACS based assays using mutated cells, such as RMA.S (Melief, et al., *Eur. J. Immunol.* 21:2963 (1991)).

Next, peptides that test positive in the MHC class I binding assay are assayed for the ability of the peptides to induce specific CTL responses in vitro. For instance, antigen-presenting cells that have been incubated with a peptide can be assayed for the ability to induce CTL responses in responder cell populations. Antigen-presenting cells can be normal cells such as peripheral blood mononuclear cells or dendritic cells (Inaba, et al., *J. Exp. Med.* 166:182 (1987); Boog, *Eur. J. Immunol.* 18:219 [1988]).

Alternatively, mutant mammalian cell lines that are deficient in their ability to load class I molecules with internally processed peptides, such as the mouse cell lines RMA-S (Kärre, et al. *Nature*, 319:675 (1986); Ljunggren, et al., *Eur. J. Immunol.* 21:2963-2970 (1991)), and the human somatic T cell hybrid, T-2 (Cerundolo, et al., Nature 345:449-452 (1990)) and which have been transfected with the appropriate human class I genes are conveniently used, when peptide is added to them, to test for the capacity of the peptide to induce in vitro primary CTL responses. Other eukaryotic cell lines which could be used include various insect cell lines such as mosquito larvae (ATCC cell lines CCL 125, 126, 1660, 1591, 6585, 6586), silkworm (ATTC CRL 8851), armyworm (ATCC CRL 1711), moth (ATCC CCL 80) and *Drosophila* cell lines such as a Schneider cell line (see Schneider *J. Embryol. Exp. Morphol.* 27:353-365 [1927]).

Peripheral blood lymphocytes are conveniently isolated following simple venipuncture or leukopheresis of normal donors or patients and used as the responder cell sources of CTL precursors. In one embodiment, the appropriate antigen-presenting cells are incubated with 10-100 μM of peptide in serum-free media for 4 hours under appropriate culture conditions. The peptide-loaded antigen-presenting cells are then incubated with the responder cell populations in vitro for 7 to 10 days under optimized culture conditions. Positive CTL activation can be determined by assaying the cultures for the presence of CTLs that kill radiolabeled target cells, both specific peptide-pulsed targets as well as target cells expressing the endogenously processed form of the relevant virus or tumor antigen from which the peptide sequence was derived.

Specificity and MHC restriction of the CTL is determined by testing against different peptide target cells expressing appropriate or inappropriate human MHC class I. The peptides that test positive in the MHC binding assays and give rise to specific CTL responses are referred to herein as immunogenic peptides.

The immunogenic peptides can be prepared synthetically, or by recombinant DNA technology or from natural sources such as whole viruses or tumors. Although the peptide will preferably be substantially free of other naturally occurring host cell proteins and fragments thereof, in some embodiments the peptides can be synthetically conjugated to native fragments or particles.

The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. When possible, it may be desirable to optimize peptides of the invention to a length of 9 or 10 amino acid residues, commensurate in size with endogenously processed viral peptides or tumor cell peptides that are bound to MHC class I molecules on the cell surface.

Peptides having the desired activity may be modified as necessary to provide certain desired attributes, e.g., improved pharmacological characteristics, while increasing or at least retaining substantially all of the biological activity of the unmodified peptide to bind the desired MHC molecule and activate the appropriate T cell. For instance, the peptides may be subject to various changes, such as substitutions, either conservative or non-conservative, where such changes might provide for certain advantages in their use, such as improved MHC binding. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg;

and Phe, Tyr. The effect of single amino acid substitutions may also be probed using D-amino acids. Such modifications may be made using well known peptide synthesis procedures, as described in e.g., Merrifield, *Science* 232: 341-347 (1986), Barany and Merrifield, *The Peptides*, Gross and Meienhofer, eds. (N.Y., Academic Press), pp. 1-284 (1979); and Stewart and Young, *Solid Phase Peptide Synthesis*, (Rockford, Ill., Pierce), 2d Ed. (1984), incorporated by reference herein.

The peptides can also be modified by extending or decreasing the compound's amino acid sequence, e.g., by the addition or deletion of amino acids. The peptides or analogs of the invention can also be modified by altering the order or composition of certain residues, it being readily appreciated that certain amino acid residues essential for biological activity, e.g., those at critical contact sites or conserved residues, may generally not be altered without an adverse effect on biological activity. The non-critical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

Typically, a series of peptides with single amino acid substitutions are employed to determine the effect of electrostatic charge, hydrophobicity, etc. on binding. For instance, a series of positively charged (e.g., Lys or Arg) or negatively charged (e.g., Glu) amino acid substitutions are made along the length of the peptide revealing different patterns of sensitivity towards various MHC molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding.

Amino acid substitutions are typically of single residues. Substitutions, deletions, insertions or any combination thereof may be combined to arrive at a final peptide. Substitutional variants are those in which at least one residue of a peptide has been removed and a different residue inserted in its place. Such substitutions generally are made in accordance with the following Table 2 when it is desired to finely modulate the characteristics of the peptide.

TABLE 2

| Original Residue | Exemplary Substitution |
| --- | --- |
| Ala | Ser |
| Arg | Lys, His |
| Asn | Gln |
| Asp | Glu |
| Cys | Ser |
| Gln | Asn |
| Glu | Asp |
| Gly | Pro |
| His | Lys; Arg |
| Ile | Leu; Val |
| Leu | Ile; Val |
| Lys | Arg; His |

TABLE 2-continued

| Original Residue | Exemplary Substitution |
| --- | --- |
| Met | Leu; Ile |
| Phe | Tyr; Trp |
| Ser | Thr |
| Thr | Ser |
| Trp | Tyr; Phe |
| Tyr | Trp; Phe |
| Val | Ile; Leu |
| Pro | Gly |

Substantial changes in function (e.g., affinity for MHC molecules or T cell receptors) are made by selecting substitutions that are less conservative than those in Table 2, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in peptide properties will be those in which (a) hydrophilic residue, e.g. seryl, is substituted for (or by) a hydrophobic residue, e.g. leucyl, isoleucyl, phenylalanyl, valyl or alanyl; (b) a residue having an electropositive side chain, e.g., lysl, arginyl, or histidyl, is substituted for (or by) an electronegative residue, e.g. glutamyl or aspartyl; or (c) a residue having a bulky side chain, e.g. phenylalanine, is substituted for (or by) one not having a side chain, e.g., glycine.

The peptides may also comprise isosteres of two or more residues in the immunogenic peptide. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, peptides and Proteins*, Vol. VII (Weinstein ed., 1983).

Modifications of peptides with various amino acid mimetics or unnatural amino acids are particularly useful in increasing the stability of the peptide in vivo. Stability can be assayed in a number of ways. For instance, peptidases and various biological media, such as human plasma and serum, have been used to test stability. See, e.g., Verhoef et al., *Eur. J. Drug Metab. Pharmacokin.* 11:291-302 (1986). Half life of the peptides of the present invention is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

The peptides of the present invention or analogs thereof which have CTL stimulating activity may be modified to provide desired attributes other than improved serum half life. For instance, the ability of the peptides to induce CTL activity can be enhanced by linkage to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the CTL peptide may be linked to the T helper peptide without a spacer.

The immunogenic peptide may be linked to the T helper peptide either directly or via a spacer either at the amino or carboxy terminus of the CTL peptide. The amino terminus of either the immunogenic peptide or the T helper peptide may be acylated. Exemplary T helper peptides include tetanus toxoid 830-843, influenza 307-319, malaria circumsporozoite 382-398 and 378-389.

In some embodiments it may be desirable to include in the pharmaceutical compositions of the invention at least one component which primes CTL. Lipids have been identified as agents capable of priming CTL in vivo against viral antigens. For example, palmitic acid residues can be attached to the alpha and epsilon amino groups of a Lys residue and then linked, e.g., via one or more linking residues such as Gly, Gly-Gly-, Ser, Ser-Ser, or the like, to an immunogenic peptide. The lipidated peptide can then be injected directly in a micellar form, incorporated into a liposome or emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of the immunogenic peptide.

As another example of lipid priming of CTL responses, $E.$ $coli$ lipoproteins, such as tripalmitoyl-S-glycerylcysteinlyseryl-serine ($P_3CSS$) can be used to prime virus specific CTL when covalently attached to an appropriate peptide. See, Deres et al., $Nature$ 342:561-564 (1989), incorporated herein by reference. Peptides of the invention can be coupled to $P_3CSS$, for example, and the lipopeptide administered to an individual to specifically prime a CTL response to the target antigen. Further, as the induction of neutralizing antibodies can also be primed with $P_3CSS$ conjugated to a peptide which displays an appropriate epitope, the two compositions can be combined to more effectively elicit both humoral and cell-mediated responses to infection.

In addition, additional amino acids can be added to the termini of a peptide to provide for ease of linking peptides one to another, for coupling to a carrier support, or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide. Modification at the C terminus in some cases may alter binding characteristics of the peptide. In addition, the peptide or oligopeptide sequences can differ from the natural sequence by being modified by terminal-$NH_2$ acylation, e.g., by alkanoyl ($C_1$-$C_{20}$) or thioglycolyl acetylation, terminal-carboxylamidation, e.g., ammonia, methylamine, etc. In some instances these modifications may provide sites for linking to a support or other molecule.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, $Solid$ $Phase$ $Peptide$ $Synthesis,$ 2d. ed., Pierce Chemical Co. (1984), supra.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., $Molecular$ $Cloning,$ $A$ $Laboratory$ $Manual,$ Cold Spring Harbor Press, Cold Spring Harbor, N.Y. (1982), which is incorporated herein by reference. Thus, fusion proteins which comprise one or more peptide sequences of the invention can be used to present the appropriate T cell epitope.

As the coding sequence for peptides of the length contemplated herein can be synthesized by chemical techniques, for example, the phosphotriester method of Matteucci et al., $J.$ $Am.$ $Chem.$ $Soc.$ 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

The peptides of the present invention and pharmaceutical and vaccine compositions thereof are useful for administration to mammals, particularly humans, to treat and/or prevent viral infection and cancer. Examples of diseases which can be treated using the immunogenic peptides of the invention include prostate cancer, hepatitis B, hepatitis C, AIDS, renal carcinoma, cervical carcinoma, lymphoma, CMV and condyloma acuminatum.

For pharmaceutical compositions, the immunogenic peptides of the invention are administered to an individual already suffering from cancer or infected with the virus of interest. Those in the incubation phase or the acute phase of infection can be treated with the immunogenic peptides separately or in conjunction with other treatments, as appropriate. In therapeutic applications, compositions are administered to a patient in an amount sufficient to elicit an effective CTL response to the virus or tumor antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 5000 µg of peptide for a 70 kg patient, followed by boosting dosages of from about 1.0 µg to about 1000 µg of peptide pursuant to a boosting regimen over weeks to months depending upon the patient's response and condition by measuring specific CTL activity in the patient's blood. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

For therapeutic use, administration should begin at the first sign of viral infection or the detection or surgical removal of tumors or shortly after diagnosis in the case of acute infection. This is followed by boosting doses until at least symptoms are substantially abated and for a period thereafter. In chronic infection, loading doses followed by boosting doses may be required.

Treatment of an infected individual with the compositions of the invention may hasten resolution of the infection in acutely infected individuals. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide compositions can also be used for the treatment of chronic infection and to stimulate the immune system to eliminate virus-infected cells in carriers. It is important to provide an amount of immuno-potentiating peptide in a formulation and mode of administration sufficient to effectively stimulate a cytotoxic T cell response. Thus, for treatment of chronic infection, a representative dose is in the range of about 1.0 µg to about 5000 µg, preferably about 5 µg to 1000 µg for a 70 kg patient per dose. Immunizing doses followed by boosting doses at established intervals, e.g., from one to four weeks, may be required, possibly for a prolonged period of time to effectively immunize an individual. In the case of chronic infection, administration should continue until at least clinical symptoms or laboratory tests indicate that the viral infection has been eliminated or substantially abated and for a period thereafter.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of CTL stimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptides of the invention may also be administered via liposomes, which serve to target the peptides to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid liability and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

In another aspect the present invention is directed to vaccines which contain as an active ingredient an immunogenically effective amount of an immunogenic peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of the virus or tumor cells. Useful carriers are well known in the art, and include, e.g., thyroglobulin, albumins such as human serum albumin, tetanus toxoid, polyamino acids such as poly(lysine:glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, CTL responses can be primed by conjugating peptides of the invention to lipids, such as P3CSS. Upon immunization with a peptide composition as described herein, via injection, aerosol, oral, transdermal or other route, the immune system of the host responds to the vaccine by producing large amounts of CTLs specific for the desired antigen, and the host becomes at least partially immune to later infection, or resistant to developing chronic infection.

Vaccine compositions containing the peptides of the invention are administered to a patient susceptible to or otherwise at risk of viral infection or cancer to elicit an immune response against the antigen and thus enhance the patient's own immune response capabilities. Such an amount is defined to be an "immunogenically effective dose." In this use, the precise amounts again depend on the patient's state of health and weight, the mode of administration, the nature of the formulation, etc., but generally range from about 1.0 µg to about 5000 µg per 70 kilogram patient, more commonly from about 10 µg to about 500 µg mg per 70 kg of body weight.

In some instances it may be desirable to combine the peptide vaccines of the invention with vaccines which induce neutralizing antibody responses to the virus of interest, particularly to viral envelope antigens.

For therapeutic or immunization purposes, nucleic acids encoding one or more of the peptides of the invention can also be administered to the patient. A number of methods are conveniently used to deliver the nucleic acids to the patient. For instance, the nucleic acid can be delivered directly, as "naked DNA". This approach is described, for instance, in Wolff et. al., *Science* 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. The nucleic acids can also be delivered complexed to cationic compounds, such as cationic lipids. Lipid-mediated gene delivery methods are described, for instance, in WO 96/18372; WO 93/24640; Mannino and Gould-Fogerite (1988) *BioTechniques* 6(7): 682-691; Rose U.S. Pat. No. 5,279,833; WO 91/06309; and Felgner et al. (1987) *Proc. Natl. Acad. Sci. USA* 84: 7413-7414. The peptides of the invention can also be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a noninfected host, the recombinant vaccinia virus expresses the immunogenic peptide, and thereby elicits a host CTL response. Vaccinia vectors and methods useful in immunization protocols are described in, e.g., U.S. Pat. No. 4,722,848, incorporated herein by reference. Another vector is BCG (Bacille Calmette Guerin). BCG vectors are described in Stover et al. (*Nature* 351:456-460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

A preferred means of administering nucleic acids encoding the peptides of the invention uses minigene constructs encoding multiple epitopes of the invention. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Standard regulatory sequences well known to those of skill in the art are included in the vector to ensure expression in the target cells. Several vector elements are required: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences can also be considered for increasing minigene expression. It has recently been proposed that immunostimulatory sequences (ISSs or CpGs) play a role in the immunogenicity of DNA vaccines. These sequences could be included in the vector, outside the minigene coding sequence, if found to enhance immunogenicity.

In some embodiments, a bioistronic expression vector, to allow production of the minigene-encoded epitopes and a second protein included to enhance or decrease immunogenicity can be used. Examples of proteins or polypeptides that could beneficially enhance the immune response if co-expressed include cytokines (e.g., IL2, IL12, GM-CSF), cytokine-inducing molecules (e.g. LeIF) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-β) may be beneficial in certain diseases.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

Therapeutic quantities of plasmid DNA are produced by fermentation in *E. coli*, followed by purification. Aliquots from the working cell bank are used to inoculate fermentation medium (such as Terrific Broth), and grown to saturation in shaker flasks or a bioreactor according to well known techniques. Plasmid DNA can be purified using standard bioseparation technologies such as solid phase anion-exchange resins supplied by Quiagen. If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). A variety of methods have been described, and new techniques may become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Target cell sensitization can be used as a functional assay for expression and MHC class I presentation of minigene-encoded CTL epitopes. The plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 labeled and used as target cells for epitope-specific CTL lines. Cytolysis, detected by 51Cr release, indicates production of MHC presentation of minigene-encoded CTL epitopes.

In vivo immunogenicity is a second approach for functional testing of minigene DNA formulations. Transgenic mice expressing appropriate human MHC molecules are immunized with the DNA product. The dose and route of administration are formulation dependent (e.g. IM for DNA in PBS, IP for lipid-complexed DNA). Twenty-one days after immunization, splenocytes are harvested and restimulated for 1 week in the presence of peptides encoding each epitope being tested. These effector cells (CTLs) are assayed for cytolysis of peptide-loaded, chromium-51 labeled target cells using standard techniques. Lysis of target cells sensitized by MHC loading of peptides corresponding to minigene-encoded epitopes demonstrates DNA vaccine function for in vivo induction of CTLs.

Antigenic peptides may be used to elicit CTL ex vivo, as well. The resulting CTL, can be used to treat chronic infections (viral or bacterial) or tumors in patients that do not respond to other conventional forms of therapy, or will not respond to a peptide vaccine approach of therapy. Ex vivo CTL responses to a particular pathogen (infectious agent or tumor antigen) are induced by incubating in tissue culture the patient's CTL precursor cells (CTLp) together with a source of antigen-presenting cells (APC) and the appropriate immunogenic peptide. After an appropriate incubation time (typically 1-4 weeks), in which the CTLp are activated and mature and expand into effector CTL, the cells are infused back into the patient, where they will destroy their specific target cell (an infected cell or a tumor cell).

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic infection.

The following example is offered by way of illustration, not by way of limitation.

EXAMPLE 1

Class I antigen isolation was carried out as described in the related applications, noted above. Naturally processed peptides were then isolated and sequenced as described there. An allele-specific motif and algorithms were determined and quantitative binding assays were carried out.

Using the motifs identified above for the HLA-A2.1 allele amino acid sequences from a number of antigens were analyzed for the presence of these motifs. Table 3 provides the results of these searches. The letter "J" represents norleucine.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

TABLE 3

| Peptide | AA | Sequence | Source | A*0201 | SEQ ID NO: |
|---------|----|-----------|--------|--------|------------|
| 17.0317 | 9  | LQIGNIISI | Flu.24 | 0.0130 | 1 |
| 38.0103 | 9  | NLSLSCHAA | CEA.432 | 0.0110 | 2 |

TABLE 3-continued

| Peptide | AA | Sequence | Source | A*0201 | SEQ ID NO: |
|---|---|---|---|---|---|
| 1233.11 | 9 | YLSGANLNV | CEA.605V9 | 0.0690 | 3 |
| 1295.03 | 9 | SMPPPGTRV | p53.149M2 | 0.0290 | 4 |
| 1295.04 | 9 | SLPPPGTRV | p53.149L2 | 0.0410 | 5 |
| 1317.24 | 9 | KTCPVQLWV | p53.139 | 0.0069 | 6 |
| 1323.02 | 9 | KLLPENNVV | p53.24V9 | 0.0130 | 7 |
| 1323.04 | 9 | ALNKMFBQV | p53.129B7V9 | 0.0260 | 8 |
| 1323.06 | 9 | KLBPVQLWV | p53.139L2B3 | 0.1100 | 9 |
| 1323.08 | 9 | BLTIHYNYV | p53.229B1L2V9 | 0.0430 | 10 |
| 1323.18 | 10 | LLPPQHLIRV | p53.188L2 | 0.0061 | 11 |
| 1323.29 | 11 | YMCNSSCMGGM | p53.236 | 0.0075 | 12 |
| 1323.31 | 11 | YLCNSSCMGGV | p53.236L2V11 | 0.2300 | 13 |
| 1323.34 | 11 | KLYQGSYGFRV | p53.101L2V11 | 0.0620 | 14 |
| 1324.07 | 9 | CQLAKTCPV | p53.135 | 0.0240 | 15 |
| 1325.01 | 9 | RLPEAAPPV | p53.65L2 | 0.0640 | 16 |
| 1325.02 | 9 | GLAPPQHLV | p53.187V9 | 0.0130 | 17 |
| 1325.04 | 9 | KMAELVHFL | MAGE3.112M2 | 0.2100 | 18 |
| 1325.05 | 9 | KLAELVHFL | MAGE3.112L2 | 0.2500 | 19 |
| 1326.01 | 9 | CLLAKTCPV | p53.135L2 | 0.0400 | 20 |
| 1326.02 | 9 | KLSQHMTEV | p53.164L2 | 0.0410 | 21 |
| 1326.04 | 9 | ELAPVVAPV | p53.68L2V9 | 0.0860 | 22 |
| 1326.06 | 9 | QLAKTCPVQV | p53.136 | 0.0320 | 23 |
| 1326.08 | 9 | HLTEVVRRV | p53.168L2 | 0.0180 | 24 |
| 1329.01 | 11 | KTYQGSYGFRL | | 0.0028 | 25 |
| 1329.03 | 10 | VVVPYEPPEV | p53.216 | 0.0081 | 26 |
| 1329.14 | 9 | BQLAKTBPV | p53.135B1B7 | 0.0490 | 27 |
| 1329.15 | 9 | BLLAKTBPV | p53.135B1L2B7 | 0.1100 | 28 |
| 1330.01 | 9 | QIIGYVIGT | CEA.78 | 0.0160 | 29 |
| 1330.02 | 9 | QLIGYVIGV | CEA.78L2V9 | 0.5300 | 30 |
| 1330.05 | 9 | YVCGIQNSV | CEA.569 | 0.0510 | 31 |
| 1330.06 | 9 | YLCGIQNSV | CEA.569L2 | 0.1000 | 32 |
| 1330.07 | 9 | ATVGIMIGV | CEA.687 | 0.1400 | 33 |
| 1330.08 | 9 | ALVGIMIGV | CEA.687L2 | 0.5000 | 34 |
| 1330.09 | 10 | VLYGPDDPTI | CEA.411 | 0.0170 | 35 |
| 1330.10 | 10 | VLYGPDDPTV | CEA.411V10 | 0.0310 | 36 |
| 1331.02 | 9 | DLMLSPDDV | p53.42V9 | | 37 |
| 1331.03 | 9 | ALMLSPDDI | p53.42A1 | | 38 |
| 1331.04 | 9 | ALMLSPDDV | p53.42A1V9 | | 39 |
| 1331.05 | 9 | DLMLSPADI | p53.42A7 | | 40 |
| 1331.06 | 9 | DLMLSPADV | p53.42A7V9 | | 41 |
| 1331.07 | 9 | DLMLSPDAI | p53.42A8 | | 42 |
| 1331.08 | 9 | DLMLSPDAV | p53.42A8V9 | | 43 |
| 38.0007 | 9 | AILTFGSFV | KSHV.89 | 0.0850 | 44 |
| 38.0009 | 9 | HLRDFALAV | KSHV.106 | 0.0183 | 45 |
| 38.0015 | 9 | ALLGSIALL | KSHV.155 | 0.0470 | 46 |
| 38.0018 | 9 | ALLATILAA | KSHV.161 | 0.0490 | 47 |
| 38.0019 | 9 | LLATILAAV | KSHV.162 | 0.1600 | 48 |
| 38.0022 | 9 | RLFADELAA | KSHV.14 | 0.0150 | 49 |
| 38.0024 | 9 | YLSKCTLAV | KSHV.65 | 0.2000 | 50 |
| 38.0026 | 9 | LVYHIYSKI | KSHV.153 | 0.0457 | 51 |
| 38.0029 | 9 | SMYLCILSA | KSHV.208 | 0.0250 | 52 |
| 38.0030 | 9 | YLCILSALV | KSHV.210 | 0.3500 | 53 |
| 38.0033 | 9 | VMFSYLQSL | KSHV.268 | 0.5000 | 54 |
| 38.0035 | 9 | RLHVYAYSA | KSHV.285 | 0.0270 | 55 |
| 38.0039 | 9 | GLQTLGAFV | KSHV.98 | 0.0110 | 56 |
| 38.0040 | 9 | FVEEQMTWA | KSHV.105 | 0.0380 | 57 |
| 38.0041 | 9 | QMTWAQTVV | KSHV.109 | 0.0110 | 58 |
| 38.0042 | 9 | IILDTAIFV | KSHV.130 | 0.6800 | 59 |
| 38.0043 | 9 | AIFVCNAFV | KSHV.135 | 0.0910 | 60 |
| 38.0046 | 9 | AMGNRLVEA | KSHV.172 | 0.0200 | 61 |
| 38.0047 | 9 | RLVEACNLL | KSHV.176 | 0.0180 | 62 |
| 38.0059 | 9 | TLSIVTFSL | KSHV.198 | 0.2200 | 63 |
| 38.0063 | 9 | KLSVLLLEV | KSHV.292 | 0.1400 | 64 |
| 38.0064 | 9 | LLLEVNRSV | KSHV.296 | 0.0270 | 65 |
| 38.0068 | 9 | FVSSPTLPV | KSHV.78 | 0.0350 | 66 |
| 38.0070 | 9 | AMLVLLAEI | KSHV.281 | 0.0820 | 67 |
| 38.0075 | 9 | QMARLAWEA | KSHV.1116 | 0.0990 | 68 |
| 38.0131 | 10 | VLAIEGIFMA | KSHV.10 | 0.0730 | 69 |
| 38.0132 | 10 | YLYHPLLSPI | KSHV.27 | 0.1400 | 70 |
| 38.0134 | 10 | SLFEAMLANV | KSHV.49 | 0.9500 | 71 |
| 38.0135 | 10 | STTGINQLGL | KSHV.62 | 0.0710 | 72 |
| 38.0137 | 10 | LAILTFGSFV | KSHV.88 | 0.0160 | 73 |
| 38.0139 | 10 | ALLGSIALLA | KSHV.155 | 0.0360 | 74 |
| 38.0141 | 10 | ALLATILAAV | KSHV.161 | 0.1100 | 75 |
| 38.0142 | 10 | LLATILAAVA | KSHV.162 | 0.0110 | 76 |
| 38.0143 | 10 | RLFADELAAL | KSHV.14 | 0.1800 | 77 |
| 38.0148 | 10 | YLSKCTLAVL | KSHV.65 | 0.0300 | 78 |
| 38.0150 | 10 | LLVYHIYSKI | KSHV.152 | 0.0130 | 79 |
| 38.0151 | 10 | SMYLCILSAL | KSHV.208 | 0.0360 | 80 |
| 38.0153 | 10 | HLHRQMLSFV | KSHV.68 | 0.0160 | 81 |
| 38.0163 | 10 | LLCGKTGAFL | KSHV.167 | 0.0100 | 82 |
| 38.0164 | 10 | ETLSIVTFSL | KSHV.197 | 0.0180 | 83 |
| 39.0063 | 9 | VMCTYSPPL | mp53.119 | 1.4000 | 84 |
| 39.0065 | 9 | KLFCQLAKT | mp53.129 | 0.0160 | 85 |
| 39.0067 | 9 | ATPPAGSRV | mp53.146 | 0.0130 | 86 |
| 39.0133 | 10 | FLQSGTAKSV | mp53.110 | 0.0180 | 87 |
| 39.0169 | 10 | CMDRGLTVFV | KSHV.311 | 0.0120 | 88 |
| 39.0170 | 10 | VLLNWWRWRL | KSHV.327 | 0.1500 | 89 |
| 40.0070 | 9 | GVFTGLTHI | HCV.1565 | 0.0110 | 90 |
| 40.0072 | 9 | QMWKCLIRL | HCV.1611 | 0.0620 | 91 |
| 40.0074 | 9 | IMTCMSADL | HCV.1650 | 0.0121 | 92 |
| 40.0076 | 9 | ALAAYCLST | HCV.1674 | 0.2500 | 93 |
| 40.0080 | 9 | VLSGKPAII | HCV.1692 | 0.0150 | 94 |
| 40.0082 | 9 | FISGIQYLA | HCV.1773 | 0.1000 | 95 |
| 40.0134 | 10 | YIMTCMSADL | HCV.1649 | 0.0300 | 96 |
| 40.0137 | 10 | AIASLMAFTA | HCV.1791 | 0.0580 | 97 |
| 40.0138 | 10 | GLAGAAIGSV | HCV.1838 | 0.0320 | 98 |
| 41.0058 | 8 | MIGVLVGV | CEA.692 | 0.0120 | 99 |
| 41.0061 | 9 | VLPLAYISL | TRP1 | 0.0110 | 100 |
| 41.0062 | 9 | SLGCIFFPL | TRP1 | 0.9700 | 101 |
| 41.0063 | 9 | PLAYISLFL | TRP1 | 0.0220 | 102 |
| 41.0065 | 9 | LMLFYQVWA | TRP1 | 0.0270 | 103 |
| 41.0071 | 9 | NISIYNYFV | TRP1 | 0.2300 | 104 |
| 41.0072 | 9 | NISVYNYFV | TRP1 | 0.0600 | 105 |
| 41.0075 | 9 | FVWTHYYSV | TRP1 | 1.5000 | 106 |
| 41.0077 | 9 | FLTWHRYHL | TRP1 | 0.5500 | 107 |
| 41.0078 | 9 | LTWHRYHLL | TRP1 | 0.1600 | 108 |
| 41.0082 | 9 | MLQEPSFSL | TRP1 | 0.6900 | 109 |
| 41.0083 | 9 | SLPYWNFAT | TRP1 | 0.0110 | 110 |
| 41.0088 | 9 | RLPEPQDVA | TRP1 | 0.0180 | 111 |
| 41.0090 | 9 | VTQCLEVRV | TRP1 | 0.0160 | 112 |
| 41.0096 | 9 | LLHTFTDAV | TRP1 | 0.2700 | 113 |
| 41.0100 | 9 | NMVPFWPPV | TRP1 | 0.6200 | 114 |
| 41.0104 | 9 | AVVGALLLV | TRP1 | 0.0210 | 115 |
| 41.0105 | 9 | AVVAALLLV | TRP1 | 0.0390 | 116 |
| 41.0108 | 9 | LLVAAIFGV | TRP1 | 1.9000 | 117 |
| 41.0112 | 9 | SMDEANQPL | TRP1 | 0.0770 | 118 |
| 41.0114 | 9 | VLPLAYISV | TRP1 | 0.1100 | 119 |
| 41.0115 | 9 | SLGCIFFPV | TRP1 | 3.2000 | 120 |
| 41.0116 | 9 | PLAYISLFV | TRP1 | 0.0310 | 121 |
| 41.0117 | 9 | LLLFQQARV | TRP1 | 0.1100 | 122 |
| 41.0118 | 9 | LMLFYQVWV | TRP1 | 2.4000 | 123 |
| 41.0119 | 9 | LLPSSGPGV | TRP1 | 0.3700 | 124 |
| 41.0121 | 9 | NLSIYNYFV | TRP1 | 0.9700 | 125 |
| 41.0122 | 9 | NLSVYNYFV | TRP1 | 0.8700 | 126 |
| 41.0123 | 9 | FLWTHYYSV | TRP1 | 5.6000 | 127 |
| 41.0124 | 9 | SLKKTFLGV | TRP1 | 0.0224 | 128 |
| 41.0125 | 9 | FLTWHRYHV | TRP1 | 0.3800 | 129 |
| 41.0129 | 9 | MLQEPSFSV | TRP1 | 1.6000 | 130 |
| 41.0130 | 9 | SLPYWNFAV | TRP1 | 0.5700 | 131 |
| 41.0131 | 9 | ALGKNVCDV | TRP1 | 0.0160 | 132 |
| 41.0132 | 9 | SLLISPNSV | TRP1 | 0.1300 | 133 |
| 41.0133 | 9 | SLFSQWRVV | TRP1 | 0.0740 | 134 |
| 41.0134 | 9 | TLGTLCNSV | TRP1 | 0.0330 | 135 |
| 41.0136 | 9 | RLPEPQDVV | TRP1 | 0.1000 | 136 |
| 41.0137 | 9 | VLQCLEVRV | TRP1 | 0.0360 | 137 |
| 41.0138 | 9 | SLNSFRNTV | TRP1 | 0.0140 | 138 |
| 41.0139 | 9 | SLDSFRNTV | TRP1 | 0.0440 | 139 |
| 41.0141 | 9 | FLNGTGGQV | TRP1 | 0.0220 | 140 |
| 41.0142 | 9 | VLLHTFTDV | TRP1 | 0.0180 | 141 |
| 41.0145 | 9 | ALVGALLLV | TRP1 | 0.2600 | 142 |
| 41.0146 | 9 | ALVAALLLV | TRP1 | 0.5800 | 143 |
| 41.0147 | 9 | LLVALIFGV | TRP1 | 1.0000 | 144 |
| 41.0148 | 9 | YLIRARRSV | TRP1 | 0.0170 | 145 |
| 41.0149 | 9 | SMDEANQPV | TRP1 | 0.1600 | 146 |
| 41.0151 | 10 | SLGCIFFPLL | TRP1 | 0.1800 | 147 |
| 41.0157 | 10 | GMCCPDLSPV | TRP1 | 0.0950 | 148 |
| 41.0160 | 10 | AACNQKILTV | TRP1 | 0.0120 | 149 |
| 41.0162 | 10 | FLTWHRYHLL | TRP1 | 0.0830 | 150 |
| 41.0166 | 10 | SLHNLAHLFL | TRP1 | 0.3900 | 151 |
| 41.0174 | 10 | LLLVAAIFGV | TRP1 | 0.3000 | 152 |

TABLE 3-continued

| Peptide | AA | Sequence | Source | A*0201 | SEQ ID NO: |
|---|---|---|---|---|---|
| 41.0177 | 10 | LLVAAIFGVA | TRP1 | 0.0820 | 153 |
| 41.0178 | 10 | ALIFGTASYL | TRP1 | 0.0230 | 154 |
| 41.0180 | 10 | SMDEANQPLL | TRP1 | 0.0250 | 155 |
| 41.0181 | 10 | LLTDQYQCYA | TRP1 | 0.0320 | 156 |
| 41.0183 | 10 | SLGCIFFPLV | TRP1 | 0.3200 | 157 |
| 41.0186 | 10 | FLMLFYQVWV | TRP1 | 0.8100 | 158 |
| 41.0189 | 10 | ALCDQRVLIV | TRP1 | 0.0530 | 159 |
| 41.0190 | 10 | ALCNQKILTV | TRP1 | 0.0770 | 160 |
| 41.0191 | 10 | FLTWHRYHLV | TRP1 | 0.0510 | 161 |
| 41.0197 | 10 | SLHNLAHLFV | TRP1 | 0.5000 | 162 |
| 41.0198 | 10 | NLAHLFLNGV | TRP1 | 0.4100 | 163 |
| 41.0199 | 10 | NMVPFWPPVV | TRP1 | 0.2800 | 164 |
| 41.0201 | 10 | ILVVAALLLV | TRP1 | 0.0190 | 165 |
| 41.0203 | 10 | LLVALIFGTV | TRP1 | 0.1200 | 166 |
| 41.0205 | 10 | ALIFGTASYV | TRP1 | 0.0900 | 167 |
| 41.0206 | 10 | SMDEANQPLV | TRP1 | 0.0350 | 168 |
| 41.0207 | 10 | LLTDQYQCYV | TRP1 | 0.2100 | 169 |
| 41.0212 | 11 | LLIQNIIQNDT | CEA.107 | 0.0140 | 170 |
| 41.0214 | 11 | IIQNDTGFYTL | CEA.112 | 0.0130 | 171 |
| 41.0221 | 11 | TLFNVTRNDTA | CEA.201 | 0.0110 | 172 |
| 41.0235 | 11 | LTLLSVTRNDV | CEA.378 | 0.0150 | 173 |
| 41.0243 | 11 | GLYTCQANNSA | CEA.473 | 0.0290 | 174 |
| 41.0268 | 11 | ATVGIMIGVLV | CEA.687 | 0.0160 | 175 |
| 44.0075 | 11 | GLVPPQHLIRV | mp53.184.V3 | 0.0370 | 176 |
| 44.0087 | 11 | GLAPPVHLIRV | mp53.184.V6 | 0.0330 | 177 |
| 44.0092 | 11 | GLAPPEHLIRV | mp53.184.E6 | 0.1600 | 178 |
| 1227.10 | 9 | ILIGVLVGV | CEA.691.L2 | 0.2300 | 179 |
| 1234.26 | 10 | YLIMVKCWMV | Her2/neu.952.L2 V10 | 0.3800 | 180 |
| 1295.06 | 9 | LLGRDSFEV | mp53.261 | 0.2000 | 181 |
| 1319.01 | 9 | FMYSDFHFI | Flu.RRP2.446 | 0.4400 | 182 |
| 1319.06 | 9 | NMLSTVLGV | Flu.RRP2.446 | 0.1700 | 183 |
| 1319.14 | 9 | SLENFRAYV | Flu.RRP2.446 | 0.0430 | 184 |
| 1325.06 |  | KMAELVHFV | Mage3.112 | 0.1900 | 185 |
| 1325.07 |  | KLAELVHFV | Mage3.112 | 0.3500 | 186 |
| 1334.01 |  | VLIQRNPQV | Her2/neu.153.V9 | 0.0910 | 187 |
| 1334.02 |  | VLLGVVFGV | Her2/neu.665.L2 V9 | 2.1000 | 188 |
| 1334.03 |  | SLISAVVGV | Her2/neu.653.L2 V9 | 0.7000 | 189 |
| 1334.04 |  | YMIMVKBWMI | Her2/neu.952.B7 | 0.2700 | 190 |
| 1334.05 |  | YLIMVKBWMV | Her2/neu.952.L2 B7V10 | 0.6900 | 191 |
| 1334.06 |  | KLWEELSVV | Mage3.220.L2V9 | 0.4500 | 192 |
| 1334.08 |  | AMBRWGLLV | Her2/neu.5.M2B3V9 | 0.1400 | 193 |
| 1345.01 | 9 | IJIGVLVGV | CEA.691.J2 | 0.0570 | 194 |
| 1345.02 | 9 | ATVGIJIGV | CEA.687.J6 | 0.1595 | 195 |
| 1345.03 | 9 | SJPPPGTRV | p53.149.J2 | 0.0545 | 196 |
| 1345.04 | 10 | LVFGIELJEV | MAGE3.160.J8 | 0.7650 | 197 |
| 918.12 | 8 | ILGFVFTL | Flu.M1.59 | 0.7900 | 198 |
| 1095.22 | 9 | KIFGSLAFL | Her2/neu |  | 199 |
| 1090.01 | 10 | YLQLVFGIEV | MAGE2 |  | 200 |
| 1126.01 | 9 | MMNDQLMFL | PSM |  | 201 |
| 1126.02 | 10 | ALVLAGGFFL | PSM |  | 202 |
| 1126.03 | 9 | WLCAGALVL | PSM |  | 203 |
| 1126.05 | 9 | MVFELANSI | PSM |  | 204 |
| 1126.06 | 10 | RMMNDQLMFL | PSM |  | 205 |
| 1126.09 | 9 | LVLAGGFFL | PSM |  | 206 |
| 1126.10 | 9 | VLAGGFLL | PSM |  | 207 |
| 1126.12 | 9 | LLHETDSAV | PSM |  | 208 |
| 1126.14 | 9 | LMYSLVHNL | PSM |  | 209 |
| 1126.16 | 10 | QLMFLERAFI | PSM |  | 210 |
| 1126.17 | 9 | LMFLERAFI | PSM |  | 211 |
| 1126.20 | 10 | KLGSGNDFEV | PSM |  | 212 |
| 1129.01 | 9 | LLQERGVAYI | PSM |  | 213 |
| 1129.04 | 10 | GMPEGDLVYV | PSM |  | 214 |
| 1129.05 | 10 | FLDELKAENI | PSM |  | 215 |
| 1129.08 | 9 | ALFDIESKV | PSM |  | 216 |
| 1129.10 | 10 | GLPSIPVHPI | PSM |  | 217 |

II. Non-HLA-A2 Motifs

The present invention also relates to the determination of allele-specific peptide motifs for human Class I MHC (sometimes referred to as HLA) allele subtypes. These motifs are then used to define T cell epitopes from any desired antigen, particularly those associated with human viral diseases, cancers or autoimmune diseases, for which the amino acid sequence of the potential antigen or autoantigen targets is known.

Epitopes on a number of potential target proteins can be identified in this manner. Examples of suitable antigens include prostate specific antigen (PSA), hepatitis B core and surface antigens (HBVc, HBVs) hepatitis C antigens, Epstein-Barr virus antigens, melanoma antigens (e.g., MAGE-1), human immunodeficiency virus (HIV) antigens and human papilloma virus (HPV) antigens, Lassa virus, *mycobacterium tuberculosis* (MT), p53, CEA, and Her2/neu.

Peptides comprising the epitopes from these antigens are synthesized and then tested for their ability to bind to the appropriate MHC molecules in assays using, for example, purified class I molecules and radioiodonated peptides and/or cells expressing empty class I molecules by, for instance, immunofluorescent staining and flow microfluorimetry, peptide-dependent class I assembly assays, and inhibition of CTL recognition by peptide competition. Those peptides that bind to the class I molecule are further evaluated for their ability to serve as targets for CTLs derived from infected or immunized individuals, as well as for their capacity to induce primary in vitro or in vivo CTL responses that can give rise to CTL populations capable of reacting with virally infected target cells or tumor cells as potential therapeutic agents.

The MHC class I antigens are encoded by the HLA-A, B, and C loci. HLA-A and B antigens are expressed at the cell surface at approximately equal densities, whereas the expression of HLA-C is significantly lower (perhaps as much as 10-fold lower). Each of these loci have a number of alleles. The peptide binding motifs of the invention are relatively specific for each allelic subtype.

For peptide-based vaccines, the peptides of the present invention preferably comprise a motif recognized by an MHC I molecule having a wide distribution in the human population. Since the MHC alleles occur at different frequencies within different ethnic groups and races, the choice of target MHC allele may depend upon the target population. Table 4 shows the frequency of various alleles at the HLA-A locus products among different races. For instance, the majority of the Caucasoid population can be covered by peptides which bind to four HLA-A allele subtypes, specifically HLA-A2.1, A1, A3.2, and A24.1. Similarly, the majority of the Asian population is encompassed with the addition of peptides binding to a fifth allele HLA-A11.2.

TABLE 4

| A Allele/Subtype | N(69)* | A(54) | C(502) |
|---|---|---|---|
| A1 | 10.1(7) | 1.8(1) | 27.4(138) |
| A2.1 | 11.5(8) | 37.0(20) | 39.8(199) |
| A2.2 | 10.1(7) | 0 | 3.3(17) |
| A2.3 | 1.4(1) | 5.5(3) | 0.8(4) |
| A2.4 | — | — | — |
| A2.5 | — | — | — |
| A3.1 | 1.4(1) | 0 | 0.2(0) |
| A3.2 | 5.7(4) | 5.5(3) | 21.5(108) |
| A11.1 | 0 | 5.5(3) | 0 |
| A11.2 | 5.7(4) | 31.4(17) | 8.7(44) |

TABLE 4-continued

| A Allele/Subtype | N(69)* | A(54) | C(502) |
|---|---|---|---|
| A11.3 | 0 | 3.7(2) | 0 |
| A23 | 4.3(3) | — | 3.9(20) |
| A24 | 2.9(2) | 27.7(15) | 15.3(77) |
| A24.2 | — | — | — |
| A24.3 | — | — | — |
| A25 | 1.4(1) | — | 6.9(35) |
| A26.1 | 4.3(3) | 9.2(5) | 5.9(30) |
| A26.2 | 7.2(5) | — | 1.0(5) |
| A26V | — | 3.7(2) | — |
| A28.1 | 10.1(7) | — | 1.6(8) |
| A28.2 | 1.4(1) | — | 7.5(38) |
| A29.1 | 1.4(1) | — | 1.4(7) |
| A29.2 | 10.1(7) | 1.8(1) | 5.3(27) |
| A30.1 | 8.6(6) | — | 4.9(25) |
| A30.2 | 1.4(1) | — | 0.2(1) |
| A30.3 | 7.2(5) | — | 3.9(20) |
| A31 | 4.3(3) | 7.4(4) | 6.9(35) |
| A32 | 2.8(2) | — | 7.1(36) |
| Aw33.1 | 8.6(6) | — | 2.5(13) |
| Aw33.2 | 2.8(2) | 16.6(9) | 1.2(6) |
| Aw34.1 | 1.4(1) | — | — |
| Aw34.2 | 14.5(10) | — | 0.8(4) |
| Aw36 | 5.9(4) | — | — |

Table compiled from B. DuPont, Immunobiology of HLA, Vol. I, Histocompatibility Testing 1987, Springer-Verlag, New York 1989.
*N - negroid; A = Asian; C = Caucasoid. Numbers in parenthesis represent the number of individuals included in the analysis.

The nomenclature used to describe peptide compounds follows the conventional practice wherein the amino group is presented to the left (the N-terminus) and the carboxyl group to the right (the C-terminus) of each amino acid residue. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids is represented by a lower case single letter or a lower case three letter symbol. Glycine has no asymmetric carbon atom and is simply referred to as "Gly" or G.

The procedures used to identify peptides of the present invention generally follow the methods disclosed in Falk et al., Nature 351:290 (1991), which is incorporated herein by reference. Briefly, the methods involve large-scale isolation of MHC class I molecules, typically by immunoprecipitation or affinity chromatography, from the appropriate cell or cell line. Examples of other methods for isolation of the desired MHC molecule equally well known to the artisan include ion exchange chromatography, lectin chromatography, size exclusion, high performance ligand chromatography, and a combination of all of the above techniques.

A large number of cells with defined MHC molecules, particularly MHC Class I molecules, are known and readily available. For example, human EBV-transformed B cell lines have been shown to be excellent sources for the preparative isolation of class I and class II MHC molecules. Well-characterized cell lines are available from private and commercial sources, such as American Type Culture Collection ("Catalogue of Cell Lines and Hybridomas," 6th edition (1988) Rockville, Md., U.S.A.); National Institute of General Medical Sciences 1990/1991 Catalog of Cell Lines (NIGMS) Human Genetic Mutant Cell Repository, Camden, N.J.; and ASHI Repository, Bingham and Women's Hospital, 75 Francis Street, Boston, Mass. 02115. Table 5 lists some B cell lines suitable for use as sources for HLA-A alleles. All of these cell lines can be grown in large batches and are therefore useful for large scale production of MHC molecules. One of skill will recognize that these are merely exemplary cell lines and that many other cell sources can be employed. Similar EBV B cell lines homozygous for HLA-B and HLA-C could serve as sources for HLA-B and HLA-C alleles, respectively.

TABLE 5

HUMAN CELL LINES (HLA-A SOURCES)

| HLA-A allele | B cell line |
|---|---|
| A1 | MAT |
|  | COX (9022) |
|  | STEINLIN (9087) |
| A2.1 | JY |
| A3.2 | EHM (9080) |
|  | HO301 (9055)GM3107 |
| A24.1 | T3(9107),TISI (9042) |
| A11 | BVR (GM6828A) |
|  | WT100 (GM8602)WT52 (GM8603) |

In the typical case, immunoprecipitation is used to isolate the desired allele. A number of protocols can be used, depending upon the specificity of the antibodies used. For example, allele-specific mAb reagents can be used for the affinity purification of the HLA-A, HLA-B, and HLA-C molecules. Several mAb reagents for the isolation of HLA-A molecules are available (Table 6). Thus, for each of the targeted HLA-A alleles, reagents are available that may be used for the direct isolation of the HLA-A molecules. Affinity columns prepared with these mAbs using standard techniques are successfully used to purify the respective HLA-A allele products.

In addition to allele-specific mAbs, broadly reactive anti-HLA-A, B, C mAbs, such as W6/32 and B9.12.1, and one anti-HLA-B, C mAb, B1.23.2, could be used in alternative affinity purification protocols as described in the example section below.

TABLE 6

ANTIBODY REAGENTS

| anti-HLA | Name | |
|---|---|---|
| HLA-A1 | 12/18 | |
| HLA-A3 | GAPA3 | (ATCC, HB122) |
| HLA-11,24.1 | A11.1M | (ATCC, HB164) |
| HLA-A,B,C | W6/32 | (ATCC, HB95) |
| monomorphic | B9.12.1 | (INSERM-CNRS) |
| HLA-B,C | B.1.23.2 | (INSERM-CNRS) |
| monomorphic | | |

The peptides bound to the peptide binding groove of the isolated MHC molecules are eluted typically using acid treatment. Peptides can also be dissociated from class I molecules by a variety of standard denaturing means, such as heat, pH, detergents, salts, chaotropic agents, or a combination thereof.

Peptide fractions are further separated from the MHC molecules by reversed-phase high performance liquid chromatography (HPLC) and sequenced. Peptides can be separated by a variety of other standard means well known to the artisan, including filtration, ultrafiltration, electrophoresis, size chromatography, precipitation with specific antibodies, ion exchange chromatography, isoelectrofocusing, and the like.

Sequencing of the isolated peptides can be performed according to standard techniques such as Edman degradation (Hunkapiller, M. W., et al., *Methods Enzymol.* 91, 399 [1983]). Other methods suitable for sequencing include mass spectrometry sequencing of individual peptides as previously described (Hunt, et al., *Science* 225:1261 (1992), which is incorporated herein by reference). Amino acid sequencing of bulk heterogenous peptides (e.g., pooled HPLC fractions) from different class I molecules typically reveals a characteristic sequence motif for each class I allele.

Definition of motifs specific for different class I alleles allows the identification of potential peptide epitopes from an antigenic protein whose amino acid sequence is known. Typically, identification of potential peptide epitopes is initially carried out using a computer to scan the amino acid sequence of a desired antigen for the presence of motifs. The epitopic sequences are then synthesized. The capacity to bind MHC Class molecules is measured in a variety of different ways. One means is a Class I molecule binding assay as described in the related applications, noted above. Other alternatives described in the literature include inhibition of antigen presentation (Sette, et al., *J. Immunol.* 141:3893 (1991), in vitro assembly assays (Townsend, et al., *Cell* 62:285 (1990), and FACS based assays using mutated ells, such as RMA.S (Melief, et al., *Eur. J. Immunol.* 21:2963 (1991)).

Next, peptides that test positive in the MHC class I binding assay are assayed for the ability of the peptides to induce specific CTL responses in vitro. For instance, Antigen-presenting cells that have been incubated with a peptide can be assayed for the ability to induce CTL responses in responder cell populations. Antigen-presenting cells can be normal cells such as peripheral blood mononuclear cells or dendritic cells (Inaba, et al., *J. Exp. Med.* 166:182 (1987); Boog, *Eur. J. Immunol.* 18:219 [1988]).

Alternatively, mutant mammalian cell lines that are deficient in their ability to load class I molecules with internally processed peptides, such as the mouse cell lines RMA-S (Kärre, et al. *Nature,* 319:675 (1986); Ljunggren, et al., *Eur. J. Immunol.* 21:2963-2970 (1991)), and the human somatic T cell hybrid, T-2 (Cerundolo, et al., *Nature* 345:449-452 (1990)) and which have been transfected with the appropriate human class I genes are conveniently used, when peptide is added to them, to test for the capacity of the peptide to induce in vitro primary CTL responses. Other eukaryotic cell lines which could be used include various insect cell lines such as mosquito larvae (ATCC cell lines CCL 125, 126, 1660, 1591, 6585, 6586), silkworm (ATTC CRL 8851), armyworm (ATCC CRL 1711), moth (ATCC CCL 80) and *Drosophila* cell lines such as a Schneider cell line (see Schneider *J. Embryol. Exp. Morphol.* 27:353-365 [1927]).

Peripheral blood lymphocytes are conveniently isolated following simple venipuncture or leukopheresis of normal donors or patients and used as the responder cell sources of CTL precursors. In one embodiment, the appropriate antigen-presenting cells are incubated with 10-100 μM of peptide in serum-free media for 4 hours under appropriate culture conditions. The peptide-loaded antigen-presenting cells are then incubated with the responder cell populations in vitro for 7 to 10 days under optimized culture conditions. Positive CTL activation can be determined by assaying the cultures for the presence of CTLs that kill radiolabeled target cells, both specific peptide-pulsed targets as well as target cells expressing endogenously processed form of the relevant virus or tumor antigen from which the peptide sequence was derived.

Specificity and MHC restriction of the CTL is determined by testing against different peptide target cells expressing appropriate or inappropriate human MHC class I. The peptides that test positive in the MHC binding assays and give rise to specific CTL responses are referred to herein as immunogenic peptides.

The immunogenic peptides can be prepared synthetically, or by recombinant DNA technology or from natural sources such as whole viruses or tumors. Although the peptide will preferably be substantially free of other naturally occurring host cell proteins and fragments thereof, in some embodiments the peptides can be synthetically conjugated to native fragments or particles.

The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. When possible, it may be desirable to optimize peptides of the invention to a length of 9 or 10 amino acid residues, commensurate in size with endogenously processed viral peptides or tumor cell peptides that are bound to MHC class I molecules on the cell surface.

Peptides having the desired activity may be modified as necessary to provide certain desired attributes, e.g., improved pharmacological characteristics, while increasing or at least retaining substantially all of the biological activity of the unmodified peptide to bind the desired MHC molecule and activate the appropriate T cell. For instance, the peptides may be subject to various changes, such as substitutions, either conservative or non-conservative, where such changes might provide for certain advantages in their use, such as improved MHC binding. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications may be made using well known peptide synthesis procedures, as described in e.g., Merrifield, *Science* 232: 341-347 (1986), Barany and Merrifield, *The Peptides*, Gross and Meienhofer, eds. (N.Y., Academic Press), pp. 1-284 (1979); and Stewart and Young, *Solid Phase Peptide Synthesis*, (Rockford, Ill., Pierce), 2d Ed. (1984), incorporated by reference herein.

The peptides can also be modified by extending or decreasing the compound's amino acid sequence, e.g., by the addition or deletion of amino acids. The peptides or analogs of the invention can also be modified by altering the order or composition of certain residues, it being readily appreciated that certain amino acid residues essential for biological activity, e.g., those at critical contact sites or conserved residues, may generally not be altered without an adverse effect on biological activity. The non-critical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

Typically, a series of peptides with single amino acid substitutions are employed to determine the effect of electrostatic charge, hydrophobicity, etc. on binding. For instance, a series of positively charged (e.g., Lys or Arg) or negatively charged (e.g., Glu) amino acid substitutions are made along the length of the peptide revealing different patterns of sensitivity towards various MHC molecules and T cell receptors. In addition, multiple substitutions using small, relatively neutral moieties such as Ala, Gly, Pro, or similar residues may be employed. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule or T cell receptor may also be achieved by such substitutions, compared to the affinity of the parent peptide. In any event, such substitutions should employ amino acid residues or other molecular fragments chosen to avoid, for example, steric and charge interference which might disrupt binding.

Amino acid substitutions are typically of single residues. Substitutions, deletions, insertions or any combination thereof may be combined to arrive at a final peptide. Substitutional variants are those in which at least one residue of a peptide has been removed and a different residue inserted in its place. Such substitutions generally are made in accordance with the following Table 2 when it is desired to finely modulate the characteristics of the peptide.

TABLE 7

| Original Residue | Exemplary Substitution |
|---|---|
| Ala | Ser |
| Arg | Lys, His |
| Asn | Gln |
| Asp | Glu |
| Cys | Ser |
| Glu | Asp |
| Gly | Pro |
| His | Lys; Arg |
| Ile | Leu; Val |
| Leu | Ile; Val |
| Lys | Arg; His |
| Met | Leu; Ile |
| Phe | Tyr; Trp |
| Ser | Thr |
| Thr | Ser |
| Trp | Tyr; Phe |
| Tyr | Trp; Phe |
| Val | Ile; Leu |
| Pro | Gly |

Substantial changes in function (e.g., affinity for MHC molecules or T cell receptors) are made by selecting substitutions that are less conservative than those in Table 2, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in peptide properties will be those in which (a) hydrophilic residue, e.g. seryl, is substituted for (or by) a hydrophobic residue, e.g. leucyl, isoleucyl, phenylalanyl, valyl or alanyl; (b) a residue having an electropositive side chain, e.g., lysl, arginyl, or histidyl, is substituted for (or by) an electronegative residue, e.g. glutamyl or aspartyl; or (c) a residue having a bulky side chain, e.g. phenylalanine, is substituted for (or by) one not having a side chain, e.g., glycine.

The peptides may also comprise isosteres of two or more residues in the immunogenic peptide. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, Chemistry and Biochemistry of Amino Acids, peptides and Proteins, Vol. VII (Weinstein ed., 1983).

Modifications of peptides with various amino acid mimetics or unnatural amino acids are particularly useful in increasing the stability of the peptide in vivo. Stability can be assayed in a number of ways. For instance, peptidases and various biological media, such as human plasma and serum, have been used to test stability. See, e.g., Verhoef et al., *Eur. J. Drug Metab. Pharmacokin.* 11:291-302 (1986). Half life of the peptides of the present invention is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

The peptides of the present invention or analogs thereof which have CTL stimulating activity may be modified to provide desired attributes other than improved serum half life. For instance, the ability of the peptides to induce CTL activity can be enhanced by linkage to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the CTL peptide may be linked to the T helper peptide without a spacer.

The immunogenic peptide may be linked to the T helper peptide either directly or via a spacer either at the amino or carboxy terminus of the CTL peptide. The amino terminus of either the immunogenic peptide or the T helper peptide may be acylated. Exemplary T helper peptides include tetanus toxoid 830-843, influenza 307-319, malaria circumsporozoite 382-398 and 378-389.

In some embodiments it may be desirable to include in the pharmaceutical compositions of the invention at least one component which primes CTL. Lipids have been identified as agents capable of priming CTL in vivo against viral antigens. For example, palmitic acid residues can be attached to the alpha and epsilon amino groups of a Lys residue and then linked, e.g., via one or more linking residues such as Gly, Gly-Gly-, Ser, Ser-Ser, or the like, to an immunogenic peptide. The lipidated peptide can then be injected directly in a micellar form, incorporated into a liposome or emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinyl-seryl-serine (P3CSS) can be used to prime virus specific CTL when covalently attached to an appropriate peptide. See, Deres et al., *Nature* 342:561-564 (1989), incorporated herein by reference. Peptides of the invention can be coupled to $P^3CSS$, for example, and the lipopeptide administered to an individual to specifically prime a CTL response to the target antigen. Further, as the induction of neutralizing antibodies can also be primed with $P^3CSS$ conjugated to a peptide which displays an appropriate epitope, the two compositions can be combined to more effectively elicit both humoral and cell-mediated responses to infection.

In addition, additional amino acids can be added to the termini of a peptide to provide for ease of linking peptides one to another, for coupling to a carrier support, or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide. Modification at the C terminus in some cases may alter binding characteristics of the peptide. In addition, the peptide or oligopeptide sequences can differ from the natural sequence by being modified by terminal-$NH_2$-acylation, e.g., by alkanoyl ($C_1$-$C_{20}$) or thioglycolyl acetylation, terminal-carboxylamidation, e.g., ammonia, methylamine, etc. In some instances these modifications may provide sites for linking to a support or other molecule.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis,* 2d. ed., Pierce Chemical Co. (1984), supra.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual,* Cold Spring Harbor Press, Cold Spring Harbor, N.Y. (1982), which is incorporated herein by reference. Thus, fusion proteins which comprise one or more peptide sequences of the invention can be used to present the appropriate T cell epitope.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

The peptides of the present invention and pharmaceutical and vaccine compositions thereof are useful for administration to mammals, particularly humans, to treat and/or prevent viral infection and cancer. Examples of diseases which can be treated using the immunogenic peptides of the invention include prostate cancer, hepatitis B, hepatitis C, AIDS, renal carcinoma, cervical carcinoma, lymphoma, CMV and condyloma acuminatum.

For pharmaceutical compositions, the immunogenic peptides of the invention are administered to an individual already suffering from cancer or infected with the virus of interest. Those in the incubation phase or the acute phase of infection can be treated with the immunogenic peptides separately or in conjunction with other treatments, as appropriate. In therapeutic applications, compositions are administered to a patient in an amount sufficient to elicit an effective CTL response to the virus or tumor antigen and to cure or at least partially arrest symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 µg to about 5000 µg of peptide for a 70 kg patient, followed by boosting dosages of from about 1.0 µg to about 1000 µg of peptide pursuant to a boosting regimen over weeks to months depending upon the patient's response and condition by measuring specific CTL activity in the patient's blood. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

For therapeutic use, administration should begin at the first sign of viral infection or the detection or surgical removal of tumors or shortly after diagnosis in the case of acute infection. This is followed by boosting doses until at least symptoms are substantially abated and for a period thereafter. In chronic infection, loading doses followed by boosting doses may be required.

Treatment of an infected individual with the compositions of the invention may hasten resolution of the infection in acutely infected individuals. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide compositions can also be used for the treatment of chronic infection and to stimulate the immune system to eliminate virus-infected cells in carriers. It is important to provide an amount of immuno-potentiating peptide in a formulation and mode of administration sufficient to effectively stimulate a cytotoxic T cell response. Thus, for treatment of chronic infection, a representative dose is in the range of about 1.0 µg to about 5000 µg, preferably about 5 µg to 1000 µg for a 70 kg patient per dose. Immunizing doses followed by boosting doses at established intervals, e.g., from one to four weeks, may be required, possibly for a prolonged period of time to effectively immunize an individual. In the case of chronic infection, administration should continue until at least clinical symptoms or laboratory tests indicate that the viral infection has been eliminated or substantially abated and for a period thereafter.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of CTL stimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptides of the invention may also be administered via liposomes, which serve to target the peptides to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid liability and stability of the liposomes in the blood stream. A variety of methods are available for preparing liposomes, as described in, e.g., Szoka et al., Ann. Rev. Biophys. Bioeng. 9:467 (1980), U.S. Pat. Nos. 4,235,871, 4,501,728, 4,837,028, and 5,019,369, incorporated herein by reference.

For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

In another aspect the present invention is directed to vaccines which contain as an active ingredient an immunogenically effective amount of an immunogenic peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of the virus or tumor cells. Useful carriers are well known in the art, and include, e.g., thyroglobulin, albumins such as human serum albumin, tetanus toxoid, polyamino acids such as poly(lysine:glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, CTL responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of CTLs specific for the desired antigen, and the host becomes at least partially immune to later infection, or resistant to developing chronic infection.

Vaccine compositions containing the peptides of the invention are administered to a patient susceptible to or otherwise at risk of viral infection or cancer to elicit an immune response against the antigen and thus enhance the patient's own immune response capabilities. Such an amount is defined to be an "immunogenically effective dose." In this use, the precise amounts again depend on the patient's state of health and weight, the mode of administration, the nature of the formulation, etc., but generally range from about 1.0 μg to about 5000 μg per 70 kilogram patient, more commonly from about 10 μg to about 500 μg mg per 70 kg of body weight.

In some instances it may be desirable to combine the peptide vaccines of the invention with vaccines which induce neutralizing antibody responses to the virus of interest, particularly to viral envelope antigens.

For therapeutic or immunization purposes, nucleic acids encoding one or more of the peptides of the invention can also be administered to the patient. A number of methods are conveniently used to deliver the nucleic acids to the patient. For instance, the nucleic acid can be delivered directly, as "naked DNA". This approach is described, for instance, in Wolff et. al., *Science* 247:1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. The nucleic acids can also be delivered complexed to cationic compounds, such as cationic lipids. Lipid-mediated gene delivery methods are described, for instance, in WO 96/18372; WO 93/24640; Mannino and Gould-Fogerite (1988) BioTechniques 6(7):682-691; Rose U.S. Pat. No. 5,279,833; WO 91/06309; and Felgner et al. (1987) Proc. Natl. Acad. Sci. USA 84: 7413-7414. The peptides of the invention can also be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a noninfected host, the recombinant vaccinia virus expresses the immunogenic peptide, and thereby elicits a host CTL response. Vaccinia vectors and methods useful in immunization protocols are described in, e.g., U.S. Pat. No. 4,722,848, incorporated herein by reference. Another vector is BCG (Bacille Calmette Guerin). BCG vectors are described in Stover et al. (*Nature* 351:456-460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

A preferred means of administering nucleic acids encoding the peptides of the invention uses minigene constructs encoding multiple epitopes of the invention. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Standard regulatory sequences well known to those of skill in the art are included in the vector to ensure expression in the target cells. Several vector elements are required: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences can also be considered for increasing minigene expression. It has recently been proposed that immunostimulatory sequences (ISSs or CpGs) play a role in the immunogenicity of DNA vaccines. These sequences could be included in the vector, outside the minigene coding sequence, if found to enhance immunogenicity.

In some embodiments, a bioistronic expression vector, to allow production of the minigene-encoded epitopes and a second protein included to enhance or decrease immunogenicity can be used. Examples of proteins or polypeptides that could beneficially enhance the immune response if co-expressed include cytokines (e.g., IL2, IL12, GM-CSF), cytokine-inducing molecules (e.g. LeIF) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-β) may be beneficial in certain diseases.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis.

Bacterial cells harboring the correct plasmid can be stored as a master cell bank and a working cell bank.

Therapeutic quantities of plasmid DNA are produced by fermentation in *E. coli*, followed by purification. Aliquots from the working cell bank are used to inoculate fermentation medium (such as Terrific Broth), and grown to saturation in shaker flasks or a bioreactor according to well known techniques. Plasmid DNA can be purified using standard bioseparation technologies such as solid phase anion-exchange resins supplied by Quiagen. If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). A variety of methods have been described, and new techniques may become available. As noted above, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Target cell sensitization can be used as a functional assay for expression and MHC class I presentation of minigene-encoded CTL epitopes. The plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 labeled and used as target cells for epitope-specific CTL lines. Cytolysis, detected by 51Cr release, indicates production of MHC presentation of minigene-encoded CTL epitopes.

In vivo immunogenicity is a second approach for functional testing of minigene DNA formulations. Transgenic mice expressing appropriate human MHC molecules are immunized with the DNA product. The dose and route of administration are formulation dependent (e.g. IM for DNA in PBS, IP for lipid-complexed DNA). Twenty-one days after immunization, splenocytes are harvested and restimulated for 1 week in the presence of peptides encoding each epitope being tested. These effector cells (CTLs) are assayed for cytolysis of peptide-loaded, chromium-51 labeled target cells using standard techniques. Lysis of target cells sensitized by MHC loading of peptides corresponding to minigene-encoded epitopes demonstrates DNA vaccine function for in vivo induction of CTLs.

Antigenic peptides may be used to elicit CTL ex vivo, as well. The resulting CTL, can be used to treat chronic infections (viral or bacterial) or tumors in patients that do not respond to other conventional forms of therapy, or will not respond to a peptide vaccine approach of therapy. Ex vivo CTL responses to a particular pathogen (infectious agent or tumor antigen) are induced by incubating in tissue culture the patient's CTL precursor cells (CTLp) together with a source of antigen-presenting cells (APC) and the appropriate immunogenic peptide. After an appropriate incubation time (typically 1-4 weeks), in which the CTLp are activated and mature and expand into effector CTL, the cells are infused back into the patient, where they will destroy their specific target cell (an infected cell or a tumor cell). In order to optimize the in vitro conditions for the generation of specific cytotoxic T cells, the culture of stimulator cells is maintained in an appropriate serum-free medium.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that will allow about 200, and preferably 200 or more, human Class I MHC molecules loaded with peptide to be expressed on the surface of each stimulator cell. Preferably, the stimulator cells are incubated with >20 µg/ml peptide.

Resting or precursor CD8+ cells are then incubated in culture with the appropriate stimulator cells for a time period sufficient to activate the CD8+ cells. Preferably, the CD8+ cells are activated in an antigen-specific manner. The ratio of resting or precursor CD8+ (effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:stimulator cell ratio is in the range of about 30:1 to 300:1. The effector/stimulator culture may be maintained for as long a time as is necessary to stimulate a therapeutically useable or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatibility complex molecules on cells allows the induction of primary cytotoxic T lymphocyte responses. Peptide loading of empty major histocompatibility complex molecules on cells enables the induction of primary cytotoxic T lymphocyte responses.

Since mutant cell lines do not exist for every human MHC allele, it is advantageous to use a technique to remove endogenous MHC-associated peptides from the surface of APC, followed by loading the resulting empty MHC molecules with the immunogenic peptides of interest. The use of non-transformed (non-tumorigenic), non-infected cells, and preferably, autologous cells of patients as APC is desirable for the design of CTL induction protocols directed towards development of ex vivo CTL therapies. This application discloses methods for stripping the endogenous MHC-associated peptides from the surface of APC followed by the loading of desired peptides.

A stable MHC class I molecule is a trimeric complex formed of the following elements: 1) a peptide usually of 8-10 residues, 2) a transmembrane heavy polymorphic protein chain which bears the peptide-binding site in its α1 and α2 domains, and 3) a non-covalently associated non-polymorphic light chain, $\beta_2$ microglobulin. Removing the bound peptides and/or dissociating the $\beta_2$ microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include lowering the culture temperature from 37° C. to 26° C. overnight to destabilize $\beta_2$ microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class II molecules. Most importantly, treatment of cells with the mild acid solutions do not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+ CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1\times10^6$ to about $1\times10^{12}$, more preferably about $1\times10^8$ to about $1\times10^{11}$, and even more preferably, about $1\times10^9$ to about $1\times10^{10}$ activated CD8+ cells are utilized for adult humans, compared to about $5\times10^6$-$5\times10^7$ cells used in mice.

Preferably, as discussed above, the activated CD8+ cells are harvested from the cell culture prior to administration of the CD8+ cells to the individual being treated. It is important to note, however, that unlike other present and proposed treatment modalities, the present method uses a cell culture system that is not tumorigenic. Therefore, if complete separation of stimulator cells and activated CD8+ cells is not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

The immunogenic peptides of this invention may also be used to make monoclonal antibodies. Such antibodies may be useful as potential diagnostic or therapeutic agents.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic infection.

To identify peptides of the invention, class I antigen isolation, and isolation and sequencing of naturally processed peptides was carried out as described in the related applications. These peptides were then used to define specific binding motifs for each of the following alleles A3.2, A1, A11, and A24.1. These motifs are described on page 3, above. The motifs described in Tables 8-11, below, are defined from pool sequencing data of naturally processed peptides as described in the related applications.

TABLE 8

Summary
HLA-A3.2 Allele-Specific Motif (SEQ ID NO:378)

| Position | Conserved Residues |
|---|---|
| 1 | — |
| 2 | V,L,M |
| 3 | Y,D |
| 4 | — |
| 5 | — |
| 6 | — |
| 7 | I |
| 8 | Q,N |
| 9 | K |
| 10 | K |

TABLE 9

Summary
HLA-A1 Allele-Specific Motif SEQ ID NO:218

| Position | Conserved Residues |
|---|---|
| 1 | — |
| 2 | S,T |
| 3 | D,E |
| 4 | P |
| 5 | — |
| 6 | — |
| 7 | L |
| 8 | — |
| 9 | Y |
| 10 | K |

TABLE 10

Summary
HLA-A11 Allele-Specific Motif (SEQ ID NO:379)

| Position | Conserved Residues |
|---|---|
| 1 | — |
| 2 | T,V |
| 3 | M,F |
| 4 | — |
| 5 | — |
| 6 | — |
| 7 | — |
| 8 | Q |
| 9 | K |
| 10 | K |

TABLE 11

Summary
HLA-A24.1 Allele-Specific Motif (SEQ ID NO:380)

| Position | Conserved Residues |
|---|---|
| 1 | — |
| 2 | Y |
| 3 | I,M |
| 4 | D,E,G,K,P |
| 5 | L,M,N |
| 6 | V |
| 7 | N,V |
| 8 | A,E,K,Q,S |
| 9 | F,L |
| 10 | F,A |

EXAMPLE 2

Identification of Immunogenic Peptides

Using the motifs identified above for various MHC class I allele amino acid sequences from various pathogens and tumor-related proteins were analyzed for the presence of these motifs. Screening was carried out described in the related applications. Table 12 provides the results of searches of the antigens.

TABLE 12

| Peptide | AA | Sequence | Source | A*0301 | A*1101 | SEQ ID NO: |
|---|---|---|---|---|---|---|
| 28.0719 | 10 | ILEQWVAGRK | HDV.nuc.16 | 0.0170 | 0.0012 | 219 |
| 28.0727 | 10 | LSAGGKNLSK | HDV.nuc.115 | 0.0097 | 0.0150 | 220 |
| 1259.02 | 11 | STDTVDTVLEK | Flu.HA.29 | 0.0001 | 0.0670 | 221 |
| 1259.04 | 9 | GIAPLQLGK | Flu.HA.63 | 0.6100 | 0.2000 | 222 |
| 1259.06 | 10 | VTAACSHAGK | Flu.HA.149 | 0.0380 | 0.0490 | 223 |
| 1259.08 | 9 | GIHHPSNSK | Flu.HA.195 | 0.1300 | 0.0140 | 224 |
| 1259.10 | 10 | RMNYYWTLLK | Flu.HA.243 | 2.5000 | 2.3000 | 225 |
| 1259.12 | 11 | ITNKVNSVIEK | Flu.HA.392 | 0.0200 | 0.0670 | 226 |
| 1259.13 | 11 | KMNIQFTAVGK | Flu.HA.402 | 0.0280 | 0.0092 | 227 |
| 1259.14 | 9 | NIQFTAVGK | Flu.HA.404 | 0.0017 | 0.0330 | 228 |
| 1259.16 | 11 | AVGKEFNKLEK | Flu.HA.409 | 0.0210 | 0.0460 | 229 |
| 1259.19 | 11 | KVKSQLKNNAK | Flu.HA.465 | 0.0470 | 0.0031 | 230 |
| 1259.20 | 11 | SVRNGTYDYPK | Flu.HA.495 | 0.0410 | 0.1400 | 231 |
| 1259.21 | 9 | SIIPSGPLK | Flu.VMT1.13 | 0.7800 | 8.8000 | 232 |
| 1259.25 | 10 | RMVLASTTAK | Flu.VMT1.178 | 0.5500 | 0.0350 | 233 |
| 1259.26 | 9 | MVLASTTAK | Flu.VMT1.179 | 1.7000 | 1.4000 | 234 |
| 1259.28 | 10 | RMGVQMQRFK | Flu.VMT1.243 | 0.1000 | 0.0059 | 235 |
| 1259.33 | 10 | ATEIRASVGK | Flu.VNUC.22 | 0.1400 | 0.3000 | 236 |
| 1259.37 | 11 | TMVMELVRMIK | Flu.VNUC.188 | 0.0890 | 0.0310 | 237 |
| 1259.43 | 10 | RVLSFIKGTK | Flu.VNUC.342 | 0.8000 | 0.0830 | 238 |
| F119.01 | 9 | MSLQRQFLR | ORF3P | 0.2000 | 0.7200 | 239 |
| F119.02 | 9 | LLGPGRPYR | TRP.197 | 0.0190 | 0.0091 | 240 |
| F119.03 | 9 | LLGPGRPYK | TRP.197K9 | 2.2000 | 0.6800 | 241 |
| 34.0019 | 8 | RVYPELPK | CEA.139 | 0.0130 | 0.0440 | 242 |
| 34.0020 | 8 | TVSAELPK | CEA.495 | 0.0037 | 0.0320 | 243 |
| 34.0021 | 8 | TVYAEPPK | CEA.317 | 0.0160 | 0.0220 | 244 |
| 34.0029 | 8 | TINYTLWR | MAGE2.74 | 0.0140 | 0.0550 | 245 |
| 34.0030 | 8 | LVHFLLLK | MAGE2.116 | 0.0290 | 0.1500 | 246 |
| 34.0031 | 8 | SVFAHPRK | MAGE2.237 | 0.1410 | 0.0810 | 247 |
| 34.0043 | 8 | KVLHHMVK | MAGE3.285 | 0.0580 | 0.0190 | 248 |
| 34.0050 | 8 | RVCACPGR | p53.273 | 0.3500 | 0.0490 | 249 |
| 34.0051 | 8 | KMFCQLAK | p53.132 | 0.3800 | 0.3600 | 250 |
| 34.0062 | 8 | RAHSSHLK | p53.363 | 0.5500 | 0.0071 | 251 |
| 34.0148 | 9 | FVSNLATGR | CEA.656 | 0.0019 | 0.0490 | 252 |
| 34.0152 | 9 | RLQLSNGNK | CEA.546 | 0.0250 | 0.0110 | 253 |
| 34.0153 | 9 | RINGIPQQK | CEA.628 | 0.0400 | 0.0780 | 254 |
| 34.0154 | 9 | KIRKYTMRK | HER2/neu.681 | 0.0620 | 0.0055 | 255 |
| 34.0155 | 9 | LVHFLLLKK | MAGE2.116 | 0.5220 | 1.4000 | 256 |
| 34.0156 | 9 | SMLEVFEGK | MAGE2.226 | 0.0950 | 1.6000 | 257 |
| 34.0157 | 9 | SSFSTTINK | MAGE2.69 | 0.1600 | 2.0000 | 258 |
| 34.0158 | 9 | TSYVKVLHK | MAGE2.281 | 0.5300 | 0.1500 | 259 |
| 34.0159 | 9 | VIFSKASEK | MAGE2.149 | 0.4900 | 0.0530 | 260 |
| 34.0160 | 9 | GSVVGNWQK | MAGE3.130 | 0.0040 | 0.2060 | 261 |

TABLE 12-continued

| Peptide | AA | Sequence | Source | A*0301 | A*1101 | SEQ ID NO: |
|---|---|---|---|---|---|---|
| 34.0161 | 9 | SSLPTTMNK | MAGE3.69 | 0.6180 | 0.7100 | 262 |
| 34.0162 | 9 | SVLEVFEGK | MAGE3.226 | 0.1330 | 0.9000 | 263 |
| 34.0171 | 9 | SSBMGGMNK | p53.240 | 0.5440 | 1.1000 | 264 |
| 34.0172 | 9 | SSCMGGMNK | p53.240 | 0.0090 | 0.0490 | 265 |
| 34.0211 | 10 | RTLTLFNVTK | CEA.554 | 0.2200 | 1.3000 | 266 |
| 34.0212 | 10 | TISPLNTSYK | CEA.241 | 0.1800 | 0.0330 | 267 |
| 34.0214 | 10 | STTINYTLWK | MAGE2.72 | 0.0870 | 0.6500 | 268 |
| 34.0215 | 10 | ASSLPTTMNK | MAGE3.68 | 0.0420 | 0.0270 | 269 |
| 34.0225 | 10 | KTYQGSYGFK | p53.101 | 0.4900 | 0.4200 | 270 |
| 34.0226 | 10 | VVRRBPHHEK | p53.172 | 0.1800 | 0.2100 | 271 |
| 34.0228 | 10 | GLAPPQHLIK | p53.187 | 0.0570 | 0.0160 | 272 |
| 34.0229 | 10 | NSSCMGGMNK | p53.239 | 0.0071 | 0.0290 | 273 |
| 34.0230 | 10 | SSBMGGMNRK | p53.240 | 0.0420 | 0.1600 | 274 |
| 34.0232 | 10 | RVCACPGRDK | p53.273 | 0.0190 | 0.0250 | 275 |
| 34.0295 | 11 | KTITVSAELPK | CEA.492 | 0.3600 | 0.1600 | 276 |
| 34.0296 | 11 | TTITVYAEPPK | CEA.314 | 0.0200 | 0.0280 | 277 |
| 34.0298 | 11 | PTISPSYTYYR | CEA.418 | (0.0002) | 0.1300 | 278 |
| 34.0301 | 11 | GLLGDNQVMPK | MAGE2.188 | 0.0780 | 0.0047 | 279 |
| 34.0306 | 11 | MVELVHFLLLK | MAGE2.113 | 0.0200 | 0.0120 | 280 |
| 34.0308 | 11 | FSTTINYTLWR | MAGE2.71 | 0.0110 | 0.0170 | 281 |
| 34.0311 | 11 | GLLGDNQIMPK | MAGE3.188 | 0.1300 | 0.0570 | 282 |
| 34.0317 | 11 | RLGFLHSGTAK | p53.110 | 0.0430 | 0.0001 | 283 |
| 34.0318 | 11 | ALNKMFCQLAK | p53.129 | 0.4400 | 0.0420 | 284 |
| 34.0323 | 11 | RVCACPGRDRR | p53.273 | 0.0290 | 0.0290 | 285 |
| 34.0324 | 11 | LSQETFSDLWK | p53.14 | (0.0009) | 0.0470 | 286 |
| 34.0328 | 11 | RAHSSHLKSKK | p53.363 | 0.0270 | 0.0038 | 287 |
| 34.0329 | 11 | VTCTYSPALNK | p53.122 | 0.0700 | 0.1200 | 288 |
| 34.0330 | 11 | GTRVRAMAIYK | p53.154 | 1.1000 | 0.3300 | 289 |
| 34.0332 | 11 | STSRHKKLMFK | p53.376 | 0.3100 | 0.1300 | 290 |
| 40.0107 | 9 | LAARNVLVK | Her2/neu.846 | 0.0580 | 0.0285 | 291 |
| 40.0109 | 9 | MALESILRR | Her2/neu.889 | 0.0034 | 0.0237 | 292 |
| 40.0145 | 10 | ISWLGLRSLR | Her2/neu.450 | 0.0410 | 0.0027 | 293 |
| 40.0147 | 10 | GSGAFGTVYK | Her2/neu.727 | 0.0660 | 0.1300 | 294 |
| 40.0153 | 10 | ASPLDSTFYR | Her2/neu.997 | 0.0003 | 0.0670 | 295 |

EXAMPLE 3

Identification of Immunogenic Peptides

Using the B7-like supermotifs identified in the related applications described above, sequences from various pathogens and tumor-related proteins were analyzed for the presence of these motifs. Screening was carried out described in the related applications. Table 13 provides the results of searches of the antigens.

TABLE 13

| Peptide | Sequence | Source | SEQ ID NO: |
|---|---|---|---|
| 40.0013 | SPGLSAGI | CEA.680I8 | 296 |
| 40.0022 | KPYDGIPA | Her2/neu.921 | 297 |
| 40.0023 | KPYDGIPI | Her2/neu.921I8 | 298 |
| 40.0050 | APRMPEAA | p53.63 | 299 |
| 40.0051 | APRMPEAI | p53.63I8 | 300 |
| 40.0055 | APAAPTPI | p53.76I8 | 301 |
| 40.0057 | APTPAAPI | p53.79I8 | 302 |
| 40.0059 | TPAAPAPI | p53.81I8 | 303 |
| 40.0061 | APAPAPSI | p53.84I8 | 304 |
| 40.0062 | SPALNKMF | p53.127 | 305 |
| 40.0063 | SPALNKMI | p53.127I8 | 306 |
| 40.0117 | SPSAPPHRI | CEA.3I9 | 307 |
| 40.0119 | PPHRWCIPI | CEA.7I9 | 308 |
| 40.0120 | GPAYSGREI | CEA.92 | 309 |
| 40.0156 | MPNQAQMRILI | Her2/neu.706I10 | 310 |
| 40.0157 | MPYGCLLDHVI | Her2/neu.801I10 | 311 |
| 40.0161 | APPHRWCIPW | CEA.6 | 312 |
| 40.0162 | APPHRWCIPI | CEA.6I10 | 313 |
| 40.0163 | IPWQRLLLTA | CEA.13 | 314 |
| 40.0164 | IPWQRLLLTI | CEA.13I10 | 315 |
| 40.0166 | LPQHLFGYSI | CEA.58I10 | 316 |
| 40.0201 | RPRFRELVSEF | Her2/neu.966 | 317 |
| 40.0202 | RPRFRELVSEI | Her2/neu.966I11 | 318 |
| 40.0205 | PPSPREGPLPA | Her2/neu.1149 | 319 |
| 40.0206 | PPSPREGPLPI | Her2/neu.1149I11 | 320 |
| 40.0207 | GPLPAARPAGA | Her2/neu.1155 | 321 |
| 40.0208 | GPLPAARPAGI | Her2/neu.1155I11 | 322 |
| 40.0231 | APAPAAPTPAA | p53.74 | 323 |
| 40.0232 | APAPAAPTPAI | p53.74I11 | 324 |
| 40.0233 | APAAPTPAAPA | p53.76 | 325 |
| 40.0234 | APAAPTPAAPI | p53.76I11 | 326 |
| 45.0003 | IPWQRLLI | CEA.13.I8 | 327 |
| 45.0004 | LPQHLFGI | CEA.58.I8 | 328 |
| 45.0007 | RPGVNLSI | CEA.428.I8 | 329 |
| 45.0010 | IPQQHTQI | CEA.632.I8 | 330 |
| 45.0011 | TPNNNGTI | CEA.646.I8 | 331 |
| 45.0016 | CPLHNQEI | Her2/neu.315.I8 | 332 |
| 45.0017 | KPCARVCI | Her2/neu.336.I8 | 333 |
| 45.0019 | WPDSLPDI | Her2/neu.415.I8 | 334 |
| 45.0023 | SPYVSRLI | Her2/neu.779.I8 | 335 |
| 45.0024 | VPIKWMAI | Her2/neu.884.I8 | 336 |
| 45.0026 | RPRFRELI | Her2/neu.966.I8 | 337 |
| 45.0028 | APGAGGMI | Her2/neu.1036.I8 | 338 |
| 45.0031 | SPGKNGVI | Her2/neu.1174.I8 | 339 |
| 45.0037 | SPQGASSI | MAGE3.64.I8 | 340 |
| 45.0038 | YPLWSQSI | MAGE3.77.I8 | 341 |
| 45.0044 | SPLPSQAI | p53.33.I8 | 342 |
| 45.0046 | MPEAAPPI | p53.66.I8 | 343 |
| 45.0047 | APAPSWPI | p53.86.I8 | 344 |
| 45.0051 | KPVEDKDAI | CEA.155.I9 | 345 |
| 45.0054 | IPQQHTQVI | CEA.632.I9 | 346 |
| 45.0060 | APPVAPAPI | p53.70.I9 | 347 |
| 45.0062 | APAAPTPAI | p53.76.I9 | 348 |
| 45.0064 | PPGTRVRAI | p53.152.I9 | 349 |
| 45.0065 | APPQHLIRI | p53.189.I9 | 350 |
| 45.0071 | IPQQHTQVLI | CEA.632.I10 | 351 |

TABLE 13-continued

| Peptide | Sequence | Source | SEQ ID NO: |
|---|---|---|---|
| 45.0072 | SPGLSAGATI | CEA.680.I10 | 352 |
| 45.0073 | SPMCKGSRCI | Her2/neu.196.I10 | 353 |
| 45.0074 | MPNPEGRYTI | Her2/neu.282.I10 | 354 |
| 45.0076 | CPLHNQEVTI | Her2/neu.315.I10 | 355 |
| 45.0079 | KPDLSYMPII | Her2/neu.605.I10 | 356 |
| 45.0080 | TPSGAMPNQI | Her2/neu.701.I10 | 357 |
| 45.0084 | GPASPLDSTI | Her2/neu.995.I10 | 358 |
| 45.0091 | APPVAPAPAI | p53.70.I10 | 359 |
| 45.0092 | APAPAAPTPI | p53.74.I10 | 360 |
| 45.0093 | APTPAAPAPI | p53.79.I10 | 361 |
| 45.0094 | APSWPLSSSI | p53.88.I10 | 362 |
| 45.0103 | APTISPLNTSI | CEA.239.I11 | 363 |
| 45.0108 | SPSYTYYRPGI | CEA.421.I11 | 364 |
| 45.0117 | CPSGVKPDLSI | Her2/neu.600.I11 | 365 |
| 45.0118 | SPLTSIISAVI | Her2/neu.649.I11 | 366 |
| 45.0119 | IPDGENVKIPI | Her2/neu.740.I11 | 367 |
| 45.0124 | SPLDSTFYRSI | Her2/neu.998.I11 | 368 |
| 45.0128 | LPAARPAGATI | Her2/neu.1157.I11 | 369 |
| 45.0134 | HPRKLLMQDLI | MAGE2.241.I11 | 370 |
| 45.0135 | GPRALIETSYI | MAGE2.274.I11 | 371 |
| 45.0139 | GPRALVETSYI | MAGE3.274.I11 | 372 |
| 45.0140 | APRMPEAAPPI | p53.63.I11 | 373 |
| 45.0141 | VPSQKTYQGSI | p53.97.I11 | 374 |
| 1145.10 | FPHCLAFAY | HBV POL 541 analog | 375 |
| 1145.09 | FPVCLAFSY | HBV POL 541 analog | 376 |
| 26.0570 | YPALMPLYACI | HBV.pol.645 | 377 |

The above description is provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A composition comprising an immunogenic peptide of less than about 15 amino acids in length that comprises an HLA-A2.1 binding motif, wherein the peptide comprises the p53 sequence of SMPPPGTRV (SEQ ID NO:4).

2. The composition of claim 1, further comprising a pharmaceutically acceptable carrier.

3. The composition of claim 1, further comprising a liposome.

* * * * *

SEQUENCE LISTING

```
<160> NUMBER OF SEQ ID NOS: 380

<210> SEQ ID NO 1
<211> LENGTH: 9
<212> TYPE: PRT
<213> ORGANISM: Artificial Sequence
<220> FEATURE:
<223> OTHER INFORMATION: Flu.24 peptide 17.0317

<400> SEQUENCE: 1

Leu Gln Ile Gly Asn Ile Ile Ser Ile
 1               5

<210> SEQ ID NO 2
<211> LENGTH: 9
<212> TYPE: PRT
<213> ORGANISM: Artificial Sequence
<220> FEATURE:
<223> OTHER INFORMATION: CEA.432 peptide 38.0103

<400> SEQUENCE: 2

Asn Leu Ser Leu Ser Cys His Ala Ala
 1               5

<210> SEQ ID NO 3
<211> LENGTH: 9
<212> TYPE: PRT
<213> ORGANISM: Artificial Sequence
<220> FEATURE:
<223> OTHER INFORMATION: CEA.605V9 peptide 1233.11

<400> SEQUENCE: 3

Tyr Leu Ser Gly Ala Asn Leu Asn Val
 1               5

<210> SEQ ID NO 4
<211> LENGTH: 9
<212> TYPE: PRT
<213> ORGANISM: Artificial Sequence
<220> FEATURE:
<223> OTHER INFORMATION: p53.149M2 peptide 1295.03

<400> SEQUENCE: 4
```

Ser Met Pro Pro Pro Gly Thr Arg Val
1               5

<210> SEQ ID NO 5
<211> LENGTH: 9
<212> TYPE: PRT
<213> ORGANISM: Artificial Sequence
<220> FEATURE:
<223> OTHER INFORMATION: p53.149L2 peptide 1295.04

<400> SEQUENCE: 5

Ser Leu Pro Pro Pro Gly Thr Arg Val
1               5

<210> SEQ ID NO 6
<211> LENGTH: 9
<212> TYPE: PRT
<213> ORGANISM: Artificial Sequence
<220> FEATURE:
<223> OTHER INFORMATION: p53.139 peptide 1317.24

<400> SEQUENCE: 6

Lys Thr Cys Pro Val Gln Leu Trp Val
1               5

<210> SEQ ID NO 7
<211> LENGTH: 9
<212> TYPE: PRT
<213> ORGANISM: Artificial Sequence
<220> FEATURE:
<223> OTHER INFORMATION: p53.24V9 peptide 1323.02

<400> SEQUENCE: 7

Lys Leu Leu Pro Glu Asn Asn Val Val
1               5

<210> SEQ ID NO 8
<211> LENGTH: 9
<212> TYPE: PRT
<213> ORGANISM: Artificial Sequence
<220> FEATURE:
<223> OTHER INFORMATION: p53.129B7V9 peptide 1323.04

<400> SEQUENCE: 8

Ala Leu Asn Lys Met Phe Asx Gln Val
1               5

<210> SEQ ID NO 9
<211> LENGTH: 9
<212> TYPE: PRT
<213> ORGANISM: Artificial Sequence
<220> FEATURE:
<223> OTHER INFORMATION: p53.139L2B3 peptide 1323.06

<400> SEQUENCE: 9

Lys Leu Asx Pro Val Gln Leu Trp Val
1               5

<210> SEQ ID NO 10
<211> LENGTH: 9
<212> TYPE: PRT
<213> ORGANISM: Artificial Sequence
<220> FEATURE:
<223> OTHER INFORMATION: p53.229B1L2V9 peptide 1323.08

<400> SEQUENCE: 10

```
Asx Leu Thr Ile His Tyr Asn Tyr Val
 1               5
```

```
<210> SEQ ID NO 11
<211> LENGTH: 10
<212> TYPE: PRT
<213> ORGANISM: Artificial Sequence
<220> FEATURE:
<223> OTHER INFORMATION: p53.188L2 peptide 1323.18

<400> SEQUENCE: 11

Leu Leu Pro Pro Gln His Leu Ile Arg Val
 1               5                  10
```

```
<210> SEQ ID NO 12
<211> LENGTH: 11
<212> TYPE: PRT
<213> ORGANISM: Artificial Sequence
<220> FEATURE:
<223> OTHER INFORMATION: p53.236 peptide 1323.29

<400> SEQUENCE: 12

Tyr Met Cys Asn Ser Ser Cys Met Gly Gly Met
 1               5                  10
```

```
<210> SEQ ID NO 13
<211> LENGTH: 11
<212> TYPE: PRT
<213> ORGANISM: Artificial Sequence
<220> FEATURE:
<223> OTHER INFORMATION: p53.236L2V11 peptide 1323.31

<400> SEQUENCE: 13

Tyr Leu Cys Asn Ser Ser Cys Met Gly Gly Val
 1               5                  10
```

```
<210> SEQ ID NO 14
<211> LENGTH: 11
<212> TYPE: PRT
<213> ORGANISM: Artificial Sequence
<220> FEATURE:
<223> OTHER INFORMATION: p53.101L2V11 peptide 1323.34

<400> SEQUENCE: 14

Lys Leu Tyr Gln Gly Ser Tyr Gly Phe Arg Val
 1               5                  10
```

```
<210> SEQ ID NO 15
<211> LENGTH: 9
<212> TYPE: PRT
<213> ORGANISM: Artificial Sequence
<220> FEATURE:
<223> OTHER INFORMATION: p53.135 peptide 1324.07

<400> SEQUENCE: 15

Cys Gln Leu Ala Lys Thr Cys Pro Val
 1               5
```

```
<210> SEQ ID NO 16
<211> LENGTH: 9
<212> TYPE: PRT
<213> ORGANISM: Artificial Sequence
<220> FEATURE:
<223> OTHER INFORMATION: p53.65L2 peptide 1325.01

<400> SEQUENCE: 16

Arg Leu Pro Glu Ala Ala Pro Pro Val
```

-continued

```
<210> SEQ ID NO 17
<211> LENGTH: 9
<212> TYPE: PRT
<213> ORGANISM: Artificial Sequence
<220> FEATURE:
<223> OTHER INFORMATION: p53.187V9 peptide 1325.02

<400> SEQUENCE: 17

Gly Leu Ala Pro Pro Gln His Leu Val
 1               5

<210> SEQ ID NO 18
<211> LENGTH: 9
<212> TYPE: PRT
<213> ORGANISM: Artificial Sequence
<220> FEATURE:
<223> OTHER INFORMATION: MAGE3.112M2 peptide 1325.04

<400> SEQUENCE: 18

Lys Met Ala Glu Leu Val His Phe Leu
 1               5

<210> SEQ ID NO 19
<211> LENGTH: 9
<212> TYPE: PRT
<213> ORGANISM: Artificial Sequence
<220> FEATURE:
<223> OTHER INFORMATION: MAGE3.112L2 peptide 1325.05

<400> SEQUENCE: 19

Lys Leu Ala Glu Leu Val His Phe Leu
 1               5

<210> SEQ ID NO 20
<211> LENGTH: 9
<212> TYPE: PRT
<213> ORGANISM: Artificial Sequence
<220> FEATURE:
<223> OTHER INFORMATION: p53.135L2 peptide 1326.01

<400> SEQUENCE: 20

Cys Leu Leu Ala Lys Thr Cys Pro Val
 1               5

<210> SEQ ID NO 21
<211> LENGTH: 9
<212> TYPE: PRT
<213> ORGANISM: Artificial Sequence
<220> FEATURE:
<223> OTHER INFORMATION: p53.164L2 peptide 1326.02

<400> SEQUENCE: 21

Lys Leu Ser Gln His Met Thr Glu Val
 1               5

<210> SEQ ID NO 22
<211> LENGTH: 9
<212> TYPE: PRT
<213> ORGANISM: Artificial Sequence
<220> FEATURE:
<223> OTHER INFORMATION: p53.68L2V9 peptide 1326.04

<400> SEQUENCE: 22

Glu Leu Ala Pro Val Val Ala Pro Val
 1               5
```

<210> SEQ ID NO 23
<211> LENGTH: 10
<212> TYPE: PRT
<213> ORGANISM: Artificial Sequence
<220> FEATURE:
<223> OTHER INFORMATION: p53.136 peptide 1326.06

<400> SEQUENCE: 23

Gln Leu Ala Lys Thr Cys Pro Val Gln Val
 1               5                  10

<210> SEQ ID NO 24
<211> LENGTH: 9
<212> TYPE: PRT
<213> ORGANISM: Artificial Sequence
<220> FEATURE:
<223> OTHER INFORMATION: p53.168L2 peptide 1326.08

<400> SEQUENCE: 24

His Leu Thr Glu Val Val Arg Arg Val
 1               5

<210> SEQ ID NO 25
<211> LENGTH: 11
<212> TYPE: PRT
<213> ORGANISM: Artificial Sequence
<220> FEATURE:
<223> OTHER INFORMATION: peptide 1329.01

<400> SEQUENCE: 25

Lys Thr Tyr Gln Gly Ser Tyr Gly Phe Arg Leu
 1               5                  10

<210> SEQ ID NO 26
<211> LENGTH: 10
<212> TYPE: PRT
<213> ORGANISM: Artificial Sequence
<220> FEATURE:
<223> OTHER INFORMATION: p53.216 peptide 1329.03

<400> SEQUENCE: 26

Val Val Val Pro Tyr Glu Pro Pro Glu Val
 1               5                  10

<210> SEQ ID NO 27
<211> LENGTH: 9
<212> TYPE: PRT
<213> ORGANISM: Artificial Sequence
<220> FEATURE:
<223> OTHER INFORMATION: p53.135B1B7 peptide 1329.14

<400> SEQUENCE: 27

Asx Gln Leu Ala Lys Thr Asx Pro Val
 1               5

<210> SEQ ID NO 28
<211> LENGTH: 9
<212> TYPE: PRT
<213> ORGANISM: Artificial Sequence
<220> FEATURE:
<223> OTHER INFORMATION: p53.135B1L2B7 peptide 1329.15

<400> SEQUENCE: 28

Asx Leu Leu Ala Lys Thr Asx Pro Val
 1               5

```
<210> SEQ ID NO 29
<211> LENGTH: 9
<212> TYPE: PRT
<213> ORGANISM: Artificial Sequence
<220> FEATURE:
<223> OTHER INFORMATION: CEA.78 peptide 1330.01

<400> SEQUENCE: 29

Gln Ile Ile Gly Tyr Val Ile Gly Thr
1               5

<210> SEQ ID NO 30
<211> LENGTH: 9
<212> TYPE: PRT
<213> ORGANISM: Artificial Sequence
<220> FEATURE:
<223> OTHER INFORMATION: CEA.78L2V9 peptide 1330.02

<400> SEQUENCE: 30

Gln Leu Ile Gly Tyr Val Ile Gly Val
1               5

<210> SEQ ID NO 31
<211> LENGTH: 9
<212> TYPE: PRT
<213> ORGANISM: Artificial Sequence
<220> FEATURE:
<223> OTHER INFORMATION: CEA.569 peptide 1330.05

<400> SEQUENCE: 31

Tyr Val Cys Gly Ile Gln Asn Ser Val
1               5

<210> SEQ ID NO 32
<211> LENGTH: 9
<212> TYPE: PRT
<213> ORGANISM: Artificial Sequence
<220> FEATURE:
<223> OTHER INFORMATION: CEA.569L2 peptide 1330.06

<400> SEQUENCE: 32

Tyr Leu Cys Gly Ile Gln Asn Ser Val
1               5

<210> SEQ ID NO 33
<211> LENGTH: 9
<212> TYPE: PRT
<213> ORGANISM: Artificial Sequence
<220> FEATURE:
<223> OTHER INFORMATION: CEA.687 peptide 1330.07

<400> SEQUENCE: 33

Ala Thr Val Gly Ile Met Ile Gly Val
1               5

<210> SEQ ID NO 34
<211> LENGTH: 9
<212> TYPE: PRT
<213> ORGANISM: Artificial Sequence
<220> FEATURE:
<223> OTHER INFORMATION: CEA.687L2 peptide 1330.08

<400> SEQUENCE: 34

Ala Leu Val Gly Ile Met Ile Gly Val
1               5
```

```
<210> SEQ ID NO 35
<211> LENGTH: 10
<212> TYPE: PRT
<213> ORGANISM: Artificial Sequence
<220> FEATURE:
<223> OTHER INFORMATION: CEA.411 peptide 1330.09

<400> SEQUENCE: 35

Val Leu Tyr Gly Pro Asp Asp Pro Thr Ile
 1               5                  10

<210> SEQ ID NO 36
<211> LENGTH: 10
<212> TYPE: PRT
<213> ORGANISM: Artificial Sequence
<220> FEATURE:
<223> OTHER INFORMATION: CEA.411V10 peptide 1330.10

<400> SEQUENCE: 36

Val Leu Tyr Gly Pro Asp Asp Pro Thr Val
 1               5                  10

<210> SEQ ID NO 37
<211> LENGTH: 9
<212> TYPE: PRT
<213> ORGANISM: Artificial Sequence
<220> FEATURE:
<223> OTHER INFORMATION: p53.42V9 peptide 1331.02

<400> SEQUENCE: 37

Asp Leu Met Leu Ser Pro Asp Asp Val
 1               5

<210> SEQ ID NO 38
<211> LENGTH: 9
<212> TYPE: PRT
<213> ORGANISM: Artificial Sequence
<220> FEATURE:
<223> OTHER INFORMATION: p53.42A1 peptide 1331.03

<400> SEQUENCE: 38

Ala Leu Met Leu Ser Pro Asp Asp Ile
 1               5

<210> SEQ ID NO 39
<211> LENGTH: 9
<212> TYPE: PRT
<213> ORGANISM: Artificial Sequence
<220> FEATURE:
<223> OTHER INFORMATION: p53.42A1V9 peptide 1331.04

<400> SEQUENCE: 39

Ala Leu Met Leu Ser Pro Asp Asp Val
 1               5

<210> SEQ ID NO 40
<211> LENGTH: 9
<212> TYPE: PRT
<213> ORGANISM: Artificial Sequence
<220> FEATURE:
<223> OTHER INFORMATION: p53.42A7 peptide 1331.05

<400> SEQUENCE: 40

Asp Leu Met Leu Ser Pro Ala Asp Ile
 1               5

<210> SEQ ID NO 41
```

```
<211> LENGTH: 9
<212> TYPE: PRT
<213> ORGANISM: Artificial Sequence
<220> FEATURE:
<223> OTHER INFORMATION: p53.42A7V9 peptide 1331.06

<400> SEQUENCE: 41

Asp Leu Met Leu Ser Pro Ala Asp Val
 1               5

<210> SEQ ID NO 42
<211> LENGTH: 9
<212> TYPE: PRT
<213> ORGANISM: Artificial Sequence
<220> FEATURE:
<223> OTHER INFORMATION: p53.42A8 peptide 1331.07

<400> SEQUENCE: 42

Asp Leu Met Leu Ser Pro Asp Ala Ile
 1               5

<210> SEQ ID NO 43
<211> LENGTH: 9
<212> TYPE: PRT
<213> ORGANISM: Artificial Sequence
<220> FEATURE:
<223> OTHER INFORMATION: p53.42A8V9 peptide 1331.08

<400> SEQUENCE: 43

Asp Leu Met Leu Ser Pro Asp Ala Val
 1               5

<210> SEQ ID NO 44
<211> LENGTH: 9
<212> TYPE: PRT
<213> ORGANISM: Artificial Sequence
<220> FEATURE:
<223> OTHER INFORMATION: KSHV.89 peptide 38.0007

<400> SEQUENCE: 44

Ala Ile Leu Thr Phe Gly Ser Phe Val
 1               5

<210> SEQ ID NO 45
<211> LENGTH: 9
<212> TYPE: PRT
<213> ORGANISM: Artificial Sequence
<220> FEATURE:
<223> OTHER INFORMATION: KSHV.106 peptide 38.0009

<400> SEQUENCE: 45

His Leu Arg Asp Phe Ala Leu Ala Val
 1               5

<210> SEQ ID NO 46
<211> LENGTH: 9
<212> TYPE: PRT
<213> ORGANISM: Artificial Sequence
<220> FEATURE:
<223> OTHER INFORMATION: KSHV.155 peptide 38.0015

<400> SEQUENCE: 46

Ala Leu Leu Gly Ser Ile Ala Leu Leu
 1               5

<210> SEQ ID NO 47
<211> LENGTH: 9
```

```
<212> TYPE: PRT
<213> ORGANISM: Artificial Sequence
<220> FEATURE:
<223> OTHER INFORMATION: KSHV.161 peptide 38.0018

<400> SEQUENCE: 47

Ala Leu Leu Ala Thr Ile Leu Ala Ala
 1               5

<210> SEQ ID NO 48
<211> LENGTH: 9
<212> TYPE: PRT
<213> ORGANISM: Artificial Sequence
<220> FEATURE:
<223> OTHER INFORMATION: KSHV.162 peptide 38.0019

<400> SEQUENCE: 48

Leu Leu Ala Thr Ile Leu Ala Ala Val
 1               5

<210> SEQ ID NO 49
<211> LENGTH: 9
<212> TYPE: PRT
<213> ORGANISM: Artificial Sequence
<220> FEATURE:
<223> OTHER INFORMATION: KSHV.14 peptide 38.0022

<400> SEQUENCE: 49

Arg Leu Phe Ala Asp Glu Leu Ala Ala
 1               5

<210> SEQ ID NO 50
<211> LENGTH: 9
<212> TYPE: PRT
<213> ORGANISM: Artificial Sequence
<220> FEATURE:
<223> OTHER INFORMATION: KSHV.65 peptide 38.0024

<400> SEQUENCE: 50

Tyr Leu Ser Lys Cys Thr Leu Ala Val
 1               5

<210> SEQ ID NO 51
<211> LENGTH: 9
<212> TYPE: PRT
<213> ORGANISM: Artificial Sequence
<220> FEATURE:
<223> OTHER INFORMATION: KSHV.153 peptide 38.0026

<400> SEQUENCE: 51

Leu Val Tyr His Ile Tyr Ser Lys Ile
 1               5

<210> SEQ ID NO 52
<211> LENGTH: 9
<212> TYPE: PRT
<213> ORGANISM: Artificial Sequence
<220> FEATURE:
<223> OTHER INFORMATION: KSHV.208 peptide 38.0029

<400> SEQUENCE: 52

Ser Met Tyr Leu Cys Ile Leu Ser Ala
 1               5

<210> SEQ ID NO 53
<211> LENGTH: 9
<212> TYPE: PRT
```

```
<213> ORGANISM: Artificial Sequence
<220> FEATURE:
<223> OTHER INFORMATION: KSHV.210 peptide 38.0030

<400> SEQUENCE: 53

Tyr Leu Cys Ile Leu Ser Ala Leu Val
1               5

<210> SEQ ID NO 54
<211> LENGTH: 9
<212> TYPE: PRT
<213> ORGANISM: Artificial Sequence
<220> FEATURE:
<223> OTHER INFORMATION: KSHV.268 peptide 38.0033

<400> SEQUENCE: 54

Val Met Phe Ser Tyr Leu Gln Ser Leu
1               5

<210> SEQ ID NO 55
<211> LENGTH: 9
<212> TYPE: PRT
<213> ORGANISM: Artificial Sequence
<220> FEATURE:
<223> OTHER INFORMATION: KSHV.285 peptide 38.0035

<400> SEQUENCE: 55

Arg Leu His Val Tyr Ala Tyr Ser Ala
1               5

<210> SEQ ID NO 56
<211> LENGTH: 9
<212> TYPE: PRT
<213> ORGANISM: Artificial Sequence
<220> FEATURE:
<223> OTHER INFORMATION: KSHV.98 peptide 38.0039

<400> SEQUENCE: 56

Gly Leu Gln Thr Leu Gly Ala Phe Val
1               5

<210> SEQ ID NO 57
<211> LENGTH: 9
<212> TYPE: PRT
<213> ORGANISM: Artificial Sequence
<220> FEATURE:
<223> OTHER INFORMATION: KSHV.105 peptide 38.0040

<400> SEQUENCE: 57

Phe Val Glu Glu Gln Met Thr Trp Ala
1               5

<210> SEQ ID NO 58
<211> LENGTH: 9
<212> TYPE: PRT
<213> ORGANISM: Artificial Sequence
<220> FEATURE:
<223> OTHER INFORMATION: KSHV.109 peptide 38.0041

<400> SEQUENCE: 58

Gln Met Thr Trp Ala Gln Thr Val Val
1               5

<210> SEQ ID NO 59
<211> LENGTH: 9
<212> TYPE: PRT
<213> ORGANISM: Artificial Sequence
```

```
<220> FEATURE:
<223> OTHER INFORMATION: KSHV.130 peptide 38.0042

<400> SEQUENCE: 59

Ile Ile Leu Asp Thr Ala Ile Phe Val
 1               5

<210> SEQ ID NO 60
<211> LENGTH: 9
<212> TYPE: PRT
<213> ORGANISM: Artificial Sequence
<220> FEATURE:
<223> OTHER INFORMATION: KSHV.135 peptide 38.0043

<400> SEQUENCE: 60

Ala Ile Phe Val Cys Asn Ala Phe Val
 1               5

<210> SEQ ID NO 61
<211> LENGTH: 9
<212> TYPE: PRT
<213> ORGANISM: Artificial Sequence
<220> FEATURE:
<223> OTHER INFORMATION: KSHV.172 peptide 38.0046

<400> SEQUENCE: 61

Ala Met Gly Asn Arg Leu Val Glu Ala
 1               5

<210> SEQ ID NO 62
<211> LENGTH: 9
<212> TYPE: PRT
<213> ORGANISM: Artificial Sequence
<220> FEATURE:
<223> OTHER INFORMATION: KSHV.176 peptide 38.0047

<400> SEQUENCE: 62

Arg Leu Val Glu Ala Cys Asn Leu Leu
 1               5

<210> SEQ ID NO 63
<211> LENGTH: 9
<212> TYPE: PRT
<213> ORGANISM: Artificial Sequence
<220> FEATURE:
<223> OTHER INFORMATION: KSHV.198 peptide 38.0059

<400> SEQUENCE: 63

Thr Leu Ser Ile Val Thr Phe Ser Leu
 1               5

<210> SEQ ID NO 64
<211> LENGTH: 9
<212> TYPE: PRT
<213> ORGANISM: Artificial Sequence
<220> FEATURE:
<223> OTHER INFORMATION: KSHV.292 peptide 38.0063

<400> SEQUENCE: 64

Lys Leu Ser Val Leu Leu Leu Glu Val
 1               5

<210> SEQ ID NO 65
<211> LENGTH: 9
<212> TYPE: PRT
<213> ORGANISM: Artificial Sequence
<220> FEATURE:
```

<223> OTHER INFORMATION: KSHV.296 peptide 38.0064

<400> SEQUENCE: 65

Leu Leu Leu Glu Val Asn Arg Ser Val
1               5

<210> SEQ ID NO 66
<211> LENGTH: 9
<212> TYPE: PRT
<213> ORGANISM: Artificial Sequence
<220> FEATURE:
<223> OTHER INFORMATION: KSHV.78 peptide 38.0068

<400> SEQUENCE: 66

Phe Val Ser Ser Pro Thr Leu Pro Val
1               5

<210> SEQ ID NO 67
<211> LENGTH: 9
<212> TYPE: PRT
<213> ORGANISM: Artificial Sequence
<220> FEATURE:
<223> OTHER INFORMATION: KSHV.281 peptide 38.0070

<400> SEQUENCE: 67

Ala Met Leu Val Leu Leu Ala Glu Ile
1               5

<210> SEQ ID NO 68
<211> LENGTH: 9
<212> TYPE: PRT
<213> ORGANISM: Artificial Sequence
<220> FEATURE:
<223> OTHER INFORMATION: KSHV.1116 peptide 38.0075

<400> SEQUENCE: 68

Gln Met Ala Arg Leu Ala Trp Glu Ala
1               5

<210> SEQ ID NO 69
<211> LENGTH: 10
<212> TYPE: PRT
<213> ORGANISM: Artificial Sequence
<220> FEATURE:
<223> OTHER INFORMATION: KSHV.10 peptide 38.0131

<400> SEQUENCE: 69

Val Leu Ala Ile Glu Gly Ile Phe Met Ala
1               5                   10

<210> SEQ ID NO 70
<211> LENGTH: 10
<212> TYPE: PRT
<213> ORGANISM: Artificial Sequence
<220> FEATURE:
<223> OTHER INFORMATION: KSHV.27 peptide 38.0132

<400> SEQUENCE: 70

Tyr Leu Tyr His Pro Leu Leu Ser Pro Ile
1               5                   10

<210> SEQ ID NO 71
<211> LENGTH: 10
<212> TYPE: PRT
<213> ORGANISM: Artificial Sequence
<220> FEATURE:
<223> OTHER INFORMATION: KSHV.49 peptide 38.0134

-continued

```
<400> SEQUENCE: 71

Ser Leu Phe Glu Ala Met Leu Ala Asn Val
1               5                   10

<210> SEQ ID NO 72
<211> LENGTH: 10
<212> TYPE: PRT
<213> ORGANISM: Artificial Sequence
<220> FEATURE:
<223> OTHER INFORMATION: KSHV.62 peptide 38.0135

<400> SEQUENCE: 72

Ser Thr Thr Gly Ile Asn Gln Leu Gly Leu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: KSHV.88 peptide 38.0137

<400> SEQUENCE: 73

Leu Ala Ile Leu Thr Phe Gly Ser Phe Val
1               5                   10

<210> SEQ ID NO 74
<211> LENGTH: 10
<212> TYPE: PRT
<213> ORGANISM: Artificial Sequence
<220> FEATURE:
<223> OTHER INFORMATION: KSHV.155 peptide 38.0139

<400> SEQUENCE: 74

Ala Leu Leu Gly Ser Ile Ala Leu Leu Ala
1               5                   10

<210> SEQ ID NO 75
<211> LENGTH: 10
<212> TYPE: PRT
<213> ORGANISM: Artificial Sequence
<220> FEATURE:
<223> OTHER INFORMATION: KSHV.161 peptide 38.0141

<400> SEQUENCE: 75

Ala Leu Leu Ala Thr Ile Leu Ala Ala Val
1               5                   10

<210> SEQ ID NO 76
<211> LENGTH: 10
<212> TYPE: PRT
<213> ORGANISM: Artificial Sequence
<220> FEATURE:
<223> OTHER INFORMATION: KSHV.162 peptide 38.0142

<400> SEQUENCE: 76

Leu Leu Ala Thr Ile Leu Ala Ala Val Ala
1               5                   10

<210> SEQ ID NO 77
<211> LENGTH: 10
<212> TYPE: PRT
<213> ORGANISM: Artificial Sequence
<220> FEATURE:
<223> OTHER INFORMATION: KSHV.14 peptide 38.0143
```

-continued

```
<400> SEQUENCE: 77

Arg Leu Phe Ala Asp Glu Leu Ala Ala Leu
1               5                   10

<210> SEQ ID NO 78
<211> LENGTH: 10
<212> TYPE: PRT
<213> ORGANISM: Artificial Sequence
<220> FEATURE:
<223> OTHER INFORMATION: KSHV.65 peptide 38.0148

<400> SEQUENCE: 78

Tyr Leu Ser Lys Cys Thr Leu Ala Val Leu
1               5                   10

<210> SEQ ID NO 79
<211> LENGTH: 10
<212> TYPE: PRT
<213> ORGANISM: Artificial Sequence
<220> FEATURE:
<223> OTHER INFORMATION: KSHV.152 peptide 38.0150

<400> SEQUENCE: 79

Leu Leu Val Tyr His Ile Tyr Ser Lys Ile
1               5                   10

<210> SEQ ID NO 80
<211> LENGTH: 10
<212> TYPE: PRT
<213> ORGANISM: Artificial Sequence
<220> FEATURE:
<223> OTHER INFORMATION: KSHV.208 peptide 38.0151

<400> SEQUENCE: 80

Ser Met Tyr Leu Cys Ile Leu Ser Ala Leu
1               5                   10

<210> SEQ ID NO 81
<211> LENGTH: 10
<212> TYPE: PRT
<213> ORGANISM: Artificial Sequence
<220> FEATURE:
<223> OTHER INFORMATION: KSHV.68 peptide 38.0153

<400> SEQUENCE: 81

His Leu His Arg Gln Met Leu Ser Phe Val
1               5                   10

<210> SEQ ID NO 82
<211> LENGTH: 10
<212> TYPE: PRT
<213> ORGANISM: Artificial Sequence
<220> FEATURE:
<223> OTHER INFORMATION: KSHV.167 peptide 38.0163

<400> SEQUENCE: 82

Leu Leu Cys Gly Lys Thr Gly Ala Phe Leu
1               5                   10

<210> SEQ ID NO 83
<211> LENGTH: 10
<212> TYPE: PRT
<213> ORGANISM: Artificial Sequence
<220> FEATURE:
<223> OTHER INFORMATION: KSHV.197 peptide 38.0164

<400> SEQUENCE: 83
```

Glu Thr Leu Ser Ile Val Thr Phe Ser Leu
1               5                   10

<210> SEQ ID NO 84
<211> LENGTH: 9
<212> TYPE: PRT
<213> ORGANISM: Artificial Sequence
<220> FEATURE:
<223> OTHER INFORMATION: mp53.119 peptide 39.0063

<400> SEQUENCE: 84

Val Met Cys Thr Tyr Ser Pro Pro Leu
1               5

<210> SEQ ID NO 85
<211> LENGTH: 9
<212> TYPE: PRT
<213> ORGANISM: Artificial Sequence
<220> FEATURE:
<223> OTHER INFORMATION: mp53.129 peptide 39.0065

<400> SEQUENCE: 85

Lys Leu Phe Cys Gln Leu Ala Lys Thr
1               5

<210> SEQ ID NO 86
<211> LENGTH: 9
<212> TYPE: PRT
<213> ORGANISM: Artificial Sequence
<220> FEATURE:
<223> OTHER INFORMATION: mp53.146 peptide 39.0067

<400> SEQUENCE: 86

Ala Thr Pro Pro Ala Gly Ser Arg Val
1               5

<210> SEQ ID NO 87
<211> LENGTH: 10
<212> TYPE: PRT
<213> ORGANISM: Artificial Sequence
<220> FEATURE:
<223> OTHER INFORMATION: mp53.110 peptide 39.0133

<400> SEQUENCE: 87

Phe Leu Gln Ser Gly Thr Ala Lys Ser Val
1               5                   10

<210> SEQ ID NO 88
<211> LENGTH: 10
<212> TYPE: PRT
<213> ORGANISM: Artificial Sequence
<220> FEATURE:
<223> OTHER INFORMATION: KSHV.311 peptide 39.0169

<400> SEQUENCE: 88

Cys Met Asp Arg Gly Leu Thr Val Phe Val
1               5                   10

<210> SEQ ID NO 89
<211> LENGTH: 10
<212> TYPE: PRT
<213> ORGANISM: Artificial Sequence
<220> FEATURE:
<223> OTHER INFORMATION: KSHV.327 peptide 39.0170

<400> SEQUENCE: 89

Val Leu Leu Asn Trp Trp Arg Trp Arg Leu
1               5                   10

<210> SEQ ID NO 90
<211> LENGTH: 9
<212> TYPE: PRT
<213> ORGANISM: Artificial Sequence
<220> FEATURE:
<223> OTHER INFORMATION: HCV.1565 peptide 40.0070

<400> SEQUENCE: 90

Gly Val Phe Thr Gly Leu Thr His Ile
1               5

<210> SEQ ID NO 91
<211> LENGTH: 9
<212> TYPE: PRT
<213> ORGANISM: Artificial Sequence
<220> FEATURE:
<223> OTHER INFORMATION: HCV.1611 peptide 40.0072

<400> SEQUENCE: 91

Gln Met Trp Lys Cys Leu Ile Arg Leu
1               5

<210> SEQ ID NO 92
<211> LENGTH: 9
<212> TYPE: PRT
<213> ORGANISM: Artificial Sequence
<220> FEATURE:
<223> OTHER INFORMATION: HCV.1650 peptide 40.0074

<400> SEQUENCE: 92

Ile Met Thr Cys Met Ser Ala Asp Leu
1               5

<210> SEQ ID NO 93
<211> LENGTH: 9
<212> TYPE: PRT
<213> ORGANISM: Artificial Sequence
<220> FEATURE:
<223> OTHER INFORMATION: HCV.1674 peptide 40.0076

<400> SEQUENCE: 93

Ala Leu Ala Ala Tyr Cys Leu Ser Thr
1               5

<210> SEQ ID NO 94
<211> LENGTH: 9
<212> TYPE: PRT
<213> ORGANISM: Artificial Sequence
<220> FEATURE:
<223> OTHER INFORMATION: HCV.1692 peptide 40.0080

<400> SEQUENCE: 94

Val Leu Ser Gly Lys Pro Ala Ile Ile
1               5

<210> SEQ ID NO 95
<211> LENGTH: 9
<212> TYPE: PRT
<213> ORGANISM: Artificial Sequence
<220> FEATURE:
<223> OTHER INFORMATION: HCV.1773 peptide 40.0082

<400> SEQUENCE: 95

Phe Ile Ser Gly Ile Gln Tyr Leu Ala

-continued

<210> SEQ ID NO 96
<211> LENGTH: 10
<212> TYPE: PRT
<213> ORGANISM: Artificial Sequence
<220> FEATURE:
<223> OTHER INFORMATION: HCV.1649 peptide 40.0134

<400> SEQUENCE: 96

Tyr Ile Met Thr Cys Met Ser Ala Asp Leu
1               5                   10

<210> SEQ ID NO 97
<211> LENGTH: 10
<212> TYPE: PRT
<213> ORGANISM: Artificial Sequence
<220> FEATURE:
<223> OTHER INFORMATION: HCV.1791 peptide 40.0137

<400> SEQUENCE: 97

Ala Ile Ala Ser Leu Met Ala Phe Thr Ala
1               5                   10

<210> SEQ ID NO 98
<211> LENGTH: 10
<212> TYPE: PRT
<213> ORGANISM: Artificial Sequence
<220> FEATURE:
<223> OTHER INFORMATION: HCV.1838 peptide 40.0138

<400> SEQUENCE: 98

Gly Leu Ala Gly Ala Ala Ile Gly Ser Val
1               5                   10

<210> SEQ ID NO 99
<211> LENGTH: 8
<212> TYPE: PRT
<213> ORGANISM: Artificial Sequence
<220> FEATURE:
<223> OTHER INFORMATION: CEA.692 peptide 41.0058

<400> SEQUENCE: 99

Met Ile Gly Val Leu Val Gly Val
1               5

<210> SEQ ID NO 100
<211> LENGTH: 9
<212> TYPE: PRT
<213> ORGANISM: Artificial Sequence
<220> FEATURE:
<223> OTHER INFORMATION: TRP1 peptide 41.0061

<400> SEQUENCE: 100

Val Leu Pro Leu Ala Tyr Ile Ser Leu
1               5

<210> SEQ ID NO 101
<211> LENGTH: 9
<212> TYPE: PRT
<213> ORGANISM: Artificial Sequence
<220> FEATURE:
<223> OTHER INFORMATION: TRP1 peptide 41.0062

<400> SEQUENCE: 101

Ser Leu Gly Cys Ile Phe Phe Pro Leu
1               5

<210> SEQ ID NO 102
<211> LENGTH: 9
<212> TYPE: PRT
<213> ORGANISM: Artificial Sequence
<220> FEATURE:
<223> OTHER INFORMATION: TRP1 peptide 41.0063

<400> SEQUENCE: 102

Pro Leu Ala Tyr Ile Ser Leu Phe Leu
1               5

<210> SEQ ID NO 103
<211> LENGTH: 9
<212> TYPE: PRT
<213> ORGANISM: Artificial Sequence
<220> FEATURE:
<223> OTHER INFORMATION: TRP1 peptide 41.0065

<400> SEQUENCE: 103

Leu Met Leu Phe Tyr Gln Val Trp Ala
1               5

<210> SEQ ID NO 104
<211> LENGTH: 9
<212> TYPE: PRT
<213> ORGANISM: Artificial Sequence
<220> FEATURE:
<223> OTHER INFORMATION: TRP1 peptide 41.0071

<400> SEQUENCE: 104

Asn Ile Ser Ile Tyr Asn Tyr Phe Val
1               5

<210> SEQ ID NO 105
<211> LENGTH: 9
<212> TYPE: PRT
<213> ORGANISM: Artificial Sequence
<220> FEATURE:
<223> OTHER INFORMATION: TRP1 peptide 41.0072

<400> SEQUENCE: 105

Asn Ile Ser Val Tyr Asn Tyr Phe Val
1               5

<210> SEQ ID NO 106
<211> LENGTH: 9
<212> TYPE: PRT
<213> ORGANISM: Artificial Sequence
<220> FEATURE:
<223> OTHER INFORMATION: TRP1 peptide 41.0075

<400> SEQUENCE: 106

Phe Val Trp Thr His Tyr Tyr Ser Val
1               5

<210> SEQ ID NO 107
<211> LENGTH: 9
<212> TYPE: PRT
<213> ORGANISM: Artificial Sequence
<220> FEATURE:
<223> OTHER INFORMATION: TRP1 peptide 41.0077

<400> SEQUENCE: 107

Phe Leu Thr Trp His Arg Tyr His Leu
1               5

<210> SEQ ID NO 108
<211> LENGTH: 9
<212> TYPE: PRT
<213> ORGANISM: Artificial Sequence
<220> FEATURE:
<223> OTHER INFORMATION: TRP1 peptide 41.0078

<400> SEQUENCE: 108

Leu Thr Trp His Arg Tyr His Leu Leu
1               5

<210> SEQ ID NO 109
<211> LENGTH: 9
<212> TYPE: PRT
<213> ORGANISM: Artificial Sequence
<220> FEATURE:
<223> OTHER INFORMATION: TRP1 peptide 41.0082

<400> SEQUENCE: 109

Met Leu Gln Glu Pro Ser Phe Ser Leu
1               5

<210> SEQ ID NO 110
<211> LENGTH: 9
<212> TYPE: PRT
<213> ORGANISM: Artificial Sequence
<220> FEATURE:
<223> OTHER INFORMATION: TRP1 peptide 41.0083

<400> SEQUENCE: 110

Ser Leu Pro Tyr Trp Asn Phe Ala Thr
1               5

<210> SEQ ID NO 111
<211> LENGTH: 9
<212> TYPE: PRT
<213> ORGANISM: Artificial Sequence
<220> FEATURE:
<223> OTHER INFORMATION: TRP1 peptide 41.0088

<400> SEQUENCE: 111

Arg Leu Pro Glu Pro Gln Asp Val Ala
1               5

<210> SEQ ID NO 112
<211> LENGTH: 9
<212> TYPE: PRT
<213> ORGANISM: Artificial Sequence
<220> FEATURE:
<223> OTHER INFORMATION: TRP1 peptide 41.0090

<400> SEQUENCE: 112

Val Thr Gln Cys Leu Glu Val Arg Val
1               5

<210> SEQ ID NO 113
<211> LENGTH: 9
<212> TYPE: PRT
<213> ORGANISM: Artificial Sequence
<220> FEATURE:
<223> OTHER INFORMATION: TRP1 peptide 41.0096

<400> SEQUENCE: 113

Leu Leu His Thr Phe Thr Asp Ala Val
1               5

<210> SEQ ID NO 114
<211> LENGTH: 9
<212> TYPE: PRT
<213> ORGANISM: Artificial Sequence
<220> FEATURE:
<223> OTHER INFORMATION: TRP1 peptide 41.0100

<400> SEQUENCE: 114

Asn Met Val Pro Phe Trp Pro Pro Val
 1               5

<210> SEQ ID NO 115
<211> LENGTH: 9
<212> TYPE: PRT
<213> ORGANISM: Artificial Sequence
<220> FEATURE:
<223> OTHER INFORMATION: TRP1 peptide 41.0104

<400> SEQUENCE: 115

Ala Val Val Gly Ala Leu Leu Leu Val
 1               5

<210> SEQ ID NO 116
<211> LENGTH: 9
<212> TYPE: PRT
<213> ORGANISM: Artificial Sequence
<220> FEATURE:
<223> OTHER INFORMATION: TRP1 peptide 41.0105

<400> SEQUENCE: 116

Ala Val Val Ala Ala Leu Leu Leu Val
 1               5

<210> SEQ ID NO 117
<211> LENGTH: 9
<212> TYPE: PRT
<213> ORGANISM: Artificial Sequence
<220> FEATURE:
<223> OTHER INFORMATION: TRP1 peptide 41.0108

<400> SEQUENCE: 117

Leu Leu Val Ala Ala Ile Phe Gly Val
 1               5

<210> SEQ ID NO 118
<211> LENGTH: 9
<212> TYPE: PRT
<213> ORGANISM: Artificial Sequence
<220> FEATURE:
<223> OTHER INFORMATION: TRP1 peptide 41.0112

<400> SEQUENCE: 118

Ser Met Asp Glu Ala Asn Gln Pro Leu
 1               5

<210> SEQ ID NO 119
<211> LENGTH: 9
<212> TYPE: PRT
<213> ORGANISM: Artificial Sequence
<220> FEATURE:
<223> OTHER INFORMATION: TRP1 peptide 41.0114

<400> SEQUENCE: 119

Val Leu Pro Leu Ala Tyr Ile Ser Val
 1               5

<210> SEQ ID NO 120

```
<211> LENGTH: 9
<212> TYPE: PRT
<213> ORGANISM: Artificial Sequence
<220> FEATURE:
<223> OTHER INFORMATION: TRP1 peptide 41.0115

<400> SEQUENCE: 120

Ser Leu Gly Cys Ile Phe Phe Pro Val
 1               5

<210> SEQ ID NO 121
<211> LENGTH: 9
<212> TYPE: PRT
<213> ORGANISM: Artificial Sequence
<220> FEATURE:
<223> OTHER INFORMATION: TRP1 peptide 41.0116

<400> SEQUENCE: 121

Pro Leu Ala Tyr Ile Ser Leu Phe Val
 1               5

<210> SEQ ID NO 122
<211> LENGTH: 9
<212> TYPE: PRT
<213> ORGANISM: Artificial Sequence
<220> FEATURE:
<223> OTHER INFORMATION: TRP1 peptide 41.0117

<400> SEQUENCE: 122

Leu Leu Leu Phe Gln Gln Ala Arg Val
 1               5

<210> SEQ ID NO 123
<211> LENGTH: 9
<212> TYPE: PRT
<213> ORGANISM: Artificial Sequence
<220> FEATURE:
<223> OTHER INFORMATION: TRP1 peptide 41.0118

<400> SEQUENCE: 123

Leu Met Leu Phe Tyr Gln Val Trp Val
 1               5

<210> SEQ ID NO 124
<211> LENGTH: 9
<212> TYPE: PRT
<213> ORGANISM: Artificial Sequence
<220> FEATURE:
<223> OTHER INFORMATION: TRP1 peptide 41.0119

<400> SEQUENCE: 124

Leu Leu Pro Ser Ser Gly Pro Gly Val
 1               5

<210> SEQ ID NO 125
<211> LENGTH: 9
<212> TYPE: PRT
<213> ORGANISM: Artificial Sequence
<220> FEATURE:
<223> OTHER INFORMATION: TRP1 peptide 41.0121

<400> SEQUENCE: 125

Asn Leu Ser Ile Tyr Asn Tyr Phe Val
 1               5

<210> SEQ ID NO 126
<211> LENGTH: 9
```

<212> TYPE: PRT
<213> ORGANISM: Artificial Sequence
<220> FEATURE:
<223> OTHER INFORMATION: TRP1 peptide 41.0122

<400> SEQUENCE: 126

Asn Leu Ser Val Tyr Asn Tyr Phe Val
 1               5

<210> SEQ ID NO 127
<211> LENGTH: 9
<212> TYPE: PRT
<213> ORGANISM: Artificial Sequence
<220> FEATURE:
<223> OTHER INFORMATION: TRP1 peptide 41.0123

<400> SEQUENCE: 127

Phe Leu Trp Thr His Tyr Tyr Ser Val
 1               5

<210> SEQ ID NO 128
<211> LENGTH: 9
<212> TYPE: PRT
<213> ORGANISM: Artificial Sequence
<220> FEATURE:
<223> OTHER INFORMATION: TRP1 peptide 41.0124

<400> SEQUENCE: 128

Ser Leu Lys Lys Thr Phe Leu Gly Val
 1               5

<210> SEQ ID NO 129
<211> LENGTH: 9
<212> TYPE: PRT
<213> ORGANISM: Artificial Sequence
<220> FEATURE:
<223> OTHER INFORMATION: TRP1 peptide 41.0125

<400> SEQUENCE: 129

Phe Leu Thr Trp His Arg Tyr His Val
 1               5

<210> SEQ ID NO 130
<211> LENGTH: 9
<212> TYPE: PRT
<213> ORGANISM: Artificial Sequence
<220> FEATURE:
<223> OTHER INFORMATION: TRP1 peptide 41.0129

<400> SEQUENCE: 130

Met Leu Gln Glu Pro Ser Phe Ser Val
 1               5

<210> SEQ ID NO 131
<211> LENGTH: 9
<212> TYPE: PRT
<213> ORGANISM: Artificial Sequence
<220> FEATURE:
<223> OTHER INFORMATION: TRP1 peptide 41.0130

<400> SEQUENCE: 131

Ser Leu Pro Tyr Trp Asn Phe Ala Val
 1               5

<210> SEQ ID NO 132
<211> LENGTH: 9
<212> TYPE: PRT

-continued

```
<213> ORGANISM: Artificial Sequence
<220> FEATURE:
<223> OTHER INFORMATION: TRP1 peptide 41.0131

<400> SEQUENCE: 132

Ala Leu Gly Lys Asn Val Cys Asp Val
 1               5

<210> SEQ ID NO 133
<211> LENGTH: 9
<212> TYPE: PRT
<213> ORGANISM: Artificial Sequence
<220> FEATURE:
<223> OTHER INFORMATION: TRP1 peptide 41.0132

<400> SEQUENCE: 133

Ser Leu Leu Ile Ser Pro Asn Ser Val
 1               5

<210> SEQ ID NO 134
<211> LENGTH: 9
<212> TYPE: PRT
<213> ORGANISM: Artificial Sequence
<220> FEATURE:
<223> OTHER INFORMATION: TRP1 peptide 41.0133

<400> SEQUENCE: 134

Ser Leu Phe Ser Gln Trp Arg Val Val
 1               5

<210> SEQ ID NO 135
<211> LENGTH: 9
<212> TYPE: PRT
<213> ORGANISM: Artificial Sequence
<220> FEATURE:
<223> OTHER INFORMATION: TRP1 peptide 41.0134

<400> SEQUENCE: 135

Thr Leu Gly Thr Leu Cys Asn Ser Val
 1               5

<210> SEQ ID NO 136
<211> LENGTH: 9
<212> TYPE: PRT
<213> ORGANISM: Artificial Sequence
<220> FEATURE:
<223> OTHER INFORMATION: TRP1 peptide 41.0136

<400> SEQUENCE: 136

Arg Leu Pro Glu Pro Gln Asp Val Val
 1               5

<210> SEQ ID NO 137
<211> LENGTH: 9
<212> TYPE: PRT
<213> ORGANISM: Artificial Sequence
<220> FEATURE:
<223> OTHER INFORMATION: TRP1 peptide 41.0137

<400> SEQUENCE: 137

Val Leu Gln Cys Leu Glu Val Arg Val
 1               5

<210> SEQ ID NO 138
<211> LENGTH: 9
<212> TYPE: PRT
<213> ORGANISM: Artificial Sequence
```

```
<220> FEATURE:
<223> OTHER INFORMATION: TRP1 peptide 41.0138

<400> SEQUENCE: 138

Ser Leu Asn Ser Phe Arg Asn Thr Val
 1               5

<210> SEQ ID NO 139
<211> LENGTH: 9
<212> TYPE: PRT
<213> ORGANISM: Artificial Sequence
<220> FEATURE:
<223> OTHER INFORMATION: TRP1 peptide 41.0139

<400> SEQUENCE: 139

Ser Leu Asp Ser Phe Arg Asn Thr Val
 1               5

<210> SEQ ID NO 140
<211> LENGTH: 9
<212> TYPE: PRT
<213> ORGANISM: Artificial Sequence
<220> FEATURE:
<223> OTHER INFORMATION: TRP1 peptide 41.0141

<400> SEQUENCE: 140

Phe Leu Asn Gly Thr Gly Gly Gln Val
 1               5

<210> SEQ ID NO 141
<211> LENGTH: 9
<212> TYPE: PRT
<213> ORGANISM: Artificial Sequence
<220> FEATURE:
<223> OTHER INFORMATION: TRP1 peptide 41.0142

<400> SEQUENCE: 141

Val Leu Leu His Thr Phe Thr Asp Val
 1               5

<210> SEQ ID NO 142
<211> LENGTH: 9
<212> TYPE: PRT
<213> ORGANISM: Artificial Sequence
<220> FEATURE:
<223> OTHER INFORMATION: TRP1 peptide 41.0145

<400> SEQUENCE: 142

Ala Leu Val Gly Ala Leu Leu Leu Val
 1               5

<210> SEQ ID NO 143
<211> LENGTH: 9
<212> TYPE: PRT
<213> ORGANISM: Artificial Sequence
<220> FEATURE:
<223> OTHER INFORMATION: TRP1 peptide 41.0146

<400> SEQUENCE: 143

Ala Leu Val Ala Ala Leu Leu Leu Val
 1               5

<210> SEQ ID NO 144
<211> LENGTH: 9
<212> TYPE: PRT
<213> ORGANISM: Artificial Sequence
<220> FEATURE:
```

<223> OTHER INFORMATION: TRP1 peptide 41.0147

<400> SEQUENCE: 144

Leu Leu Val Ala Leu Ile Phe Gly Val
 1               5

<210> SEQ ID NO 145
<211> LENGTH: 9
<212> TYPE: PRT
<213> ORGANISM: Artificial Sequence
<220> FEATURE:
<223> OTHER INFORMATION: TRP1 peptide 41.0148

<400> SEQUENCE: 145

Tyr Leu Ile Arg Ala Arg Arg Ser Val
 1               5

<210> SEQ ID NO 146
<211> LENGTH: 9
<212> TYPE: PRT
<213> ORGANISM: Artificial Sequence
<220> FEATURE:
<223> OTHER INFORMATION: TRP1 peptide 41.0149

<400> SEQUENCE: 146

Ser Met Asp Glu Ala Asn Gln Pro Val
 1               5

<210> SEQ ID NO 147
<211> LENGTH: 10
<212> TYPE: PRT
<213> ORGANISM: Artificial Sequence
<220> FEATURE:
<223> OTHER INFORMATION: TRP1 peptide 41.0151

<400> SEQUENCE: 147

Ser Leu Gly Cys Ile Phe Phe Pro Leu Leu
 1               5                  10

<210> SEQ ID NO 148
<211> LENGTH: 10
<212> TYPE: PRT
<213> ORGANISM: Artificial Sequence
<220> FEATURE:
<223> OTHER INFORMATION: TRP1 peptide 41.0157

<400> SEQUENCE: 148

Gly Met Cys Cys Pro Asp Leu Ser Pro Val
 1               5                  10

<210> SEQ ID NO 149
<211> LENGTH: 10
<212> TYPE: PRT
<213> ORGANISM: Artificial Sequence
<220> FEATURE:
<223> OTHER INFORMATION: TRP1 peptide 41.0160

<400> SEQUENCE: 149

Ala Ala Cys Asn Gln Lys Ile Leu Thr Val
 1               5                  10

<210> SEQ ID NO 150
<211> LENGTH: 10
<212> TYPE: PRT
<213> ORGANISM: Artificial Sequence
<220> FEATURE:
<223> OTHER INFORMATION: TRP1 peptide 41.0162

<400> SEQUENCE: 150

Phe Leu Thr Trp His Arg Tyr His Leu Leu
1               5                   10

<210> SEQ ID NO 151
<211> LENGTH: 10
<212> TYPE: PRT
<213> ORGANISM: Artificial Sequence
<220> FEATURE:
<223> OTHER INFORMATION: TRP1 peptide 41.0166

<400> SEQUENCE: 151

Ser Leu His Asn Leu Ala His Leu Phe Leu
1               5                   10

<210> SEQ ID NO 152
<211> LENGTH: 10
<212> TYPE: PRT
<213> ORGANISM: Artificial Sequence
<220> FEATURE:
<223> OTHER INFORMATION: TRP1 peptide 41.0174

<400> SEQUENCE: 152

Leu Leu Leu Val Ala Ala Ile Phe Gly Val
1               5                   10

<210> SEQ ID NO 153
<211> LENGTH: 10
<212> TYPE: PRT
<213> ORGANISM: Artificial Sequence
<220> FEATURE:
<223> OTHER INFORMATION: TRP1 peptide 41.0177

<400> SEQUENCE: 153

Leu Leu Val Ala Ala Ile Phe Gly Val Ala
1               5                   10

<210> SEQ ID NO 154
<211> LENGTH: 10
<212> TYPE: PRT
<213> ORGANISM: Artificial Sequence
<220> FEATURE:
<223> OTHER INFORMATION: TRP1 peptide 41.0178

<400> SEQUENCE: 154

Ala Leu Ile Phe Gly Thr Ala Ser Tyr Leu
1               5                   10

<210> SEQ ID NO 155
<211> LENGTH: 10
<212> TYPE: PRT
<213> ORGANISM: Artificial Sequence
<220> FEATURE:
<223> OTHER INFORMATION: TRP1 peptide 41.0180

<400> SEQUENCE: 155

Ser Met Asp Glu Ala Asn Gln Pro Leu Leu
1               5                   10

<210> SEQ ID NO 156
<211> LENGTH: 10
<212> TYPE: PRT
<213> ORGANISM: Artificial Sequence
<220> FEATURE:
<223> OTHER INFORMATION: TRP1 peptide 41.0181

```
<400> SEQUENCE: 156

Leu Leu Thr Asp Gln Tyr Gln Cys Tyr Ala
1               5                   10

<210> SEQ ID NO 157
<211> LENGTH: 10
<212> TYPE: PRT
<213> ORGANISM: Artificial Sequence
<220> FEATURE:
<223> OTHER INFORMATION: TRP1 peptide 41.0183

<400> SEQUENCE: 157

Ser Leu Gly Cys Ile Phe Phe Pro Leu Val
1               5                   10

<210> SEQ ID NO 158
<211> LENGTH: 10
<212> TYPE: PRT
<213> ORGANISM: Artificial Sequence
<220> FEATURE:
<223> OTHER INFORMATION: TRP1 peptide 41.0186

<400> SEQUENCE: 158

Phe Leu Met Leu Phe Tyr Gln Val Trp Val
1               5                   10

<210> SEQ ID NO 159
<211> LENGTH: 10
<212> TYPE: PRT
<213> ORGANISM: Artificial Sequence
<220> FEATURE:
<223> OTHER INFORMATION: TRP1 peptide 41.0189

<400> SEQUENCE: 159

Ala Leu Cys Asp Gln Arg Val Leu Ile Val
1               5                   10

<210> SEQ ID NO 160
<211> LENGTH: 10
<212> TYPE: PRT
<213> ORGANISM: Artificial Sequence
<220> FEATURE:
<223> OTHER INFORMATION: TRP1 peptide 41.0190

<400> SEQUENCE: 160

Ala Leu Cys Asn Gln Lys Ile Leu Thr Val
1               5                   10

<210> SEQ ID NO 161
<211> LENGTH: 10
<212> TYPE: PRT
<213> ORGANISM: Artificial Sequence
<220> FEATURE:
<223> OTHER INFORMATION: TRP1 peptide 41.0191

<400> SEQUENCE: 161

Phe Leu Thr Trp His Arg Tyr His Leu Val
1               5                   10

<210> SEQ ID NO 162
<211> LENGTH: 10
<212> TYPE: PRT
<213> ORGANISM: Artificial Sequence
<220> FEATURE:
<223> OTHER INFORMATION: TRP1 peptide 41.0197

<400> SEQUENCE: 162
```

Ser Leu His Asn Leu Ala His Leu Phe Val
1               5                   10

<210> SEQ ID NO 163
<211> LENGTH: 10
<212> TYPE: PRT
<213> ORGANISM: Artificial Sequence
<220> FEATURE:
<223> OTHER INFORMATION: TRP1 peptide 41.0198

<400> SEQUENCE: 163

Asn Leu Ala His Leu Phe Leu Asn Gly Val
1               5                   10

<210> SEQ ID NO 164
<211> LENGTH: 10
<212> TYPE: PRT
<213> ORGANISM: Artificial Sequence
<220> FEATURE:
<223> OTHER INFORMATION: TRP1 peptide 41.0199

<400> SEQUENCE: 164

Asn Met Val Pro Phe Trp Pro Pro Val Val
1               5                   10

<210> SEQ ID NO 165
<211> LENGTH: 10
<212> TYPE: PRT
<213> ORGANISM: Artificial Sequence
<220> FEATURE:
<223> OTHER INFORMATION: TRP1 peptide 41.0201

<400> SEQUENCE: 165

Ile Leu Val Val Ala Ala Leu Leu Leu Val
1               5                   10

<210> SEQ ID NO 166
<211> LENGTH: 10
<212> TYPE: PRT
<213> ORGANISM: Artificial Sequence
<220> FEATURE:
<223> OTHER INFORMATION: TRP1 peptide 41.0203

<400> SEQUENCE: 166

Leu Leu Val Ala Leu Ile Phe Gly Thr Val
1               5                   10

<210> SEQ ID NO 167
<211> LENGTH: 10
<212> TYPE: PRT
<213> ORGANISM: Artificial Sequence
<220> FEATURE:
<223> OTHER INFORMATION: TRP1 peptide 41.0205

<400> SEQUENCE: 167

Ala Leu Ile Phe Gly Thr Ala Ser Tyr Val
1               5                   10

<210> SEQ ID NO 168
<211> LENGTH: 10
<212> TYPE: PRT
<213> ORGANISM: Artificial Sequence
<220> FEATURE:
<223> OTHER INFORMATION: TRP1 peptide 41.0206

<400> SEQUENCE: 168

Ser Met Asp Glu Ala Asn Gln Pro Leu Val
1               5                   10

<210> SEQ ID NO 169
<211> LENGTH: 10
<212> TYPE: PRT
<213> ORGANISM: Artificial Sequence
<220> FEATURE:
<223> OTHER INFORMATION: TRP1 peptide 41.0207

<400> SEQUENCE: 169

Leu Leu Thr Asp Gln Tyr Gln Cys Tyr Val
1               5                   10

<210> SEQ ID NO 170
<211> LENGTH: 11
<212> TYPE: PRT
<213> ORGANISM: Artificial Sequence
<220> FEATURE:
<223> OTHER INFORMATION: CEA.107 peptide 41.0212

<400> SEQUENCE: 170

Leu Leu Ile Gln Asn Ile Ile Gln Asn Asp Thr
1               5                   10

<210> SEQ ID NO 171
<211> LENGTH: 11
<212> TYPE: PRT
<213> ORGANISM: Artificial Sequence
<220> FEATURE:
<223> OTHER INFORMATION: CEA.112 peptide 41.0214

<400> SEQUENCE: 171

Ile Ile Gln Asn Asp Thr Gly Phe Tyr Thr Leu
1               5                   10

<210> SEQ ID NO 172
<211> LENGTH: 11
<212> TYPE: PRT
<213> ORGANISM: Artificial Sequence
<220> FEATURE:
<223> OTHER INFORMATION: CEA.201 peptide 41.0221

<400> SEQUENCE: 172

Thr Leu Phe Asn Val Thr Arg Asn Asp Thr Ala
1               5                   10

<210> SEQ ID NO 173
<211> LENGTH: 11
<212> TYPE: PRT
<213> ORGANISM: Artificial Sequence
<220> FEATURE:
<223> OTHER INFORMATION: CEA.378 peptide 41.0235

<400> SEQUENCE: 173

Leu Thr Leu Leu Ser Val Thr Arg Asn Asp Val
1               5                   10

<210> SEQ ID NO 174
<211> LENGTH: 11
<212> TYPE: PRT
<213> ORGANISM: Artificial Sequence
<220> FEATURE:
<223> OTHER INFORMATION: CEA.473 peptide 41.0243

<400> SEQUENCE: 174

Gly Leu Tyr Thr Cys Gln Ala Asn Asn Ser Ala

-continued

```
1               5                  10
```

<210> SEQ ID NO 175
<211> LENGTH: 11
<212> TYPE: PRT
<213> ORGANISM: Artificial Sequence
<220> FEATURE:
<223> OTHER INFORMATION: CEA.687 peptide 41.0268

<400> SEQUENCE: 175

```
Ala Thr Val Gly Ile Met Ile Gly Val Leu Val
1               5                  10
```

<210> SEQ ID NO 176
<211> LENGTH: 11
<212> TYPE: PRT
<213> ORGANISM: Artificial Sequence
<220> FEATURE:
<223> OTHER INFORMATION: mp53.184.V3 peptide 44.0075

<400> SEQUENCE: 176

```
Gly Leu Val Pro Pro Gln His Leu Ile Arg Val
1               5                  10
```

<210> SEQ ID NO 177
<211> LENGTH: 11
<212> TYPE: PRT
<213> ORGANISM: Artificial Sequence
<220> FEATURE:
<223> OTHER INFORMATION: mp53.184.V6 peptide 44.0087

<400> SEQUENCE: 177

```
Gly Leu Ala Pro Pro Val His Leu Ile Arg Val
1               5                  10
```

<210> SEQ ID NO 178
<211> LENGTH: 11
<212> TYPE: PRT
<213> ORGANISM: Artificial Sequence
<220> FEATURE:
<223> OTHER INFORMATION: mp53.184.E6 peptide 44.0092

<400> SEQUENCE: 178

```
Gly Leu Ala Pro Pro Glu His Leu Ile Arg Val
1               5                  10
```

<210> SEQ ID NO 179
<211> LENGTH: 9
<212> TYPE: PRT
<213> ORGANISM: Artificial Sequence
<220> FEATURE:
<223> OTHER INFORMATION: CEA.691.L2 peptide 1227.10

<400> SEQUENCE: 179

```
Ile Leu Ile Gly Val Leu Val Gly Val
1               5
```

<210> SEQ ID NO 180
<211> LENGTH: 10
<212> TYPE: PRT
<213> ORGANISM: Artificial Sequence
<220> FEATURE:
<223> OTHER INFORMATION: Her2/neu.952.L2V10 peptide 1234.26

<400> SEQUENCE: 180

```
Tyr Leu Ile Met Val Lys Cys Trp Met Val
1               5                  10
```

```
<210> SEQ ID NO 181
<211> LENGTH: 9
<212> TYPE: PRT
<213> ORGANISM: Artificial Sequence
<220> FEATURE:
<223> OTHER INFORMATION: mp53.261 peptide 1295.06

<400> SEQUENCE: 181

Leu Leu Gly Arg Asp Ser Phe Glu Val
 1               5

<210> SEQ ID NO 182
<211> LENGTH: 9
<212> TYPE: PRT
<213> ORGANISM: Artificial Sequence
<220> FEATURE:
<223> OTHER INFORMATION: FLu.RRP2.446 peptide 1319.01

<400> SEQUENCE: 182

Phe Met Tyr Ser Asp Phe His Phe Ile
 1               5

<210> SEQ ID NO 183
<211> LENGTH: 9
<212> TYPE: PRT
<213> ORGANISM: Artificial Sequence
<220> FEATURE:
<223> OTHER INFORMATION: Flu.RRP2.446 peptide 1319.06

<400> SEQUENCE: 183

Asn Met Leu Ser Thr Val Leu Gly Val
 1               5

<210> SEQ ID NO 184
<211> LENGTH: 9
<212> TYPE: PRT
<213> ORGANISM: Artificial Sequence
<220> FEATURE:
<223> OTHER INFORMATION: Flu.RRP2.446 peptide 1319.14

<400> SEQUENCE: 184

Ser Leu Glu Asn Phe Arg Ala Tyr Val
 1               5

<210> SEQ ID NO 185
<211> LENGTH: 9
<212> TYPE: PRT
<213> ORGANISM: Artificial Sequence
<220> FEATURE:
<223> OTHER INFORMATION: Mage3.112 peptide 1325.06

<400> SEQUENCE: 185

Lys Met Ala Glu Leu Val His Phe Val
 1               5

<210> SEQ ID NO 186
<211> LENGTH: 9
<212> TYPE: PRT
<213> ORGANISM: Artificial Sequence
<220> FEATURE:
<223> OTHER INFORMATION: Mage3.112 peptide 1325.07

<400> SEQUENCE: 186

Lys Leu Ala Glu Leu Val His Phe Val
 1               5
```

<210> SEQ ID NO 187
<211> LENGTH: 9
<212> TYPE: PRT
<213> ORGANISM: Artificial Sequence
<220> FEATURE:
<223> OTHER INFORMATION: Her2/neu.153.V9 peptide 1334.01

<400> SEQUENCE: 187

Val Leu Ile Gln Arg Asn Pro Gln Val
1               5

<210> SEQ ID NO 188
<211> LENGTH: 9
<212> TYPE: PRT
<213> ORGANISM: Artificial Sequence
<220> FEATURE:
<223> OTHER INFORMATION: Her2/neu.665.L2V9 peptide 1334.02

<400> SEQUENCE: 188

Val Leu Leu Gly Val Val Phe Gly Val
1               5

<210> SEQ ID NO 189
<211> LENGTH: 9
<212> TYPE: PRT
<213> ORGANISM: Artificial Sequence
<220> FEATURE:
<223> OTHER INFORMATION: Her2/neu.653.L2V9 peptide 1334.03

<400> SEQUENCE: 189

Ser Leu Ile Ser Ala Val Val Gly Val
1               5

<210> SEQ ID NO 190
<211> LENGTH: 10
<212> TYPE: PRT
<213> ORGANISM: Artificial Sequence
<220> FEATURE:
<223> OTHER INFORMATION: Her2/neu.952.B7 peptide 1334.04

<400> SEQUENCE: 190

Tyr Met Ile Met Val Lys Asx Trp Met Ile
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Her2/neu.952.L2B7V10 peptide 1334.05

<400> SEQUENCE: 191

Tyr Leu Ile Met Val Lys Asx Trp Met Val
1               5                   10

<210> SEQ ID NO 192
<211> LENGTH: 9
<212> TYPE: PRT
<213> ORGANISM: Artificial Sequence
<220> FEATURE:
<223> OTHER INFORMATION: Mage3.220.L2V9 peptide 1334.06

<400> SEQUENCE: 192

Lys Leu Trp Glu Glu Leu Ser Val Val
1               5

```
<210> SEQ ID NO 193
<211> LENGTH: 9
<212> TYPE: PRT
<213> ORGANISM: Artificial Sequence
<220> FEATURE:
<223> OTHER INFORMATION: Her2/neu.5.M2B3V9 peptide 1334.08

<400> SEQUENCE: 193

Ala Met Asx Arg Trp Gly Leu Leu Val
 1               5

<210> SEQ ID NO 194
<211> LENGTH: 9
<212> TYPE: PRT
<213> ORGANISM: Artificial Sequence
<220> FEATURE:
<223> OTHER INFORMATION: CEA.691.J2 peptide 1345.01
<220> FEATURE:
<221> NAME/KEY: MOD_RES
<222> LOCATION: (2)...(2)
<223> OTHER INFORMATION: Nle

<400> SEQUENCE: 194

Ile Xaa Ile Gly Val Leu Val Gly Val
 1               5

<210> SEQ ID NO 195
<211> LENGTH: 9
<212> TYPE: PRT
<213> ORGANISM: Artificial Sequence
<220> FEATURE:
<223> OTHER INFORMATION: CEA.687.J6 peptide 1345.02
<220> FEATURE:
<221> NAME/KEY: MOD_RES
<222> LOCATION: (6)...(6)
<223> OTHER INFORMATION: Nle

<400> SEQUENCE: 195

Ala Thr Val Gly Ile Xaa Ile Gly Val
 1               5

<210> SEQ ID NO 196
<211> LENGTH: 9
<212> TYPE: PRT
<213> ORGANISM: Artificial Sequence
<220> FEATURE:
<223> OTHER INFORMATION: p53.149.J2 peptide 1345.03
<220> FEATURE:
<221> NAME/KEY: MOD_RES
<222> LOCATION: (2)...(2)
<223> OTHER INFORMATION: Nle

<400> SEQUENCE: 196

Ser Xaa Pro Pro Pro Gly Thr Arg Val
 1               5

<210> SEQ ID NO 197
<211> LENGTH: 10
<212> TYPE: PRT
<213> ORGANISM: Artificial Sequence
<220> FEATURE:
<223> OTHER INFORMATION: MAGE3.160.J8 peptide 1345.04
<220> FEATURE:
<221> NAME/KEY: MOD_RES
<222> LOCATION: (8)...(8)
<223> OTHER INFORMATION: Nle

<400> SEQUENCE: 197

Leu Val Phe Gly Ile Glu Leu Xaa Glu Val
 1               5                  10
```

```
<210> SEQ ID NO 198
<211> LENGTH: 8
<212> TYPE: PRT
<213> ORGANISM: Artificial Sequence
<220> FEATURE:
<223> OTHER INFORMATION: Flu.M1.59 peptide 918.12

<400> SEQUENCE: 198

Ile Leu Gly Phe Val Phe Thr Leu
1               5

<210> SEQ ID NO 199
<211> LENGTH: 9
<212> TYPE: PRT
<213> ORGANISM: Artificial Sequence
<220> FEATURE:
<223> OTHER INFORMATION: Her2/neu peptide 1095.22

<400> SEQUENCE: 199

Lys Ile Phe Gly Ser Leu Ala Phe Leu
1               5

<210> SEQ ID NO 200
<211> LENGTH: 10
<212> TYPE: PRT
<213> ORGANISM: Artificial Sequence
<220> FEATURE:
<223> OTHER INFORMATION: MAGE2 peptide 1090.01

<400> SEQUENCE: 200

Tyr Leu Gln Leu Val Phe Gly Ile Glu Val
1               5                   10

<210> SEQ ID NO 201
<211> LENGTH: 9
<212> TYPE: PRT
<213> ORGANISM: Artificial Sequence
<220> FEATURE:
<223> OTHER INFORMATION: PSM peptide 1126.01

<400> SEQUENCE: 201

Met Met Asn Asp Gln Leu Met Phe Leu
1               5

<210> SEQ ID NO 202
<211> LENGTH: 10
<212> TYPE: PRT
<213> ORGANISM: Artificial Sequence
<220> FEATURE:
<223> OTHER INFORMATION: PSM peptide 1126.02

<400> SEQUENCE: 202

Ala Leu Val Leu Ala Gly Gly Phe Phe Leu
1               5                   10

<210> SEQ ID NO 203
<211> LENGTH: 9
<212> TYPE: PRT
<213> ORGANISM: Artificial Sequence
<220> FEATURE:
<223> OTHER INFORMATION: PSM peptide 1126.03

<400> SEQUENCE: 203

Trp Leu Cys Ala Gly Ala Leu Val Leu
1               5
```

<210> SEQ ID NO 204
<211> LENGTH: 9
<212> TYPE: PRT
<213> ORGANISM: Artificial Sequence
<220> FEATURE:
<223> OTHER INFORMATION: PSM peptide 1126.05

<400> SEQUENCE: 204

Met Val Phe Glu Leu Ala Asn Ser Ile
 1               5

<210> SEQ ID NO 205
<211> LENGTH: 10
<212> TYPE: PRT
<213> ORGANISM: Artificial Sequence
<220> FEATURE:
<223> OTHER INFORMATION: PSM peptide 1126.06

<400> SEQUENCE: 205

Arg Met Met Asn Asp Gln Leu Met Phe Leu
 1               5                  10

<210> SEQ ID NO 206
<211> LENGTH: 9
<212> TYPE: PRT
<213> ORGANISM: Artificial Sequence
<220> FEATURE:
<223> OTHER INFORMATION: PSM peptide 1126.09

<400> SEQUENCE: 206

Leu Val Leu Ala Gly Gly Phe Phe Leu
 1               5

<210> SEQ ID NO 207
<211> LENGTH: 9
<212> TYPE: PRT
<213> ORGANISM: Artificial Sequence
<220> FEATURE:
<223> OTHER INFORMATION: PSM peptide 1126.10

<400> SEQUENCE: 207

Val Leu Ala Gly Gly Phe Phe Leu Leu
 1               5

<210> SEQ ID NO 208
<211> LENGTH: 9
<212> TYPE: PRT
<213> ORGANISM: Artificial Sequence
<220> FEATURE:
<223> OTHER INFORMATION: PSM peptide 1126.12

<400> SEQUENCE: 208

Leu Leu His Glu Thr Asp Ser Ala Val
 1               5

<210> SEQ ID NO 209
<211> LENGTH: 9
<212> TYPE: PRT
<213> ORGANISM: Artificial Sequence
<220> FEATURE:
<223> OTHER INFORMATION: PSM peptide 1126.14

<400> SEQUENCE: 209

Leu Met Tyr Ser Leu Val His Asn Leu
 1               5

```
<210> SEQ ID NO 210
<211> LENGTH: 10
<212> TYPE: PRT
<213> ORGANISM: Artificial Sequence
<220> FEATURE:
<223> OTHER INFORMATION: PSM peptide 1126.16

<400> SEQUENCE: 210

Gln Leu Met Phe Leu Glu Arg Ala Phe Ile
 1               5                  10

<210> SEQ ID NO 211
<211> LENGTH: 9
<212> TYPE: PRT
<213> ORGANISM: Artificial Sequence
<220> FEATURE:
<223> OTHER INFORMATION: PSM peptide 1126.17

<400> SEQUENCE: 211

Leu Met Phe Leu Glu Arg Ala Phe Ile
 1               5

<210> SEQ ID NO 212
<211> LENGTH: 10
<212> TYPE: PRT
<213> ORGANISM: Artificial Sequence
<220> FEATURE:
<223> OTHER INFORMATION: PSM peptide 1126.20

<400> SEQUENCE: 212

Lys Leu Gly Ser Gly Asn Asp Phe Glu Val
 1               5                  10

<210> SEQ ID NO 213
<211> LENGTH: 10
<212> TYPE: PRT
<213> ORGANISM: Artificial Sequence
<220> FEATURE:
<223> OTHER INFORMATION: PSM peptide 1129.01

<400> SEQUENCE: 213

Leu Leu Gln Glu Arg Gly Val Ala Tyr Ile
 1               5                  10

<210> SEQ ID NO 214
<211> LENGTH: 10
<212> TYPE: PRT
<213> ORGANISM: Artificial Sequence
<220> FEATURE:
<223> OTHER INFORMATION: PSM peptide 1129.04

<400> SEQUENCE: 214

Gly Met Pro Glu Gly Asp Leu Val Tyr Val
 1               5                  10

<210> SEQ ID NO 215
<211> LENGTH: 10
<212> TYPE: PRT
<213> ORGANISM: Artificial Sequence
<220> FEATURE:
<223> OTHER INFORMATION: PSM peptide 1129.05

<400> SEQUENCE: 215

Phe Leu Asp Glu Leu Lys Ala Glu Asn Ile
 1               5                  10

<210> SEQ ID NO 216
```

```
<211> LENGTH: 9
<212> TYPE: PRT
<213> ORGANISM: Artificial Sequence
<220> FEATURE:
<223> OTHER INFORMATION: PSM peptide 1129.08

<400> SEQUENCE: 216

Ala Leu Phe Asp Ile Glu Ser Lys Val
 1               5

<210> SEQ ID NO 217
<211> LENGTH: 10
<212> TYPE: PRT
<213> ORGANISM: Artificial Sequence
<220> FEATURE:
<223> OTHER INFORMATION: PSM peptide 1129.10

<400> SEQUENCE: 217

Gly Leu Pro Ser Ile Pro Val His Pro Ile
 1               5                  10

<210> SEQ ID NO 218
<211> LENGTH: 10
<212> TYPE: PRT
<213> ORGANISM: Artificial Sequence
<220> FEATURE:
<223> OTHER INFORMATION: HLA-A1 allele-specific motif
<220> FEATURE:
<221> NAME/KEY: VARIANT
<222> LOCATION: (1)...(10)
<223> OTHER INFORMATION: Xaa at location 1 is any amino acid;
      Xaa at location 2 is S or T;
      Xaa at location 3 is D or E;
      Xaa at location 5 is any amino acid;
<220> FEATURE:
<223> OTHER INFORMATION: Xaa at location 6 is any amino acid;
      Xaa at location 8 is any amino acid

<400> SEQUENCE: 218

Xaa Xaa Xaa Pro Xaa Xaa Leu Xaa Tyr Lys
 1               5                  10

<210> SEQ ID NO 219
<211> LENGTH: 10
<212> TYPE: PRT
<213> ORGANISM: Artificial Sequence
<220> FEATURE:
<223> OTHER INFORMATION: HDV.nuc.16 peptide 28.0719

<400> SEQUENCE: 219

Ile Leu Glu Gln Trp Val Ala Gly Arg Lys
 1               5                  10

<210> SEQ ID NO 220
<211> LENGTH: 10
<212> TYPE: PRT
<213> ORGANISM: Artificial Sequence
<220> FEATURE:
<223> OTHER INFORMATION: HDV.nuc.115 peptide 28.0727

<400> SEQUENCE: 220

Leu Ser Ala Gly Gly Lys Asn Leu Ser Lys
 1               5                  10

<210> SEQ ID NO 221
<211> LENGTH: 11
<212> TYPE: PRT
<213> ORGANISM: Artificial Sequence
<220> FEATURE:
```

-continued

<223> OTHER INFORMATION: Flu.HA.29 peptide 1259.02

<400> SEQUENCE: 221

Ser Thr Asp Thr Val Asp Thr Val Leu Glu Lys
1               5                   10

<210> SEQ ID NO 222
<211> LENGTH: 9
<212> TYPE: PRT
<213> ORGANISM: Artificial Sequence
<220> FEATURE:
<223> OTHER INFORMATION: Flu.HA.63 peptide 1259.04

<400> SEQUENCE: 222

Gly Ile Ala Pro Leu Gln Leu Gly Lys
1               5

<210> SEQ ID NO 223
<211> LENGTH: 10
<212> TYPE: PRT
<213> ORGANISM: Artificial Sequence
<220> FEATURE:
<223> OTHER INFORMATION: Flu.HA.149 peptide 1259.06

<400> SEQUENCE: 223

Val Thr Ala Ala Cys Ser His Ala Gly Lys
1               5                   10

<210> SEQ ID NO 224
<211> LENGTH: 9
<212> TYPE: PRT
<213> ORGANISM: Artificial Sequence
<220> FEATURE:
<223> OTHER INFORMATION: FLu.HA.195 peptide 1259.08

<400> SEQUENCE: 224

Gly Ile His His Pro Ser Asn Ser Lys
1               5

<210> SEQ ID NO 225
<211> LENGTH: 10
<212> TYPE: PRT
<213> ORGANISM: Artificial Sequence
<220> FEATURE:
<223> OTHER INFORMATION: Flu.HA.243 peptide 1259.10

<400> SEQUENCE: 225

Arg Met Asn Tyr Tyr Trp Thr Leu Leu Lys
1               5                   10

<210> SEQ ID NO 226
<211> LENGTH: 11
<212> TYPE: PRT
<213> ORGANISM: Artificial Sequence
<220> FEATURE:
<223> OTHER INFORMATION: Flu.HA.392 peptide 1259.12

<400> SEQUENCE: 226

Ile Thr Asn Lys Val Asn Ser Val Ile Glu Lys
1               5                   10

<210> SEQ ID NO 227
<211> LENGTH: 11
<212> TYPE: PRT
<213> ORGANISM: Artificial Sequence
<220> FEATURE:
<223> OTHER INFORMATION: Flu.HA.402 peptide 1259.13

```
<400> SEQUENCE: 227

Lys Met Asn Ile Gln Phe Thr Ala Val Gly Lys
 1               5                  10

<210> SEQ ID NO 228
<211> LENGTH: 9
<212> TYPE: PRT
<213> ORGANISM: Artificial Sequence
<220> FEATURE:
<223> OTHER INFORMATION: Flu.HA.404 peptide 1259.14

<400> SEQUENCE: 228

Asn Ile Gln Phe Thr Ala Val Gly Lys
 1               5

<210> SEQ ID NO 229
<211> LENGTH: 11
<212> TYPE: PRT
<213> ORGANISM: Artificial Sequence
<220> FEATURE:
<223> OTHER INFORMATION: Flu.HA.409 peptide 1259.16

<400> SEQUENCE: 229

Ala Val Gly Lys Glu Phe Asn Lys Leu Glu Lys
 1               5                  10

<210> SEQ ID NO 230
<211> LENGTH: 11
<212> TYPE: PRT
<213> ORGANISM: Artificial Sequence
<220> FEATURE:
<223> OTHER INFORMATION: Flu.HA.465 peptide 1259.19

<400> SEQUENCE: 230

Lys Val Lys Ser Gln Leu Lys Asn Asn Ala Lys
 1               5                  10

<210> SEQ ID NO 231
<211> LENGTH: 11
<212> TYPE: PRT
<213> ORGANISM: Artificial Sequence
<220> FEATURE:
<223> OTHER INFORMATION: Flu.HA.495 peptide 1259.20

<400> SEQUENCE: 231

Ser Val Arg Asn Gly Thr Tyr Asp Tyr Pro Lys
 1               5                  10

<210> SEQ ID NO 232
<211> LENGTH: 9
<212> TYPE: PRT
<213> ORGANISM: Artificial Sequence
<220> FEATURE:
<223> OTHER INFORMATION: Flu.VMT1.13 peptide 1259.21

<400> SEQUENCE: 232

Ser Ile Ile Pro Ser Gly Pro Leu Lys
 1               5

<210> SEQ ID NO 233
<211> LENGTH: 10
<212> TYPE: PRT
<213> ORGANISM: Artificial Sequence
<220> FEATURE:
<223> OTHER INFORMATION: Flu.VMT1.178 peptide 1259.25
```

```
<400> SEQUENCE: 233

Arg Met Val Leu Ala Ser Thr Thr Ala Lys
 1               5                  10

<210> SEQ ID NO 234
<211> LENGTH: 9
<212> TYPE: PRT
<213> ORGANISM: Artificial Sequence
<220> FEATURE:
<223> OTHER INFORMATION: Flu.VMT1.179 peptide 1259.26

<400> SEQUENCE: 234

Met Val Leu Ala Ser Thr Thr Ala Lys
 1               5

<210> SEQ ID NO 235
<211> LENGTH: 10
<212> TYPE: PRT
<213> ORGANISM: Artificial Sequence
<220> FEATURE:
<223> OTHER INFORMATION: Flu.VMT1.243 peptide 1259.28

<400> SEQUENCE: 235

Arg Met Gly Val Gln Met Gln Arg Phe Lys
 1               5                  10

<210> SEQ ID NO 236
<211> LENGTH: 10
<212> TYPE: PRT
<213> ORGANISM: Artificial Sequence
<220> FEATURE:
<223> OTHER INFORMATION: Flu.VNUC.22 peptide 1259.33

<400> SEQUENCE: 236

Ala Thr Glu Ile Arg Ala Ser Val Gly Lys
 1               5                  10

<210> SEQ ID NO 237
<211> LENGTH: 11
<212> TYPE: PRT
<213> ORGANISM: Artificial Sequence
<220> FEATURE:
<223> OTHER INFORMATION: Flu.VNUC.188 peptide 1259.37

<400> SEQUENCE: 237

Thr Met Val Met Glu Leu Val Arg Met Ile Lys
 1               5                  10

<210> SEQ ID NO 238
<211> LENGTH: 10
<212> TYPE: PRT
<213> ORGANISM: Artificial Sequence
<220> FEATURE:
<223> OTHER INFORMATION: Flu.VNUC.342 peptide 1259.43

<400> SEQUENCE: 238

Arg Val Leu Ser Phe Ile Lys Gly Thr Lys
 1               5                  10

<210> SEQ ID NO 239
<211> LENGTH: 9
<212> TYPE: PRT
<213> ORGANISM: Artificial Sequence
<220> FEATURE:
<223> OTHER INFORMATION: ORF3P peptide F119.01

<400> SEQUENCE: 239
```

```
Met Ser Leu Gln Arg Gln Phe Leu Arg
  1               5

<210> SEQ ID NO 240
<211> LENGTH: 9
<212> TYPE: PRT
<213> ORGANISM: Artificial Sequence
<220> FEATURE:
<223> OTHER INFORMATION: TRP.197 peptide F119.02

<400> SEQUENCE: 240

Leu Leu Gly Pro Gly Arg Pro Tyr Arg
  1               5

<210> SEQ ID NO 241
<211> LENGTH: 9
<212> TYPE: PRT
<213> ORGANISM: Artificial Sequence
<220> FEATURE:
<223> OTHER INFORMATION: TRP.197K9 peptide F119.03

<400> SEQUENCE: 241

Leu Leu Gly Pro Gly Arg Pro Tyr Lys
  1               5

<210> SEQ ID NO 242
<211> LENGTH: 8
<212> TYPE: PRT
<213> ORGANISM: Artificial Sequence
<220> FEATURE:
<223> OTHER INFORMATION: CEA.139 peptide 34.0019

<400> SEQUENCE: 242

Arg Val Tyr Pro Glu Leu Pro Lys
  1               5

<210> SEQ ID NO 243
<211> LENGTH: 8
<212> TYPE: PRT
<213> ORGANISM: Artificial Sequence
<220> FEATURE:
<223> OTHER INFORMATION: CEA.495 peptide 34.0020

<400> SEQUENCE: 243

Thr Val Ser Ala Glu Leu Pro Lys
  1               5

<210> SEQ ID NO 244
<211> LENGTH: 8
<212> TYPE: PRT
<213> ORGANISM: Artificial Sequence
<220> FEATURE:
<223> OTHER INFORMATION: CEA.317 peptide 34.0021

<400> SEQUENCE: 244

Thr Val Tyr Ala Glu Pro Pro Lys
  1               5

<210> SEQ ID NO 245
<211> LENGTH: 8
<212> TYPE: PRT
<213> ORGANISM: Artificial Sequence
<220> FEATURE:
<223> OTHER INFORMATION: MAGE2.74 peptide 34.0029

<400> SEQUENCE: 245
```

```
Thr Ile Asn Tyr Thr Leu Trp Arg
1               5
```

<210> SEQ ID NO 246
<211> LENGTH: 8
<212> TYPE: PRT
<213> ORGANISM: Artificial Sequence
<220> FEATURE:
<223> OTHER INFORMATION: MAGE2.116 peptide 34.0030

<400> SEQUENCE: 246

```
Leu Val His Phe Leu Leu Leu Lys
1               5
```

<210> SEQ ID NO 247
<211> LENGTH: 8
<212> TYPE: PRT
<213> ORGANISM: Artificial Sequence
<220> FEATURE:
<223> OTHER INFORMATION: MAGE2.237 peptide 34.0031

<400> SEQUENCE: 247

```
Ser Val Phe Ala His Pro Arg Lys
1               5
```

<210> SEQ ID NO 248
<211> LENGTH: 8
<212> TYPE: PRT
<213> ORGANISM: Artificial Sequence
<220> FEATURE:
<223> OTHER INFORMATION: MAGE3.285 peptide 34.0043

<400> SEQUENCE: 248

```
Lys Val Leu His His Met Val Lys
1               5
```

<210> SEQ ID NO 249
<211> LENGTH: 8
<212> TYPE: PRT
<213> ORGANISM: Artificial Sequence
<220> FEATURE:
<223> OTHER INFORMATION: p53.273 peptide 34.0050

<400> SEQUENCE: 249

```
Arg Val Cys Ala Cys Pro Gly Arg
1               5
```

<210> SEQ ID NO 250
<211> LENGTH: 8
<212> TYPE: PRT
<213> ORGANISM: Artificial Sequence
<220> FEATURE:
<223> OTHER INFORMATION: p53.132 peptide 34.0051

<400> SEQUENCE: 250

```
Lys Met Phe Cys Gln Leu Ala Lys
1               5
```

<210> SEQ ID NO 251
<211> LENGTH: 8
<212> TYPE: PRT
<213> ORGANISM: Artificial Sequence
<220> FEATURE:
<223> OTHER INFORMATION: p53.363 peptide 34.0062

<400> SEQUENCE: 251

```
Arg Ala His Ser Ser His Leu Lys
```

```
<210> SEQ ID NO 252
<211> LENGTH: 9
<212> TYPE: PRT
<213> ORGANISM: Artificial Sequence
<220> FEATURE:
<223> OTHER INFORMATION: CEA.656 peptide 34.0148

<400> SEQUENCE: 252

Phe Val Ser Asn Leu Ala Thr Gly Arg
 1               5

<210> SEQ ID NO 253
<211> LENGTH: 9
<212> TYPE: PRT
<213> ORGANISM: Artificial Sequence
<220> FEATURE:
<223> OTHER INFORMATION: CEA.546 peptide 34.0152

<400> SEQUENCE: 253

Arg Leu Gln Leu Ser Asn Gly Asn Lys
 1               5

<210> SEQ ID NO 254
<211> LENGTH: 9
<212> TYPE: PRT
<213> ORGANISM: Artificial Sequence
<220> FEATURE:
<223> OTHER INFORMATION: CEA.628 peptide 34.0153

<400> SEQUENCE: 254

Arg Ile Asn Gly Ile Pro Gln Gln Lys
 1               5

<210> SEQ ID NO 255
<211> LENGTH: 9
<212> TYPE: PRT
<213> ORGANISM: Artificial Sequence
<220> FEATURE:
<223> OTHER INFORMATION: HER2/neu.681 peptide 34.0154

<400> SEQUENCE: 255

Lys Ile Arg Lys Tyr Thr Met Arg Lys
 1               5

<210> SEQ ID NO 256
<211> LENGTH: 9
<212> TYPE: PRT
<213> ORGANISM: Artificial Sequence
<220> FEATURE:
<223> OTHER INFORMATION: MAGE2.116 peptide 34.0155

<400> SEQUENCE: 256

Leu Val His Phe Leu Leu Leu Lys Lys
 1               5

<210> SEQ ID NO 257
<211> LENGTH: 9
<212> TYPE: PRT
<213> ORGANISM: Artificial Sequence
<220> FEATURE:
<223> OTHER INFORMATION: MAGE2.226 peptide 34.0156

<400> SEQUENCE: 257

Ser Met Leu Glu Val Phe Glu Gly Lys
 1               5
```

<210> SEQ ID NO 258
<211> LENGTH: 9
<212> TYPE: PRT
<213> ORGANISM: Artificial Sequence
<220> FEATURE:
<223> OTHER INFORMATION: MAGE2.69 peptide 34.0157

<400> SEQUENCE: 258

Ser Ser Phe Ser Thr Thr Ile Asn Lys
1               5

<210> SEQ ID NO 259
<211> LENGTH: 9
<212> TYPE: PRT
<213> ORGANISM: Artificial Sequence
<220> FEATURE:
<223> OTHER INFORMATION: MAGE2.281 peptide 34.0158

<400> SEQUENCE: 259

Thr Ser Tyr Val Lys Val Leu His Lys
1               5

<210> SEQ ID NO 260
<211> LENGTH: 9
<212> TYPE: PRT
<213> ORGANISM: Artificial Sequence
<220> FEATURE:
<223> OTHER INFORMATION: MAGE2.149 peptide 34.0159

<400> SEQUENCE: 260

Val Ile Phe Ser Lys Ala Ser Glu Lys
1               5

<210> SEQ ID NO 261
<211> LENGTH: 9
<212> TYPE: PRT
<213> ORGANISM: Artificial Sequence
<220> FEATURE:
<223> OTHER INFORMATION: MAGE3.130 peptide 34.0160

<400> SEQUENCE: 261

Gly Ser Val Val Gly Asn Trp Gln Lys
1               5

<210> SEQ ID NO 262
<211> LENGTH: 9
<212> TYPE: PRT
<213> ORGANISM: Artificial Sequence
<220> FEATURE:
<223> OTHER INFORMATION: MAGE3.69 peptide 34.0161

<400> SEQUENCE: 262

Ser Ser Leu Pro Thr Thr Met Asn Lys
1               5

<210> SEQ ID NO 263
<211> LENGTH: 9
<212> TYPE: PRT
<213> ORGANISM: Artificial Sequence
<220> FEATURE:
<223> OTHER INFORMATION: MAGE3.226 peptide 34.0162

<400> SEQUENCE: 263

Ser Val Leu Glu Val Phe Glu Gly Lys
1               5

```
<210> SEQ ID NO 264
<211> LENGTH: 9
<212> TYPE: PRT
<213> ORGANISM: Artificial Sequence
<220> FEATURE:
<223> OTHER INFORMATION: p53.240 peptide 34.0171

<400> SEQUENCE: 264

Ser Ser Asx Met Gly Gly Met Asn Lys
 1               5

<210> SEQ ID NO 265
<211> LENGTH: 9
<212> TYPE: PRT
<213> ORGANISM: Artificial Sequence
<220> FEATURE:
<223> OTHER INFORMATION: p53.240 peptide 34.0172

<400> SEQUENCE: 265

Ser Ser Cys Met Gly Gly Met Asn Lys
 1               5

<210> SEQ ID NO 266
<211> LENGTH: 10
<212> TYPE: PRT
<213> ORGANISM: Artificial Sequence
<220> FEATURE:
<223> OTHER INFORMATION: CEA.554 peptide 34.0211

<400> SEQUENCE: 266

Arg Thr Leu Thr Leu Phe Asn Val Thr Lys
 1               5                  10

<210> SEQ ID NO 267
<211> LENGTH: 10
<212> TYPE: PRT
<213> ORGANISM: Artificial Sequence
<220> FEATURE:
<223> OTHER INFORMATION: CEA.241 peptide 34.0212

<400> SEQUENCE: 267

Thr Ile Ser Pro Leu Asn Thr Ser Tyr Lys
 1               5                  10

<210> SEQ ID NO 268
<211> LENGTH: 10
<212> TYPE: PRT
<213> ORGANISM: Artificial Sequence
<220> FEATURE:
<223> OTHER INFORMATION: MAGE2.72 peptide 34.0214

<400> SEQUENCE: 268

Ser Thr Thr Ile Asn Tyr Thr Leu Trp Lys
 1               5                  10

<210> SEQ ID NO 269
<211> LENGTH: 10
<212> TYPE: PRT
<213> ORGANISM: Artificial Sequence
<220> FEATURE:
<223> OTHER INFORMATION: MAGE3.68 peptide 34.0215

<400> SEQUENCE: 269

Ala Ser Ser Leu Pro Thr Thr Met Asn Lys
 1               5                  10
```

```
<210> SEQ ID NO 270
<211> LENGTH: 10
<212> TYPE: PRT
<213> ORGANISM: Artificial Sequence
<220> FEATURE:
<223> OTHER INFORMATION: p53.101 peptide 34.0225

<400> SEQUENCE: 270

Lys Thr Tyr Gln Gly Ser Tyr Gly Phe Lys
 1               5                   10

<210> SEQ ID NO 271
<211> LENGTH: 10
<212> TYPE: PRT
<213> ORGANISM: Artificial Sequence
<220> FEATURE:
<223> OTHER INFORMATION: p53.172 peptide 34.0226

<400> SEQUENCE: 271

Val Val Arg Arg Asx Pro His His Glu Lys
 1               5                   10

<210> SEQ ID NO 272
<211> LENGTH: 10
<212> TYPE: PRT
<213> ORGANISM: Artificial Sequence
<220> FEATURE:
<223> OTHER INFORMATION: p53.187 peptide 34.0228

<400> SEQUENCE: 272

Gly Leu Ala Pro Pro Gln His Leu Ile Lys
 1               5                   10

<210> SEQ ID NO 273
<211> LENGTH: 10
<212> TYPE: PRT
<213> ORGANISM: Artificial Sequence
<220> FEATURE:
<223> OTHER INFORMATION: p53.239 peptide 34.0229

<400> SEQUENCE: 273

Asn Ser Ser Cys Met Gly Gly Met Asn Lys
 1               5                   10

<210> SEQ ID NO 274
<211> LENGTH: 10
<212> TYPE: PRT
<213> ORGANISM: Artificial Sequence
<220> FEATURE:
<223> OTHER INFORMATION: p53.240 peptide 34.0230

<400> SEQUENCE: 274

Ser Ser Asx Met Gly Gly Met Asn Arg Lys
 1               5                   10

<210> SEQ ID NO 275
<211> LENGTH: 10
<212> TYPE: PRT
<213> ORGANISM: Artificial Sequence
<220> FEATURE:
<223> OTHER INFORMATION: p53.273 peptide 34.0232

<400> SEQUENCE: 275

Arg Val Cys Ala Cys Pro Gly Arg Asp Lys
 1               5                   10

<210> SEQ ID NO 276
```

```
<211> LENGTH: 11
<212> TYPE: PRT
<213> ORGANISM: Artificial Sequence
<220> FEATURE:
<223> OTHER INFORMATION: CEA.492 peptide 34.0295

<400> SEQUENCE: 276

Lys Thr Ile Thr Val Ser Ala Glu Leu Pro Lys
 1               5                  10

<210> SEQ ID NO 277
<211> LENGTH: 11
<212> TYPE: PRT
<213> ORGANISM: Artificial Sequence
<220> FEATURE:
<223> OTHER INFORMATION: CEA.314 peptide 34.0296

<400> SEQUENCE: 277

Thr Thr Ile Thr Val Tyr Ala Glu Pro Pro Lys
 1               5                  10

<210> SEQ ID NO 278
<211> LENGTH: 11
<212> TYPE: PRT
<213> ORGANISM: Artificial Sequence
<220> FEATURE:
<223> OTHER INFORMATION: CEA.418 peptide 34.0298

<400> SEQUENCE: 278

Pro Thr Ile Ser Pro Ser Tyr Thr Tyr Tyr Arg
 1               5                  10

<210> SEQ ID NO 279
<211> LENGTH: 11
<212> TYPE: PRT
<213> ORGANISM: Artificial Sequence
<220> FEATURE:
<223> OTHER INFORMATION: MAGE2.188 peptide 34.0301

<400> SEQUENCE: 279

Gly Leu Leu Gly Asp Asn Gln Val Met Pro Lys
 1               5                  10

<210> SEQ ID NO 280
<211> LENGTH: 11
<212> TYPE: PRT
<213> ORGANISM: Artificial Sequence
<220> FEATURE:
<223> OTHER INFORMATION: MAGE2.113 peptide 34.0306

<400> SEQUENCE: 280

Met Val Glu Leu Val His Phe Leu Leu Leu Lys
 1               5                  10

<210> SEQ ID NO 281
<211> LENGTH: 11
<212> TYPE: PRT
<213> ORGANISM: Artificial Sequence
<220> FEATURE:
<223> OTHER INFORMATION: MAGE2.71 peptide 34.0308

<400> SEQUENCE: 281

Phe Ser Thr Thr Ile Asn Tyr Thr Leu Trp Arg
 1               5                  10

<210> SEQ ID NO 282
<211> LENGTH: 11
```

<212> TYPE: PRT
<213> ORGANISM: Artificial Sequence
<220> FEATURE:
<223> OTHER INFORMATION: MAGE3.188 peptide 34.0311

<400> SEQUENCE: 282

Gly Leu Leu Gly Asp Asn Gln Ile Met Pro Lys
 1               5                  10

<210> SEQ ID NO 283
<211> LENGTH: 11
<212> TYPE: PRT
<213> ORGANISM: Artificial Sequence
<220> FEATURE:
<223> OTHER INFORMATION: p53.110 peptide 34.0317

<400> SEQUENCE: 283

Arg Leu Gly Phe Leu His Ser Gly Thr Ala Lys
 1               5                  10

<210> SEQ ID NO 284
<211> LENGTH: 11
<212> TYPE: PRT
<213> ORGANISM: Artificial Sequence
<220> FEATURE:
<223> OTHER INFORMATION: p53.129 peptide 34.0318

<400> SEQUENCE: 284

Ala Leu Asn Lys Met Phe Cys Gln Leu Ala Lys
 1               5                  10

<210> SEQ ID NO 285
<211> LENGTH: 11
<212> TYPE: PRT
<213> ORGANISM: Artificial Sequence
<220> FEATURE:
<223> OTHER INFORMATION: p53.273 peptide 34.0323

<400> SEQUENCE: 285

Arg Val Cys Ala Cys Pro Gly Arg Asp Arg Arg
 1               5                  10

<210> SEQ ID NO 286
<211> LENGTH: 11
<212> TYPE: PRT
<213> ORGANISM: Artificial Sequence
<220> FEATURE:
<223> OTHER INFORMATION: p53.14 peptide 34.0324

<400> SEQUENCE: 286

Leu Ser Gln Glu Thr Phe Ser Asp Leu Trp Lys
 1               5                  10

<210> SEQ ID NO 287
<211> LENGTH: 11
<212> TYPE: PRT
<213> ORGANISM: Artificial Sequence
<220> FEATURE:
<223> OTHER INFORMATION: p53.363 peptide 34.0328

<400> SEQUENCE: 287

Arg Ala His Ser Ser His Leu Lys Ser Lys Lys
 1               5                  10

<210> SEQ ID NO 288
<211> LENGTH: 11
<212> TYPE: PRT

```
<213> ORGANISM: Artificial Sequence
<220> FEATURE:
<223> OTHER INFORMATION: p53.122 peptide 34.0329

<400> SEQUENCE: 288

Val Thr Cys Thr Tyr Ser Pro Ala Leu Asn Lys
1               5                   10

<210> SEQ ID NO 289
<211> LENGTH: 11
<212> TYPE: PRT
<213> ORGANISM: Artificial Sequence
<220> FEATURE:
<223> OTHER INFORMATION: p53.154 peptide 34.0330

<400> SEQUENCE: 289

Gly Thr Arg Val Arg Ala Met Ala Ile Tyr Lys
1               5                   10

<210> SEQ ID NO 290
<211> LENGTH: 11
<212> TYPE: PRT
<213> ORGANISM: Artificial Sequence
<220> FEATURE:
<223> OTHER INFORMATION: p53.376 peptide 34.0332

<400> SEQUENCE: 290

Ser Thr Ser Arg His Lys Lys Leu Met Phe Lys
1               5                   10

<210> SEQ ID NO 291
<211> LENGTH: 9
<212> TYPE: PRT
<213> ORGANISM: Artificial Sequence
<220> FEATURE:
<223> OTHER INFORMATION: Her2/neu.846 peptide 40.0107

<400> SEQUENCE: 291

Leu Ala Ala Arg Asn Val Leu Val Lys
1               5

<210> SEQ ID NO 292
<211> LENGTH: 9
<212> TYPE: PRT
<213> ORGANISM: Artificial Sequence
<220> FEATURE:
<223> OTHER INFORMATION: Her2/neu.889 peptide 40.0109

<400> SEQUENCE: 292

Met Ala Leu Glu Ser Ile Leu Arg Arg
1               5

<210> SEQ ID NO 293
<211> LENGTH: 10
<212> TYPE: PRT
<213> ORGANISM: Artificial Sequence
<220> FEATURE:
<223> OTHER INFORMATION: Her2/neu.450 peptide 40.0145

<400> SEQUENCE: 293

Ile Ser Trp Leu Gly Leu Arg Ser Leu Arg
1               5                   10

<210> SEQ ID NO 294
<211> LENGTH: 10
<212> TYPE: PRT
<213> ORGANISM: Artificial Sequence
```

```
<220> FEATURE:
<223> OTHER INFORMATION: Her2/neu.727 peptide 40.0147

<400> SEQUENCE: 294

Gly Ser Gly Ala Phe Gly Thr Val Tyr Lys
1               5                   10

<210> SEQ ID NO 295
<211> LENGTH: 10
<212> TYPE: PRT
<213> ORGANISM: Artificial Sequence
<220> FEATURE:
<223> OTHER INFORMATION: Her2/neu.997 peptide 40.0153

<400> SEQUENCE: 295

Ala Ser Pro Leu Asp Ser Thr Phe Tyr Arg
1               5                   10

<210> SEQ ID NO 296
<211> LENGTH: 8
<212> TYPE: PRT
<213> ORGANISM: Artificial Sequence
<220> FEATURE:
<223> OTHER INFORMATION: CEA.680I8 peptide 40.0013

<400> SEQUENCE: 296

Ser Pro Gly Leu Ser Ala Gly Ile
1               5

<210> SEQ ID NO 297
<211> LENGTH: 8
<212> TYPE: PRT
<213> ORGANISM: Artificial Sequence
<220> FEATURE:
<223> OTHER INFORMATION: Her2/neu.921 peptide 40.0022

<400> SEQUENCE: 297

Lys Pro Tyr Asp Gly Ile Pro Ala
1               5

<210> SEQ ID NO 298
<211> LENGTH: 8
<212> TYPE: PRT
<213> ORGANISM: Artificial Sequence
<220> FEATURE:
<223> OTHER INFORMATION: Her2/neu.921I8 peptide 40.0023

<400> SEQUENCE: 298

Lys Pro Tyr Asp Gly Ile Pro Ile
1               5

<210> SEQ ID NO 299
<211> LENGTH: 8
<212> TYPE: PRT
<213> ORGANISM: Artificial Sequence
<220> FEATURE:
<223> OTHER INFORMATION: p53.63 peptide 40.0050

<400> SEQUENCE: 299

Ala Pro Arg Met Pro Glu Ala Ala
1               5

<210> SEQ ID NO 300
<211> LENGTH: 8
<212> TYPE: PRT
<213> ORGANISM: Artificial Sequence
<220> FEATURE:
```

-continued

<223> OTHER INFORMATION: p53.63I8 peptide 40.0051

<400> SEQUENCE: 300

Ala Pro Arg Met Pro Glu Ala Ile
1               5

<210> SEQ ID NO 301
<211> LENGTH: 8
<212> TYPE: PRT
<213> ORGANISM: Artificial Sequence
<220> FEATURE:
<223> OTHER INFORMATION: p53.76I8 peptide 40.0055

<400> SEQUENCE: 301

Ala Pro Ala Ala Pro Thr Pro Ile
1               5

<210> SEQ ID NO 302
<211> LENGTH: 8
<212> TYPE: PRT
<213> ORGANISM: Artificial Sequence
<220> FEATURE:
<223> OTHER INFORMATION: p53.79I8 peptide 40.0057

<400> SEQUENCE: 302

Ala Pro Thr Pro Ala Ala Pro Ile
1               5

<210> SEQ ID NO 303
<211> LENGTH: 8
<212> TYPE: PRT
<213> ORGANISM: Artificial Sequence
<220> FEATURE:
<223> OTHER INFORMATION: p53.81I8 peptide 40.0059

<400> SEQUENCE: 303

Thr Pro Ala Ala Pro Ala Pro Ile
1               5

<210> SEQ ID NO 304
<211> LENGTH: 8
<212> TYPE: PRT
<213> ORGANISM: Artificial Sequence
<220> FEATURE:
<223> OTHER INFORMATION: p53.84I8 peptide 40.0061

<400> SEQUENCE: 304

Ala Pro Ala Pro Ala Pro Ser Ile
1               5

<210> SEQ ID NO 305
<211> LENGTH: 8
<212> TYPE: PRT
<213> ORGANISM: Artificial Sequence
<220> FEATURE:
<223> OTHER INFORMATION: p53.127 peptide 40.0062

<400> SEQUENCE: 305

Ser Pro Ala Leu Asn Lys Met Phe
1               5

<210> SEQ ID NO 306
<211> LENGTH: 8
<212> TYPE: PRT
<213> ORGANISM: Artificial Sequence
<220> FEATURE:
<223> OTHER INFORMATION: p53.127I8 peptide 40.0063

```
<400> SEQUENCE: 306

Ser Pro Ala Leu Asn Lys Met Ile
1               5

<210> SEQ ID NO 307
<211> LENGTH: 9
<212> TYPE: PRT
<213> ORGANISM: Artificial Sequence
<220> FEATURE:
<223> OTHER INFORMATION: CEA.3I9 peptide 40.0117

<400> SEQUENCE: 307

Ser Pro Ser Ala Pro Pro His Arg Ile
1               5

<210> SEQ ID NO 308
<211> LENGTH: 9
<212> TYPE: PRT
<213> ORGANISM: Artificial Sequence
<220> FEATURE:
<223> OTHER INFORMATION: CEA.7I9 peptide 40.0119

<400> SEQUENCE: 308

Pro Pro His Arg Trp Cys Ile Pro Ile
1               5

<210> SEQ ID NO 309
<211> LENGTH: 9
<212> TYPE: PRT
<213> ORGANISM: Artificial Sequence
<220> FEATURE:
<223> OTHER INFORMATION: CEA.92 peptide 40.0120

<400> SEQUENCE: 309

Gly Pro Ala Tyr Ser Gly Arg Glu Ile
1               5

<210> SEQ ID NO 310
<211> LENGTH: 11
<212> TYPE: PRT
<213> ORGANISM: Artificial Sequence
<220> FEATURE:
<223> OTHER INFORMATION: Her2/neu.706I10 peptide 40.0156

<400> SEQUENCE: 310

Met Pro Asn Gln Ala Gln Met Arg Ile Leu Ile
1               5                   10

<210> SEQ ID NO 311
<211> LENGTH: 11
<212> TYPE: PRT
<213> ORGANISM: Artificial Sequence
<220> FEATURE:
<223> OTHER INFORMATION: Her2/neu.801I10 peptide 40.0157

<400> SEQUENCE: 311

Met Pro Tyr Gly Cys Leu Leu Asp His Val Ile
1               5                   10

<210> SEQ ID NO 312
<211> LENGTH: 10
<212> TYPE: PRT
<213> ORGANISM: Artificial Sequence
<220> FEATURE:
<223> OTHER INFORMATION: CEA.6 peptide 40.0161
```

```
<400> SEQUENCE: 312

Ala Pro Pro His Arg Trp Cys Ile Pro Trp
1               5                   10

<210> SEQ ID NO 313
<211> LENGTH: 10
<212> TYPE: PRT
<213> ORGANISM: Artificial Sequence
<220> FEATURE:
<223> OTHER INFORMATION: CEA.6I10 peptide 40.0162

<400> SEQUENCE: 313

Ala Pro Pro His Arg Trp Cys Ile Pro Ile
1               5                   10

<210> SEQ ID NO 314
<211> LENGTH: 10
<212> TYPE: PRT
<213> ORGANISM: Artificial Sequence
<220> FEATURE:
<223> OTHER INFORMATION: CEA.13 peptide 40.0163

<400> SEQUENCE: 314

Ile Pro Trp Gln Arg Leu Leu Leu Thr Ala
1               5                   10

<210> SEQ ID NO 315
<211> LENGTH: 10
<212> TYPE: PRT
<213> ORGANISM: Artificial Sequence
<220> FEATURE:
<223> OTHER INFORMATION: CEA.13I10 peptide 40.0164

<400> SEQUENCE: 315

Ile Pro Trp Gln Arg Leu Leu Leu Thr Ile
1               5                   10

<210> SEQ ID NO 316
<211> LENGTH: 10
<212> TYPE: PRT
<213> ORGANISM: Artificial Sequence
<220> FEATURE:
<223> OTHER INFORMATION: CEA.58I10 peptide 40.0166

<400> SEQUENCE: 316

Leu Pro Gln His Leu Phe Gly Tyr Ser Ile
1               5                   10

<210> SEQ ID NO 317
<211> LENGTH: 11
<212> TYPE: PRT
<213> ORGANISM: Artificial Sequence
<220> FEATURE:
<223> OTHER INFORMATION: Her2/neu.966 peptide 40.0201

<400> SEQUENCE: 317

Arg Pro Arg Phe Arg Glu Leu Val Ser Glu Phe
1               5                   10

<210> SEQ ID NO 318
<211> LENGTH: 11
<212> TYPE: PRT
<213> ORGANISM: Artificial Sequence
<220> FEATURE:
<223> OTHER INFORMATION: Her2/neu.966I11 peptide 40.0202

<400> SEQUENCE: 318
```

```
Arg Pro Arg Phe Arg Glu Leu Val Ser Glu Ile
1               5                   10
```

<210> SEQ ID NO 319
<211> LENGTH: 11
<212> TYPE: PRT
<213> ORGANISM: Artificial Sequence
<220> FEATURE:
<223> OTHER INFORMATION: Her2/neu.1149 peptide 40.0205

<400> SEQUENCE: 319

```
Pro Pro Ser Pro Arg Glu Gly Pro Leu Pro Ala
1               5                   10
```

<210> SEQ ID NO 320
<211> LENGTH: 11
<212> TYPE: PRT
<213> ORGANISM: Artificial Sequence
<220> FEATURE:
<223> OTHER INFORMATION: Her2/neu.1149I11 peptide 40.0206

<400> SEQUENCE: 320

```
Pro Pro Ser Pro Arg Glu Gly Pro Leu Pro Ile
1               5                   10
```

<210> SEQ ID NO 321
<211> LENGTH: 11
<212> TYPE: PRT
<213> ORGANISM: Artificial Sequence
<220> FEATURE:
<223> OTHER INFORMATION: Her2/neu.1155 peptide 40.0207

<400> SEQUENCE: 321

```
Gly Pro Leu Pro Ala Ala Arg Pro Ala Gly Ala
1               5                   10
```

<210> SEQ ID NO 322
<211> LENGTH: 11
<212> TYPE: PRT
<213> ORGANISM: Artificial Sequence
<220> FEATURE:
<223> OTHER INFORMATION: Her2/neu.1155I11 peptide 40.0208

<400> SEQUENCE: 322

```
Gly Pro Leu Pro Ala Ala Arg Pro Ala Gly Ile
1               5                   10
```

<210> SEQ ID NO 323
<211> LENGTH: 11
<212> TYPE: PRT
<213> ORGANISM: Artificial Sequence
<220> FEATURE:
<223> OTHER INFORMATION: p53.74 peptide 40.0231

<400> SEQUENCE: 323

```
Ala Pro Ala Pro Ala Ala Pro Thr Pro Ala Ala
1               5                   10
```

<210> SEQ ID NO 324
<211> LENGTH: 11
<212> TYPE: PRT
<213> ORGANISM: Artificial Sequence
<220> FEATURE:
<223> OTHER INFORMATION: p53.74I11 peptide 40.0232

<400> SEQUENCE: 324

```
Ala Pro Ala Pro Ala Ala Pro Thr Pro Ala Ile
 1               5                  10
```

<210> SEQ ID NO 325
<211> LENGTH: 11
<212> TYPE: PRT
<213> ORGANISM: Artificial Sequence
<220> FEATURE:
<223> OTHER INFORMATION: p53.76 peptide 40.0233

<400> SEQUENCE: 325

```
Ala Pro Ala Ala Pro Thr Pro Ala Ala Pro Ala
 1               5                  10
```

<210> SEQ ID NO 326
<211> LENGTH: 11
<212> TYPE: PRT
<213> ORGANISM: Artificial Sequence
<220> FEATURE:
<223> OTHER INFORMATION: p53.76I11 peptide 40.0234

<400> SEQUENCE: 326

```
Ala Pro Ala Ala Pro Thr Pro Ala Ala Pro Ile
 1               5                  10
```

<210> SEQ ID NO 327
<211> LENGTH: 8
<212> TYPE: PRT
<213> ORGANISM: Artificial Sequence
<220> FEATURE:
<223> OTHER INFORMATION: CEA.13.I8 peptide 45.0003

<400> SEQUENCE: 327

```
Ile Pro Trp Gln Arg Leu Leu Ile
 1               5
```

<210> SEQ ID NO 328
<211> LENGTH: 8
<212> TYPE: PRT
<213> ORGANISM: Artificial Sequence
<220> FEATURE:
<223> OTHER INFORMATION: CEA.58.I8 peptide 45.0004

<400> SEQUENCE: 328

```
Leu Pro Gln His Leu Phe Gly Ile
 1               5
```

<210> SEQ ID NO 329
<211> LENGTH: 8
<212> TYPE: PRT
<213> ORGANISM: Artificial Sequence
<220> FEATURE:
<223> OTHER INFORMATION: CEA.428.I8 peptide 45.0007

<400> SEQUENCE: 329

```
Arg Pro Gly Val Asn Leu Ser Ile
 1               5
```

<210> SEQ ID NO 330
<211> LENGTH: 8
<212> TYPE: PRT
<213> ORGANISM: Artificial Sequence
<220> FEATURE:
<223> OTHER INFORMATION: CEA.632.I8 peptide 45.0010

<400> SEQUENCE: 330

```
Ile Pro Gln Gln His Thr Gln Ile
```

-continued

```
1               5

<210> SEQ ID NO 331
<211> LENGTH: 8
<212> TYPE: PRT
<213> ORGANISM: Artificial Sequence
<220> FEATURE:
<223> OTHER INFORMATION: CEA.646.I8 peptide 45.0011

<400> SEQUENCE: 331

Thr Pro Asn Asn Asn Gly Thr Ile
1               5

<210> SEQ ID NO 332
<211> LENGTH: 8
<212> TYPE: PRT
<213> ORGANISM: Artificial Sequence
<220> FEATURE:
<223> OTHER INFORMATION: Her2/neu.315.I8 peptide 45.0016

<400> SEQUENCE: 332

Cys Pro Leu His Asn Gln Glu Ile
1               5

<210> SEQ ID NO 333
<211> LENGTH: 8
<212> TYPE: PRT
<213> ORGANISM: Artificial Sequence
<220> FEATURE:
<223> OTHER INFORMATION: Her2/neu.336.I8 peptide 45.0017

<400> SEQUENCE: 333

Lys Pro Cys Ala Arg Val Cys Ile
1               5

<210> SEQ ID NO 334
<211> LENGTH: 8
<212> TYPE: PRT
<213> ORGANISM: Artificial Sequence
<220> FEATURE:
<223> OTHER INFORMATION: Her2/neu.415.I8 peptide 45.0019

<400> SEQUENCE: 334

Trp Pro Asp Ser Leu Pro Asp Ile
1               5

<210> SEQ ID NO 335
<211> LENGTH: 8
<212> TYPE: PRT
<213> ORGANISM: Artificial Sequence
<220> FEATURE:
<223> OTHER INFORMATION: Her2/neu.779.I8 peptide 45.0023

<400> SEQUENCE: 335

Ser Pro Tyr Val Ser Arg Leu Ile
1               5

<210> SEQ ID NO 336
<211> LENGTH: 8
<212> TYPE: PRT
<213> ORGANISM: Artificial Sequence
<220> FEATURE:
<223> OTHER INFORMATION: Her2/neu.884.I8 peptide 45.0024

<400> SEQUENCE: 336

Val Pro Ile Lys Trp Met Ala Ile
1               5
```

-continued

```
<210> SEQ ID NO 337
<211> LENGTH: 8
<212> TYPE: PRT
<213> ORGANISM: Artificial Sequence
<220> FEATURE:
<223> OTHER INFORMATION: Her2/neu.966I8 peptide 45.0026

<400> SEQUENCE: 337

Arg Pro Arg Phe Arg Glu Leu Ile
 1               5

<210> SEQ ID NO 338
<211> LENGTH: 8
<212> TYPE: PRT
<213> ORGANISM: Artificial Sequence
<220> FEATURE:
<223> OTHER INFORMATION: Her2/neu.1036.I8 peptide 45.0028

<400> SEQUENCE: 338

Ala Pro Gly Ala Gly Gly Met Ile
 1               5

<210> SEQ ID NO 339
<211> LENGTH: 8
<212> TYPE: PRT
<213> ORGANISM: Artificial Sequence
<220> FEATURE:
<223> OTHER INFORMATION: Her2/neu.1174.I8 peptide 45.0031

<400> SEQUENCE: 339

Ser Pro Gly Lys Asn Gly Val Ile
 1               5

<210> SEQ ID NO 340
<211> LENGTH: 8
<212> TYPE: PRT
<213> ORGANISM: Artificial Sequence
<220> FEATURE:
<223> OTHER INFORMATION: MAGE3.64.I8 peptide 45.0037

<400> SEQUENCE: 340

Ser Pro Gln Gly Ala Ser Ser Ile
 1               5

<210> SEQ ID NO 341
<211> LENGTH: 8
<212> TYPE: PRT
<213> ORGANISM: Artificial Sequence
<220> FEATURE:
<223> OTHER INFORMATION: MAGE3.77.I8 peptide 45.0038

<400> SEQUENCE: 341

Tyr Pro Leu Trp Ser Gln Ser Ile
 1               5

<210> SEQ ID NO 342
<211> LENGTH: 8
<212> TYPE: PRT
<213> ORGANISM: Artificial Sequence
<220> FEATURE:
<223> OTHER INFORMATION: p53.33.I8 peptide 45.0044

<400> SEQUENCE: 342

Ser Pro Leu Pro Ser Gln Ala Ile
 1               5
```

-continued

```
<210> SEQ ID NO 343
<211> LENGTH: 8
<212> TYPE: PRT
<213> ORGANISM: Artificial Sequence
<220> FEATURE:
<223> OTHER INFORMATION: p53.66.I8 peptide 45.0046

<400> SEQUENCE: 343

Met Pro Glu Ala Ala Pro Pro Ile
 1               5

<210> SEQ ID NO 344
<211> LENGTH: 8
<212> TYPE: PRT
<213> ORGANISM: Artificial Sequence
<220> FEATURE:
<223> OTHER INFORMATION: p53.86.I8 peptide 45.0047

<400> SEQUENCE: 344

Ala Pro Ala Pro Ser Trp Pro Ile
 1               5

<210> SEQ ID NO 345
<211> LENGTH: 9
<212> TYPE: PRT
<213> ORGANISM: Artificial Sequence
<220> FEATURE:
<223> OTHER INFORMATION: CEA.155.I9 peptide 45.0051

<400> SEQUENCE: 345

Lys Pro Val Glu Asp Lys Asp Ala Ile
 1               5

<210> SEQ ID NO 346
<211> LENGTH: 9
<212> TYPE: PRT
<213> ORGANISM: Artificial Sequence
<220> FEATURE:
<223> OTHER INFORMATION: CEA.632.I9 peptide 45.0054

<400> SEQUENCE: 346

Ile Pro Gln Gln His Thr Gln Val Ile
 1               5

<210> SEQ ID NO 347
<211> LENGTH: 9
<212> TYPE: PRT
<213> ORGANISM: Artificial Sequence
<220> FEATURE:
<223> OTHER INFORMATION: p53.70.I9 peptide 45.0060

<400> SEQUENCE: 347

Ala Pro Pro Val Ala Pro Ala Pro Ile
 1               5

<210> SEQ ID NO 348
<211> LENGTH: 9
<212> TYPE: PRT
<213> ORGANISM: Artificial Sequence
<220> FEATURE:
<223> OTHER INFORMATION: p53.76.I9 peptide 45.0062

<400> SEQUENCE: 348

Ala Pro Ala Ala Pro Thr Pro Ala Ile
 1               5
```

```
<210> SEQ ID NO 349
<211> LENGTH: 9
<212> TYPE: PRT
<213> ORGANISM: Artificial Sequence
<220> FEATURE:
<223> OTHER INFORMATION: p53.152.I9 peptide 45.0064

<400> SEQUENCE: 349

Pro Pro Gly Thr Arg Val Arg Ala Ile
 1               5

<210> SEQ ID NO 350
<211> LENGTH: 9
<212> TYPE: PRT
<213> ORGANISM: Artificial Sequence
<220> FEATURE:
<223> OTHER INFORMATION: p53.189.I9 peptide 45.0065

<400> SEQUENCE: 350

Ala Pro Pro Gln His Leu Ile Arg Ile
 1               5

<210> SEQ ID NO 351
<211> LENGTH: 10
<212> TYPE: PRT
<213> ORGANISM: Artificial Sequence
<220> FEATURE:
<223> OTHER INFORMATION: CEA.632.I10 peptide 45.0071

<400> SEQUENCE: 351

Ile Pro Gln Gln His Thr Gln Val Leu Ile
 1               5                  10

<210> SEQ ID NO 352
<211> LENGTH: 10
<212> TYPE: PRT
<213> ORGANISM: Artificial Sequence
<220> FEATURE:
<223> OTHER INFORMATION: CEA.680.I10 peptide 45.0072

<400> SEQUENCE: 352

Ser Pro Gly Leu Ser Ala Gly Ala Thr Ile
 1               5                  10

<210> SEQ ID NO 353
<211> LENGTH: 10
<212> TYPE: PRT
<213> ORGANISM: Artificial Sequence
<220> FEATURE:
<223> OTHER INFORMATION: Her2/neu.196.I10 peptide 45.0073

<400> SEQUENCE: 353

Ser Pro Met Cys Lys Gly Ser Arg Cys Ile
 1               5                  10

<210> SEQ ID NO 354
<211> LENGTH: 10
<212> TYPE: PRT
<213> ORGANISM: Artificial Sequence
<220> FEATURE:
<223> OTHER INFORMATION: Her2/neu.282.I10 peptide 45.0074

<400> SEQUENCE: 354

Met Pro Asn Pro Glu Gly Arg Tyr Thr Ile
 1               5                  10

<210> SEQ ID NO 355
```

```
<211> LENGTH: 10
<212> TYPE: PRT
<213> ORGANISM: Artificial Sequence
<220> FEATURE:
<223> OTHER INFORMATION: Her2/neu.315.I10 peptide 45.0076

<400> SEQUENCE: 355

Cys Pro Leu His Asn Gln Glu Val Thr Ile
 1               5                  10

<210> SEQ ID NO 356
<211> LENGTH: 10
<212> TYPE: PRT
<213> ORGANISM: Artificial Sequence
<220> FEATURE:
<223> OTHER INFORMATION: Her2/neu.605.I10 peptide 45.0079

<400> SEQUENCE: 356

Lys Pro Asp Leu Ser Tyr Met Pro Ile Ile
 1               5                  10

<210> SEQ ID NO 357
<211> LENGTH: 10
<212> TYPE: PRT
<213> ORGANISM: Artificial Sequence
<220> FEATURE:
<223> OTHER INFORMATION: Her2/neu.701.I10 peptide 45.0080

<400> SEQUENCE: 357

Thr Pro Ser Gly Ala Met Pro Asn Gln Ile
 1               5                  10

<210> SEQ ID NO 358
<211> LENGTH: 10
<212> TYPE: PRT
<213> ORGANISM: Artificial Sequence
<220> FEATURE:
<223> OTHER INFORMATION: Her2/neu.995.I10 peptide 45.0084

<400> SEQUENCE: 358

Gly Pro Ala Ser Pro Leu Asp Ser Thr Ile
 1               5                  10

<210> SEQ ID NO 359
<211> LENGTH: 10
<212> TYPE: PRT
<213> ORGANISM: Artificial Sequence
<220> FEATURE:
<223> OTHER INFORMATION: p53.70.I10 peptide 45.0091

<400> SEQUENCE: 359

Ala Pro Pro Val Ala Pro Ala Pro Ala Ile
 1               5                  10

<210> SEQ ID NO 360
<211> LENGTH: 10
<212> TYPE: PRT
<213> ORGANISM: Artificial Sequence
<220> FEATURE:
<223> OTHER INFORMATION: p53.74.I10 peptide 45.0092

<400> SEQUENCE: 360

Ala Pro Ala Pro Ala Ala Pro Thr Pro Ile
 1               5                  10

<210> SEQ ID NO 361
<211> LENGTH: 10
```

```
<212> TYPE: PRT
<213> ORGANISM: Artificial Sequence
<220> FEATURE:
<223> OTHER INFORMATION: p53.79.I10 peptide 45.0093

<400> SEQUENCE: 361

Ala Pro Thr Pro Ala Ala Pro Ala Pro Ile
 1               5                  10

<210> SEQ ID NO 362
<211> LENGTH: 10
<212> TYPE: PRT
<213> ORGANISM: Artificial Sequence
<220> FEATURE:
<223> OTHER INFORMATION: p53.88.I10 peptide 45.0094

<400> SEQUENCE: 362

Ala Pro Ser Trp Pro Leu Ser Ser Ser Ile
 1               5                  10

<210> SEQ ID NO 363
<211> LENGTH: 11
<212> TYPE: PRT
<213> ORGANISM: Artificial Sequence
<220> FEATURE:
<223> OTHER INFORMATION: CEA.239.I11 peptide 45.103

<400> SEQUENCE: 363

Ala Pro Thr Ile Ser Pro Leu Asn Thr Ser Ile
 1               5                  10

<210> SEQ ID NO 364
<211> LENGTH: 11
<212> TYPE: PRT
<213> ORGANISM: Artificial Sequence
<220> FEATURE:
<223> OTHER INFORMATION: CEA.421.I11 peptide 45.0108

<400> SEQUENCE: 364

Ser Pro Ser Tyr Thr Tyr Tyr Arg Pro Gly Ile
 1               5                  10

<210> SEQ ID NO 365
<211> LENGTH: 11
<212> TYPE: PRT
<213> ORGANISM: Artificial Sequence
<220> FEATURE:
<223> OTHER INFORMATION: Her2/neu.600.I11 peptide 45.0117

<400> SEQUENCE: 365

Cys Pro Ser Gly Val Lys Pro Asp Leu Ser Ile
 1               5                  10

<210> SEQ ID NO 366
<211> LENGTH: 11
<212> TYPE: PRT
<213> ORGANISM: Artificial Sequence
<220> FEATURE:
<223> OTHER INFORMATION: Her2/neu.649.I11 peptide 45.0118

<400> SEQUENCE: 366

Ser Pro Leu Thr Ser Ile Ile Ser Ala Val Ile
 1               5                  10

<210> SEQ ID NO 367
<211> LENGTH: 11
<212> TYPE: PRT
```

```
<213> ORGANISM: Artificial Sequence
<220> FEATURE:
<223> OTHER INFORMATION: Her2/neu.740.I11 peptide 45.0119

<400> SEQUENCE: 367

Ile Pro Asp Gly Glu Asn Val Lys Ile Pro Ile
1               5                   10

<210> SEQ ID NO 368
<211> LENGTH: 11
<212> TYPE: PRT
<213> ORGANISM: Artificial Sequence
<220> FEATURE:
<223> OTHER INFORMATION: Her2/neu.998.I11 peptide 45.0124

<400> SEQUENCE: 368

Ser Pro Leu Asp Ser Thr Phe Tyr Arg Ser Ile
1               5                   10

<210> SEQ ID NO 369
<211> LENGTH: 11
<212> TYPE: PRT
<213> ORGANISM: Artificial Sequence
<220> FEATURE:
<223> OTHER INFORMATION: Her2/neu.1157.I11 peptide 45.0128

<400> SEQUENCE: 369

Leu Pro Ala Ala Arg Pro Ala Gly Ala Thr Ile
1               5                   10

<210> SEQ ID NO 370
<211> LENGTH: 11
<212> TYPE: PRT
<213> ORGANISM: Artificial Sequence
<220> FEATURE:
<223> OTHER INFORMATION: MAGE2.241.I11 peptide 45.0134

<400> SEQUENCE: 370

His Pro Arg Lys Leu Leu Met Gln Asp Leu Ile
1               5                   10

<210> SEQ ID NO 371
<211> LENGTH: 11
<212> TYPE: PRT
<213> ORGANISM: Artificial Sequence
<220> FEATURE:
<223> OTHER INFORMATION: MAGE2.274.I11 peptide 45.0135

<400> SEQUENCE: 371

Gly Pro Arg Ala Leu Ile Glu Thr Ser Tyr Ile
1               5                   10

<210> SEQ ID NO 372
<211> LENGTH: 11
<212> TYPE: PRT
<213> ORGANISM: Artificial Sequence
<220> FEATURE:
<223> OTHER INFORMATION: MAGE3.274.I11 peptide 45.0139

<400> SEQUENCE: 372

Gly Pro Arg Ala Leu Val Glu Thr Ser Tyr Ile
1               5                   10

<210> SEQ ID NO 373
<211> LENGTH: 11
<212> TYPE: PRT
<213> ORGANISM: Artificial Sequence
```

```
<220> FEATURE:
<223> OTHER INFORMATION: p53.63.I11 peptide 45.0140

<400> SEQUENCE: 373

Ala Pro Arg Met Pro Glu Ala Ala Pro Pro Ile
1               5                   10

<210> SEQ ID NO 374
<211> LENGTH: 11
<212> TYPE: PRT
<213> ORGANISM: Artificial Sequence
<220> FEATURE:
<223> OTHER INFORMATION: p53.97.I11 peptide 45.0141

<400> SEQUENCE: 374

Val Pro Ser Gln Lys Thr Tyr Gln Gly Ser Ile
1               5                   10

<210> SEQ ID NO 375
<211> LENGTH: 9
<212> TYPE: PRT
<213> ORGANISM: Artificial Sequence
<220> FEATURE:
<223> OTHER INFORMATION: HBV POL 541 analog peptide 1145.10

<400> SEQUENCE: 375

Phe Pro His Cys Leu Ala Phe Ala Tyr
1               5

<210> SEQ ID NO 376
<211> LENGTH: 9
<212> TYPE: PRT
<213> ORGANISM: Artificial Sequence
<220> FEATURE:
<223> OTHER INFORMATION: HBV POL 541 analog peptide 1145.09

<400> SEQUENCE: 376

Phe Pro Val Cys Leu Ala Phe Ser Tyr
1               5

<210> SEQ ID NO 377
<211> LENGTH: 11
<212> TYPE: PRT
<213> ORGANISM: Artificial Sequence
<220> FEATURE:
<223> OTHER INFORMATION: HBV.pol645 peptide 26.0570

<400> SEQUENCE: 377

Tyr Pro Ala Leu Met Pro Leu Tyr Ala Cys Ile
1               5                   10

<210> SEQ ID NO 378
<211> LENGTH: 10
<212> TYPE: PRT
<213> ORGANISM: Artificial Sequence
<220> FEATURE:
<223> OTHER INFORMATION: HLA-A3,2 allele-specific motif
<220> FEATURE:
<221> NAME/KEY: VARIANT
<222> LOCATION: (1)...(10)
<223> OTHER INFORMATION: Xaa at location 1 is any amino acid;
      Xaa at location 2 is V, L, or M;
      Xaa at location 3 is Y or D;
      Xaa at location 4 is any amino acid;
<220> FEATURE:
<223> OTHER INFORMATION: Xaa at location 5 is any amino acid;
      Xaa at location 6 is any amino acid;
      Xaa at location 8 is Q or N
```

```
<400> SEQUENCE: 378

Xaa Xaa Xaa Xaa Xaa Xaa Ile Xaa Lys Lys
 1               5                  10

<210> SEQ ID NO 379
<211> LENGTH: 10
<212> TYPE: PRT
<213> ORGANISM: Artificial Sequence
<220> FEATURE:
<223> OTHER INFORMATION: HLA-A11 allele-specific motif
<220> FEATURE:
<221> NAME/KEY: VARIANT
<222> LOCATION: (1)...(10)
<223> OTHER INFORMATION: Xaa at location 1 is any amino acid;
      Xaa at location 2 is T or V;
      Xaa at location 3 is M or F;
      Xaa at location 4 is any amino acid;
<220> FEATURE:
<223> OTHER INFORMATION: Xaa at location 5 is any amino acid;
      Xaa at location 6 is any amino acid;
      Xaa at location 7 is any amino acid

<400> SEQUENCE: 379

Xaa Xaa Xaa Xaa Xaa Xaa Xaa Gln Lys Lys
 1               5                  10

<210> SEQ ID NO 380
<211> LENGTH: 10
<212> TYPE: PRT
<213> ORGANISM: Artificial Sequence
<220> FEATURE:
<223> OTHER INFORMATION: HLA-A24.1 allele-specific motif
<220> FEATURE:
<221> NAME/KEY: VARIANT
<222> LOCATION: (1)...(10)
<223> OTHER INFORMATION: Xaa at location 1 is any amino acid;
      Xaa at location 3 is I or M;
      Xaa at location 4 is D, E, G K or P;
      Xaa at location 5 is L, M or N ;
<220> FEATURE:
<223> OTHER INFORMATION: Xaa at location 7 is N or V;
      Xaa at location 8 is A, E, K, Q or S;
      Xaa at location 9 is F or L;
      Xaa at location 10 is F or A

<400> SEQUENCE: 380

Xaa Tyr Xaa Xaa Xaa Val Xaa Xaa Xaa Xaa
 1               5                  10
```